(12) United States Patent  (10) Patent No.: US 9,193,665 B2
Chein  (45) Date of Patent: Nov. 24, 2015

(54) SYNTHESIS OF GALANAL COMPOUNDS AND ANALOGUES THEREOF

(71) Applicant: Academia Sinica, Taipei (TW)

(72) Inventor: Rong-Jie Chein, Taipei (TW)

(73) Assignee: Academia Sinica, Taipei (TW)

( * ) Notice: Subject to any disclaimer, the term of this patent is extended or adjusted under 35 U.S.C. 154(b) by 0 days.

(21) Appl. No.: 14/287,858

(22) Filed: May 27, 2014

(65) Prior Publication Data

US 2014/0350288 A1   Nov. 27, 2014

Related U.S. Application Data

(60) Provisional application No. 61/839,870, filed on Jun. 27, 2013, provisional application No. 61/827,674, filed on May 27, 2013.

(51) Int. Cl.
*C07C 69/96* (2006.01)
*C07C 47/36* (2006.01)
(Continued)

(52) U.S. Cl.
CPC ............... *C07C 69/96* (2013.01); *C07C 22/02* (2013.01); *C07C 29/15* (2013.01); *C07C 33/16* (2013.01);
(Continued)

(58) Field of Classification Search
None
See application file for complete search history.

(56) References Cited

U.S. PATENT DOCUMENTS

2013/0331323 A1   12/2013   Wu et al.

FOREIGN PATENT DOCUMENTS

EP   2330092 A2   6/2011
JP   63-162644 A   7/1988

OTHER PUBLICATIONS

Morita et al., New Diterpenes from Alpinia galangal WILD, Chemistry Letters, 1986, vol. 15, No. 7, pp. 1205-1208.
(Continued)

*Primary Examiner* — Yevegeny Valenrod

(74) *Attorney, Agent, or Firm* — Wolf, Greenfield & Sacks, P.C.

(57) ABSTRACT

The present disclosure provides methods of preparing glucagon-like peptide-1 (GLP-1) receptor modulators, such as compounds of Formula (II) or (VI), or intermediates thereof. The compounds that may be prepared by the described methods are useful for regulating blood glucose levels and/or treating a disease mediated by a GLP-1 receptor (e.g., diabetes).

10 Claims, 2 Drawing Sheets

(51) Int. Cl.
| | |
|---|---|
| C07C 69/753 | (2006.01) |
| C07C 35/37 | (2006.01) |
| C07C 49/753 | (2006.01) |
| C07C 69/757 | (2006.01) |
| C07C 49/757 | (2006.01) |
| C07C 62/32 | (2006.01) |
| C07C 29/15 | (2006.01) |
| C07C 45/00 | (2006.01) |
| C07C 45/41 | (2006.01) |
| C07C 67/30 | (2006.01) |
| C07C 253/00 | (2006.01) |
| C07C 253/30 | (2006.01) |
| C07C 259/06 | (2006.01) |
| C07C 271/24 | (2006.01) |
| C07C 275/28 | (2006.01) |
| C07C 211/31 | (2006.01) |
| C07C 215/42 | (2006.01) |
| C07C 321/20 | (2006.01) |
| C07C 323/15 | (2006.01) |
| C07C 225/14 | (2006.01) |
| C07C 323/22 | (2006.01) |
| C07C 323/28 | (2006.01) |
| C07C 327/06 | (2006.01) |
| C07C 327/16 | (2006.01) |
| C07C 33/16 | (2006.01) |
| C07C 33/44 | (2006.01) |
| C07C 69/24 | (2006.01) |
| C07C 69/33 | (2006.01) |
| C07C 69/587 | (2006.01) |
| C07C 47/46 | (2006.01) |
| C07F 9/117 | (2006.01) |
| C07C 22/02 | (2006.01) |
| C07D 303/46 | (2006.01) |
| C07C 69/007 | (2006.01) |

(52) U.S. Cl.
CPC ............... *C07C 33/44* (2013.01); *C07C 35/37* (2013.01); *C07C 45/00* (2013.01); *C07C 45/41* (2013.01); *C07C 47/36* (2013.01); *C07C 47/46* (2013.01); *C07C 49/757* (2013.01); *C07C 62/32* (2013.01); *C07C 67/30* (2013.01); *C07C 69/007* (2013.01); *C07C 69/24* (2013.01); *C07C 69/33* (2013.01); *C07C 69/587* (2013.01); *C07C 69/757* (2013.01); *C07C 211/31* (2013.01); *C07C 215/42* (2013.01); *C07C 225/14* (2013.01); *C07C 253/00* (2013.01); *C07C 253/30* (2013.01); *C07C 259/06* (2013.01); *C07C 271/24* (2013.01); *C07C 275/28* (2013.01); *C07C 321/20* (2013.01); *C07C 323/15* (2013.01); *C07C 323/22* (2013.01); *C07C 323/28* (2013.01); *C07C 327/06* (2013.01); *C07C 327/16* (2013.01); *C07D 303/46* (2013.01); *C07F 9/117* (2013.01); *C07C 2103/30* (2013.01)

(56) References Cited

OTHER PUBLICATIONS

Fernandez-Mateos et al., On the Mechanism and Kinetics of Radical Reactions of Epoxyketones and Epoxynitriles Induced by Titanocene Chloride, J Org Chem. Dec. 21, 2007;72(26):9973-82. Epub Nov. 29, 2007.

Justica et al., 7-endo radical cyclizations catalyzed by titanocene(III). Straightforward synthesis of terpenoids with seven-membered carbocycles. J Am Chem Soc. Oct. 26, 2005;127(42):14911-21.

Kumar et al., Synthesis of Labdane Diterpenes Galanal A and B from (+)-Sclareolide, Organic Letters, May 5, 2014, vol. 16, No. 11, pp. 2990-2992.

Miyoshi et al., Dietary ginger constituents, galanals A and B, are potent apoptosis inducers in Human T lymphoma Jurkat cells. Cancer Lett. Sep. 25, 2003;199(2):113-119.

Morita et al., Cytotoxic and Antifungal Diterpenes from the Seeds of Alpinia galanga, Planta Medica, 1988, vol. 54, No. 2, pp. 117-120.

Murase et al., Organoaluminum-Promoted Cyclization of Olefinic Epoxides. A New and Stereoselective Approach to Cyclohexane Frameworks, Bull Chem Soc Japan 1997 vol. 70, pp. 707-711.

White et al., Lewis acid and photochemically mediated cyclization of olefinic β-keto esters, J. Org. Chem., 1985 vol. 50, pp. 1939-1948.

Willard et al., Small molecule allosteric modulation of the glucagon-like Peptide-1 receptor enhances the insulinotropic effect of oxyntomodulin. Mol Pharmacol. Dec. 2012;82(6):1066-73.

Zinkel et al., Structure of strobic acid, Tetrahedron, 1973 vol. 29, pp. 1441-1444.

SYNTHESIS OF GALANAL COMPOUNDS AND ANALOGUES THEREOF

RELATED APPLICATIONS

The present application claims priority under 35 U.S.C. §119(e) to U.S. provisional patent applications, 61/827,674, filed May 27, 2013 and 61/839,870, filed Jun. 27, 2013, the entire content of each of which is incorporated by reference herein.

FIELD OF INVENTION

This disclosure relates to processes for synthesizing galanal A and galanal B compounds, and analogues or intermediates thereof. The disclosure also relates to the compounds thus synthesized and uses thereof, e.g., in regulating blood glucose level and treating diabetes.

BACKGROUND

Supply of galanal A and galanal B compounds having antimicrobial, anti-cancer, anti-atherosclerosis, anti-diabetes and anti-platelet activities is conventionally provided by the flower bud, rhizome, stem, leaf and seed from several species of Zingiberaceae. The structures of galanal A and galanal B are shown below, with the number assignment of the carbon atoms.

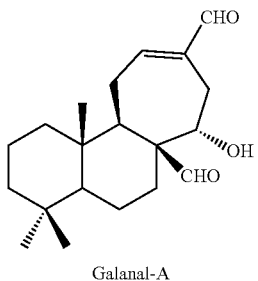

Galanal-A (RJ-20)

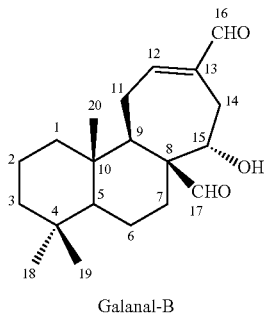

Galanal-B (RJ-21)

However, the levels of galanal A and galanal B are very low in these edible plants. So far, there is no viable synthetic route for the preparation of galanal A and galanal B. Meanwhile, the effects of galanal A or galanal B in the treatment of diseases mediated by the GLP-1 (Glucagon-Like Peptide-1) receptor have not been investigated yet.

SUMMARY OF THE INVENTION

This disclosure provides processes for synthesizing galanal compounds (e.g., galanal A or galanal B), and analogues thereof (galanal analogues, such as compounds of Formula (II) or (VI)). It is thought that the galanal compounds and analogues thereof as described herein are glucagon-like peptide-1 (GLP-1) receptor modulators and may be useful in treating a disease mediated by a GLP-1 receptor (e.g., diabetes, a metabolic disorder, a neurodegenarative disease, or cardiovascular disease) and/or regulating blood glucose levels in a subject in need thereof.

This disclosure also provides compounds of any one of Formulae (I), (III) to (V), and (VII) to (VIII), which are useful as synthetic intermediates in synthesizing galanal A, galanal B, and/or analogues thereof.

In one aspect, the present disclosure provides compounds of Formula (I):

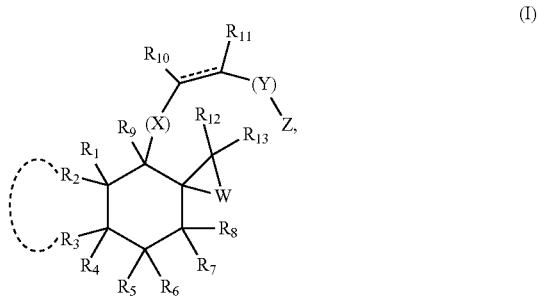

(I)

wherein:
W is —O—, —S— or —NR'—, wherein R' is hydrogen, a cyclic or acyclic, saturated or unsaturated, substituted or unsubstituted, branched or unbranched, (hetero)aliphatic group having 1 to 16 carbon atoms, an ester group, a ketone group, or a thione group;

X and Y are each independently a single bond, or a saturated or unsaturated, substituted or unsubstituted, branched or unbranched, (hetero)aliphatic group having 1 to 3 carbon atoms;

Z is alkenyl, alkynyl, an amide group, an ester group, an aldehyde group, a thioaldehyde group, a nitrile group, an imino group, a ketone group, a thione group, an isonitrile group, an isothiocyanide group, a thioate group, a thioamide, a dithioate, a carbamate group, a thiocarbamate group, an isocyanato group, or an isothiocyanato group;

$R_1$, $R_2$, $R_3$, $R_4$, $R_5$, $R_6$, $R_7$, $R_8$, $R_9$, $R_{12}$ and $R_{13}$ are each independently hydrogen, halogen, or a cyclic or acyclic, substituted or unsubstituted, branched or unbranched, (hetero)aliphatic group having 1 to 6 carbon atoms, or $R_2$ and $R_3$ may join to form cycloalkyl, heterocycloalkyl, aryl, or heteroaryl; and $R_{10}$ and $R_{11}$ are each independently hydrogen, halogen, a cyclic or acyclic, saturated or unsaturated, substituted or unsubstituted, branched or unbranched, (hetero)aliphatic group having 1 to 6 carbon atoms, an amino group, an amide group, an ester group, an aldehyde group, a nitrile, an imino group, a ketone group, a thione group, an isonitrile group, an isothiocyanide group, a carbamate group, or a thiocarbamate group.

All compounds described herein include the compounds themselves, as well as their salts and stereoisomers, if applicable. The salts, for example, can be formed between a positively charged substituent (e.g., amino) on a compound and an anion. Suitable anions include, but are not limited to, chloride, bromide, iodide, sulfate, nitrate, phosphate, citrate, methanesulfonate, trifluoroacetate, and acetate. Likewise, a negatively charged substituent (e.g., carboxylate) on a compound can form a salt with a cation. Suitable cations include, but are not limited to, sodium ion, potassium ion, magnesium ion, calcium ion, and an ammonium cation such as tetramethylammonium ion. In certain embodiments, a compound described herein is not galanal A or galanal B.

In certain embodiments, a salt described herein is a pharmaceutically acceptable salt. The term "pharmaceutically acceptable salt" refers to those salts which are, within the scope of sound medical judgment, suitable for use in contact with the tissues of a subject (e.g., a human or non-human animal) without undue toxicity, irritation, allergic response and the like, and are commensurate with a reasonable benefit/risk ratio. Pharmaceutically acceptable salts are well known in the art. For example, Berge et al., describe pharmaceutically acceptable salts in detail in *J. Pharmaceutical Sciences*, 1977, 66, 1-19, incorporated herein by reference. Pharmaceutically acceptable salts of the compounds described herein include those derived from suitable inorganic and organic acids and bases. In certain embodiments, a pharmaceutically acceptable salt can be a salt described herein.

Compounds described herein can comprise one or more asymmetric centers, and thus can exist in various isomeric forms, e.g., enantiomers and/or diastereomers. For example, the compounds described herein can be in the form of an individual enantiomer, diastereomer or geometric isomer, or can be in the form of a mixture of stereoisomers, including racemic mixtures and mixtures enriched in one or more stereoisomer. Isomers can be isolated from mixtures by methods known to those skilled in the art, including chiral high pressure liquid chromatography (HPLC) and the formation and crystallization of chiral salts; or preferred isomers can be prepared by asymmetric syntheses. See, for example, Jacques et al., *Enantiomers, Racemates and Resolutions* (Wiley Interscience, New York, 1981); Wilen et al., *Tetrahedron* 33:2725 (1977); Eliel, *Stereochemistry of Carbon Compounds* (McGraw-Hill, NY, 1962); and Wilen, *Tables of Resolving Agents and Optical Resolutions* p. 268 (E. L. Eliel, Ed., Univ. of Notre Dame Press, Notre Dame, Ind. 1972). The present disclosure additionally encompasses compounds described herein as individual isomers substantially free of other isomers, and alternatively, as mixtures of various isomers.

In a formula, ═══ is a single or double bond, and - - - is absent (and therefore any substituent attached thereto is also absent) or a single bond.

Unless otherwise specified, a moiety described herein may be unsubstituted or may be substituted (e.g., at least one hydrogen atom of the moiety being replaced with a non-hydrogen atom or group). When a group described herein is substituted, the group may be substituted, as valency permits, with one or more substituents independently selected from the group consisting of $C_{1-6}$ alkyl (e.g., unsubstituted $C_{1-6}$ alkyl (e.g., methyl, ethyl, propyl, or butyl) or substituted $C_{1-6}$ alkyl (e.g., —$CF_3$, —$CH_2$—$CF_3$, or —$C_2F_5$)), —$OR^{a1}$ (e.g., —OH, —OMe, or —OEt), —$N(R^{a1})_2$ (e.g., —$NH_2$, —NHMe, or —$NMe_2$), —$SR^{a1}$ (e.g., —SH or —SMe), ═O, ═S, —CHO, —C(═O)$N(R^{a1})_2$ (e.g., —C(═O)$NH_2$, —C(═O)NHMe, or —C(═O)$NMe_2$), —CN, C(═O)$OR^{a1}$ (e.g., —C(═O)OH, —C(═O)OMe, or —C(═O)OEt), —OC(═O)$R^{b1}$ (e.g., —OC(═O)Me, —OC(═O)Et, or —OC(═O)$(CH_2)_7$CH═CH$CH_2$CH═CH$(CH_2)_4CH_3$), —OC(═O)$OR^{a1}$ (e.g., —OC(═O)OMe, —OC(═O)OEt, or —OC(═O)O$(CH_2)_7$CH═CH$CH_2$CH═CH$(CH_2)_4$ $CH_3$)), —$C(R^{b1})_2OR^{a1}$ (e.g., —$CH_2$—OH or —$CH_2$—OMe), —$C(R^{b1})_2SR^{a1}$ (e.g., —$CH_2$—SH or —$CH_2$—SMe), —$C(R^{b1})_2N(R^{a1})_2$ (e.g., —$CH_2$—$NH_2$, —$CH_2$—NHMe, or —$CH_2$—$NMe_2$), and —$C(R^{b1})_2OC(═O)OR^{a1}$ (e.g., —$CH_2$—OC(═O)OMe, —$CH_2$—OC(═O)OEt, or —$CH_2$—OC(═O)O$(CH_2)_7$CH═CH$CH_2$CH═CH$(CH_2)_4$ $CH_3$)), wherein each instance of $R^{a1}$ is independently H, $C_{1-6}$ alkyl (e.g., unsubstituted $C_{1-6}$ alkyl (e.g., methyl, ethyl, propyl, or butyl) or substituted $C_{1-6}$ alkyl (e.g., —$CF_3$, —$CH_2$—$CF_3$, or —$C_2F_5$)), $C_{2-6}$ alkenyl (e.g., unsubstituted $C_{2-6}$ alkenyl (e.g., vinyl)), 3- to 10-membered cycloalkyl (e.g., unsubstituted 3- to 10-membered cycloalkyl (e.g., cyclopropyl)), or 6- to 10-membered aryl (e.g., phenyl (e.g., unsubstituted phenyl or substituted phenyl)), and each instance of $R^{b1}$ is independently H, halogen (e.g., F, Cl, Br, or I (iodine)), $C_{1-6}$ alkyl (e.g., unsubstituted $C_{1-6}$ alkyl (e.g., methyl, ethyl, propyl, or butyl) or substituted $C_{1-6}$ alkyl (e.g., —$CF_3$, —$CH_2$—$CF_3$, or —$C_2F_5$)), $C_{2-6}$ alkenyl (e.g., unsubstituted $C_{2-6}$ alkenyl (e.g., vinyl)), 3- to 10-membered cycloalkyl (e.g., unsubstituted 3- to 10-membered cycloalkyl (e.g., cyclopropyl)), or 6- to 10-membered aryl (e.g., phenyl (e.g., unsubstituted phenyl or substituted phenyl)).

When a range of values is listed, it is intended to encompass each value and sub-range within the range. For example "$C_{1-6}$ alkyl" is intended to encompass, $C_1$, $C_2$, $C_3$, $C_4$, $C_5$, $C_6$, $C_{1-6}$, $C_{1-5}$, $C_{1-4}$, $C_{1-3}$, $C_{1-2}$, $C_{2-6}$, $C_{2-5}$, $C_{2-4}$, $C_{2-3}$, $C_{3-6}$, $C_{3-5}$, $C_{3-4}$, $C_{4-6}$, $C_{4-5}$, and $C_{5-6}$ alkyl.

The term "(hetero)aliphatic" refers to aliphatic or heteroaliphatic. The term "aliphatic" refers to alkyl, alkenyl, alkynyl, and carbocyclic groups. The term "heteroaliphatic" refers to heteroalkyl, heteroalkenyl, heteroalkynyl, and heterocyclic groups.

The term "alkyl" refers to a radical of a straight-chained ("unbranched") or branched, saturated, hydrocarbon group. In some embodiments, an alkyl group has 1 to 6 carbon atoms ("$C_{1-6}$ alkyl"). Examples of $C_{1-6}$ alkyl groups include methyl ($C_1$), ethyl ($C_2$), n-propyl ($C_3$), isopropyl ($C_3$), n-butyl ($C_4$), tert-butyl ($C_4$), sec-butyl ($C_4$), iso-butyl ($C_4$), n-pentyl ($C_5$), 3-pentanyl ($C_5$), amyl ($C_5$), neopentyl ($C_5$), 3-methyl-2-butanyl ($C_5$), tertiary amyl ($C_5$), and n-hexyl ($C_6$).

The term "alkenyl" refers to a radical of a straight-chained or branched hydrocarbon group having one or more carbon-carbon double bonds (e.g., 1, 2, 3, or 4 double bonds). In some embodiments, an alkenyl group has 2 to 6 carbon atoms ("$C_{2-6}$ alkenyl"). The one or more carbon-carbon double bonds can be internal (such as in 2-butenyl) or terminal (such as in 1-butenyl). Examples of $C_{2-6}$ alkenyl groups include ethenyl ($C_2$), 1-propenyl ($C_3$), 2-propenyl ($C_3$), 1-butenyl ($C_4$), 2-butenyl ($C_4$), butadienyl ($C_4$), pentenyl ($C_5$), pentadienyl ($C_5$), and hexenyl ($C_6$).

The term "alkynyl" refers to a radical of a straight-chained or branched hydrocarbon group having one or more carbon-carbon triple bonds (e.g., 1, 2, 3, or 4 triple bonds). In some embodiments, an alkynyl group has 2 to 6 carbon atoms ("$C_{2-6}$ alkynyl"). The one or more carbon-carbon triple bonds can be internal (such as in 2-butynyl) or terminal (such as in 1-butynyl). Examples of $C_{2-6}$ alkynyl groups include ethynyl ($C_2$), 1-propynyl ($C_3$), 2-propynyl ($C_3$), 1-butynyl ($C_4$), 2-butynyl ($C_4$), pentynyl ($C_5$), and hexynyl ($C_6$).

"Heteroalkyl" refers to an alkyl group as defined herein which further includes at least one heteroatom (e.g., 1, 2, 3, or 4 heteroatoms) selected from oxygen, nitrogen, or sulfur within (i.e., inserted between adjacent carbon atoms of) and/or placed at one or more terminal position(s) of the parent chain. In some embodiments, a heteroalkyl group is a saturated group having 1 to 16 carbon atoms and 1 or more heteroatoms within the parent chain ("hetero$C_{1-16}$ alkyl"). In some embodiments, a heteroalkyl group is a saturated group having 1 to 6 carbon atoms and 1 or more heteroatoms within the parent chain ("hetero$C_{1-6}$ alkyl"). In some embodiments, a heteroalkyl group is a saturated group having 1 to 3 carbon atoms and 1 or more heteroatoms within the parent chain ("heteroC$_{1-3}$ alkyl"). Unless otherwise specified, each instance of a heteroalkyl group is independently unsubstituted or substituted with one or more substituents.

"Heteroalkenyl" refers to an alkenyl group as defined herein which further includes at least one heteroatom (e.g., 1, 2, 3, or 4 heteroatoms) selected from oxygen, nitrogen, or sulfur within (i.e., inserted between adjacent carbon atoms of) and/or placed at one or more terminal position(s) of the parent chain. In some embodiments, a heteroalkenyl group has 2 to 16 carbon atoms, at least one double bond, and 1 or more heteroatoms within the parent chain ("heteroC$_{2-16}$ alkenyl"). In some embodiments, a heteroalkenyl group has 2 to 6 carbon atoms, at least one double bond, and 1 or more heteroatoms within the parent chain ("heteroC$_{2-6}$ alkenyl"). In some embodiments, a heteroalkenyl group has 2 to 3 carbon atoms, at least one double bond, and 1 or more heteroatoms within the parent chain ("heteroC$_{2-3}$ alkenyl"). Unless otherwise specified, each instance of a heteroalkenyl group is independently unsubstituted or substituted with one or more substituents.

"Heteroalkynyl" refers to an alkynyl group as defined herein which further includes at least one heteroatom (e.g., 1, 2, 3, or 4 heteroatoms) selected from oxygen, nitrogen, or sulfur within (i.e., inserted between adjacent carbon atoms of) and/or placed at one or more terminal position(s) of the parent chain. In some embodiments, a heteroalkynyl group has 2 to 16 carbon atoms, at least one triple bond, and 1 or more heteroatoms within the parent chain ("heteroC$_{2-16}$ alkynyl"). In some embodiments, a heteroalkynyl group has 2 to 6 carbon atoms, at least one triple bond, and 1 or more heteroatoms within the parent chain ("heteroC$_{2-6}$ alkynyl"). In some embodiments, a heteroalkynyl group has 2 to 3 carbon atoms, at least one triple bond, and 1 or more heteroatoms within the parent chain ("heteroC$_{2-3}$ alkynyl"). Unless otherwise specified, each instance of a heteroalkynyl group is independently unsubstituted or substituted with one or more substituents.

"Carbocyclyl," "carbocycle," or "carbocyclic" refers to a radical of a non-aromatic cyclic hydrocarbon group having from 3 to 10 ring carbon atoms ("C$_{3-10}$ carbocyclyl") and zero heteroatoms in the non-aromatic ring system. In some embodiments, a carbocyclyl group has 3 to 8 ring carbon atoms ("C$_{3-8}$ carbocyclyl"). In some embodiments, a carbocyclyl group has 3 to 6 ring carbon atoms ("C$_{3-6}$ carbocyclyl"). In some embodiments, a carbocyclyl group has 3 to 6 ring carbon atoms ("C$_{3-6}$ carbocyclyl"). In some embodiments, a carbocyclyl group has 5 to 10 ring carbon atoms ("C$_{5-10}$ carbocyclyl"). Exemplary C$_{3-6}$ carbocyclyl groups include, without limitation, cyclopropyl (C$_3$), cyclopropenyl (C$_3$), cyclobutyl (C$_4$), cyclobutenyl (C$_4$), cyclopentyl (C$_5$), cyclopentenyl (C$_5$), cyclohexyl (C$_6$), cyclohexenyl (C$_6$), cyclohexadienyl (C$_6$), and the like. Exemplary C$_{3-8}$ carbocyclyl groups include, without limitation, the aforementioned C$_{3-6}$ carbocyclyl groups as well as cycloheptyl (C$_7$), cycloheptenyl (C$_7$), cycloheptadienyl (C$_7$), cycloheptatrienyl (C$_7$), cyclooctyl (C$_8$), cyclooctenyl (C$_8$), bicyclo[2.2.1]heptanyl (C$_7$), bicyclo[2.2.2]octanyl (C$_8$), and the like. Exemplary C$_{3-10}$ carbocyclyl groups include, without limitation, the aforementioned C$_{3-8}$ carbocyclyl groups as well as cyclononyl (C$_9$), cyclononenyl (C$_9$), cyclodecyl (C$_{10}$), cyclodecenyl (C$_{10}$), octahydro-1H-indenyl (C$_9$), decahydronaphthalenyl (C$_{10}$), spiro[4.5]decanyl (C$_{10}$), and the like. As the foregoing examples illustrate, in certain embodiments, the carbocyclyl group is either monocyclic ("monocyclic carbocyclyl") or contain a fused, bridged, or spiro ring system such as a bicyclic system ("bicyclic carbocyclyl"). Carbocyclyl can be saturated, and saturated carbocyclyl is referred to as "cycloalkyl." In some embodiments, carbocyclyl is a monocyclic, saturated carbocyclyl group having from 3 to 10 ring carbon atoms ("C$_{3-10}$ cycloalkyl"). In some embodiments, a cycloalkyl group has 3 to 8 ring carbon atoms ("C$_{3-8}$ cycloalkyl"). In some embodiments, a cycloalkyl group has 3 to 6 ring carbon atoms ("C$_{3-6}$ cycloalkyl"). In some embodiments, a cycloalkyl group has 5 to 6 ring carbon atoms ("C$_{5-6}$ cycloalkyl"). In some embodiments, a cycloalkyl group has 5 to 10 ring carbon atoms ("C$_{5-10}$ cycloalkyl"). Examples of C$_{5-6}$ cycloalkyl groups include cyclopentyl (C$_5$) and cyclohexyl (C$_5$). Examples of C$_{3-6}$ cycloalkyl groups include the aforementioned C$_{5-6}$ cycloalkyl groups as well as cyclopropyl (C$_3$) and cyclobutyl (C$_4$). Examples of C$_{3-8}$ cycloalkyl groups include the aforementioned C$_{3-6}$ cycloalkyl groups as well as cycloheptyl (C$_7$) and cyclooctyl (C$_8$). Unless otherwise specified, each instance of a cycloalkyl group is independently unsubstituted (an "unsubstituted cycloalkyl") or substituted (a "substituted cycloalkyl") with one or more substituents. In certain embodiments, the cycloalkyl group is unsubstituted C$_{3-10}$ cycloalkyl. In certain embodiments, the cycloalkyl group is substituted C$_{3-10}$ cycloalkyl. Carbocyclyl can be partially unsaturated. Carbocyclyl including one or more C=C double bond in the carbocyclic ring is referred to as "cycloalkenyl." Carbocyclyl including one or more C≡C triple bond in the carbocyclic ring is referred to as "cycloalkynyl." Carbocyclyl includes aryl. "Carbocyclyl" also includes ring systems wherein the carbocyclic ring, as defined above, is fused with one or more aryl or heteroaryl groups wherein the point of attachment is on the carbocyclic ring, and in such instances, the number of carbons continue to designate the number of carbons in the carbocyclic ring system. Unless otherwise specified, each instance of a carbocyclyl group is independently optionally substituted, i.e., unsubstituted (an "unsubstituted carbocyclyl") or substituted (a "substituted carbocyclyl") with one or more substituents. In certain embodiments, the carbocyclyl group is unsubstituted C$_{3-10}$ carbocyclyl. In certain embodiments, the carbocyclyl group is substituted C$_{3-10}$ carbocyclyl.

"Heterocyclyl," "heterocycle," or "heterocyclic" refers to a radical of a 3- to 10-membered non-aromatic ring system having ring carbon atoms and 1 to 4 ring heteroatoms, wherein each heteroatom is independently selected from nitrogen, oxygen, sulfur, boron, phosphorus, and silicon ("3-10 membered heterocyclyl"). In heterocyclyl groups that contain one or more nitrogen atoms, the point of attachment can be a carbon or nitrogen atom, as valency permits. A heterocyclyl group can either be monocyclic ("monocyclic heterocyclyl") or a fused, bridged, or spiro ring system, such as a bicyclic system ("bicyclic heterocyclyl"), and can be saturated ("heterocycloalkyl") or can be partially unsaturated. Heterocyclyl bicyclic ring systems can include one or more heteroatoms in one or both rings. Heterocyclyl includes heteroaryl. Heterocyclyl also includes ring systems wherein the heterocyclic ring, as defined above, is fused with one or more carbocyclyl groups wherein the point of attachment is either on the carbocyclyl or heterocyclic ring, or ring systems wherein the heterocyclic ring, as defined above, is fused with one or more aryl or heteroaryl groups, wherein the point of attachment is on the heterocyclic ring, and in such instances, the number of ring members continue to designate the number of ring members in the heterocyclic ring system. Unless otherwise specified, each instance of heterocyclyl is independently optionally substituted, i.e., unsubstituted (an "unsubstituted heterocyclyl") or substituted (a "substituted heterocyclyl") with one or more substituents. In certain embodiments, the heterocyclyl group is unsubstituted 3-10 membered heterocyclyl. In certain embodiments, the heterocyclyl group is substituted 3-10 membered heterocyclyl.

In some embodiments, a heterocyclyl group is a 5-10 membered non-aromatic ring system having ring carbon atoms and 1-4 ring heteroatoms, wherein each heteroatom is independently selected from nitrogen, oxygen, sulfur, boron, phosphorus, and silicon ("5-10 membered heterocyclyl"). In some embodiments, a heterocyclyl group is a 5-8 membered non-aromatic ring system having ring carbon atoms and 1-4 ring heteroatoms, wherein each heteroatom is independently selected from nitrogen, oxygen, and sulfur ("5-8 membered heterocyclyl"). In some embodiments, a heterocyclyl group is a 5-6 membered non-aromatic ring system having ring carbon atoms and 1-4 ring heteroatoms, wherein each heteroatom is independently selected from nitrogen, oxygen, and sulfur ("5-6 membered heterocyclyl"). In some embodiments, the 5-6 membered heterocyclyl has 1-3 ring heteroatoms selected from nitrogen, oxygen, and sulfur. In some embodiments, the 5-6 membered heterocyclyl has 1-2 ring heteroatoms selected from nitrogen, oxygen, and sulfur. In some embodiments, the 5-6 membered heterocyclyl has one ring heteroatom selected from nitrogen, oxygen, and sulfur.

Exemplary 3-membered heterocyclyl groups containing one heteroatom include, without limitation, azirdinyl, oxiranyl, and thiiranyl. Exemplary 4-membered heterocyclyl groups containing one heteroatom include, without limitation, azetidinyl, oxetanyl and thietanyl. Exemplary 5-membered heterocyclyl groups containing one heteroatom include, without limitation, tetrahydrofuranyl, dihydrofuranyl, tetrahydrothiophenyl, dihydrothiophenyl, pyrrolidinyl, dihydropyrrolyl and pyrrolyl-2,5-dione. Exemplary 5-membered heterocyclyl groups containing two heteroatoms include, without limitation, dioxolanyl, oxasulfuranyl, disulfuranyl, and oxazolidin-2-one. Exemplary 5-membered heterocyclyl groups containing three heteroatoms include, without limitation, thiazolinyl, oxadiazolinyl, and thiadiazolinyl. Exemplary 6-membered heterocyclyl groups containing one heteroatom include, without limitation, piperidinyl, tetrahydropyranyl, dihydropyridinyl, and thianyl. Exemplary 6-membered heterocyclyl groups containing two heteroatoms include, without limitation, piperazinyl, morpholinyl, dithianyl, and dioxanyl. Exemplary 6-membered heterocyclyl groups containing three heteroatoms include, without limitation, thiazinanyl. Exemplary 7-membered heterocyclyl groups containing one heteroatom include, without limitation, azepanyl, oxepanyl and thiepanyl. Exemplary 8-membered heterocyclyl groups containing one heteroatom include, without limitation, azocanyl, oxecanyl and thiocanyl. Exemplary 5-membered heterocyclyl groups fused to a $C_6$ aryl ring (also referred to herein as a 5,6-bicyclic heterocyclic ring) include, without limitation, indolinyl, isoindolinyl, dihydrobenzofuranyl, dihydrobenzothienyl, benzoxazolinonyl, and the like. Exemplary 6-membered heterocyclyl groups fused to an aryl ring (also referred to herein as a 6,6-bicyclic heterocyclic ring) include, without limitation, tetrahydroquinolinyl, tetrahydroisoquinolinyl, and the like.

"Aryl" refers to a radical of a monocyclic or polycyclic (e.g., bicyclic or tricyclic) 4n+2 aromatic ring system (e.g., having 6, 10, or 14 pi electrons shared in a cyclic array) having 6-14 ring carbon atoms and zero heteroatoms provided in the aromatic ring system ("$C_{6-14}$ aryl"). In some embodiments, an aryl group has six ring carbon atoms ("$C_6$ aryl"; e.g., phenyl). In some embodiments, an aryl group has ten ring carbon atoms ("$C_{10}$ aryl"; e.g., naphthyl such as 1-naphthyl and 2-naphthyl). In some embodiments, an aryl group has fourteen ring carbon atoms ("$C_{14}$ aryl"; e.g., anthracyl). "Aryl" also includes ring systems wherein the aryl ring, as defined above, is fused with one or more carbocyclyl or heterocyclyl groups wherein the radical or point of attachment is on the aryl ring, and in such instances, the number of carbon atoms continue to designate the number of carbon atoms in the aryl ring system. Unless otherwise specified, each instance of an aryl group is independently optionally substituted, i.e., unsubstituted (an "unsubstituted aryl") or substituted (a "substituted aryl") with one or more substituents. In certain embodiments, the aryl group is unsubstituted $C_{6-14}$ aryl. In certain embodiments, the aryl group is substituted $C_{6-14}$ aryl.

"Aralkyl" is a subset of alkyl and aryl, as defined herein, and refers to an optionally substituted alkyl group substituted by an optionally substituted aryl group. In certain embodiments, the aralkyl is optionally substituted benzyl. In certain embodiments, the aralkyl is benzyl. In certain embodiments, the aralkyl is optionally substituted phenethyl. In certain embodiments, the aralkyl is phenethyl.

"Aralkenyl" is a subset of alkenyl and aryl, as defined herein, and refers to an optionally substituted alkenyl group substituted by an optionally substituted aryl group. An example of aralkenyl is styrenyl (i.e., —CH=CHPh).

"Aralkynyl" is a subset of alkynyl and aryl, as defined herein, and refers to an optionally substituted alkynyl group substituted by an optionally substituted aryl group.

"Heteroaryl" refers to a radical of a 5-10 membered monocyclic or bicyclic 4n+2 aromatic ring system (e.g., having 6 or 10 pi electrons shared in a cyclic array) having ring carbon atoms and 1-4 ring heteroatoms provided in the aromatic ring system, wherein each heteroatom is independently selected from nitrogen, oxygen and sulfur ("5-10 membered heteroaryl"). In heteroaryl groups that contain one or more nitrogen atoms, the point of attachment can be a carbon or nitrogen atom, as valency permits. Heteroaryl bicyclic ring systems can include one or more heteroatoms in one or both rings. "Heteroaryl" includes ring systems wherein the heteroaryl ring, as defined above, is fused with one or more carbocyclyl or heterocyclyl groups wherein the point of attachment is on the heteroaryl ring, and in such instances, the number of ring members continue to designate the number of ring members in the heteroaryl ring system. "Heteroaryl" also includes ring systems wherein the heteroaryl ring, as defined above, is fused with one or more aryl groups wherein the point of attachment is either on the aryl or heteroaryl ring, and in such instances, the number of ring members designates the number of ring members in the fused (aryl/heteroaryl) ring system. Bicyclic heteroaryl groups wherein one ring does not contain a heteroatom (e.g., indolyl, quinolinyl, carbazolyl, and the like) the point of attachment can be on either ring, i.e., either the ring bearing a heteroatom (e.g., 2-indolyl) or the ring that does not contain a heteroatom (e.g., 5-indolyl).

In some embodiments, a heteroaryl group is a 5-10 membered aromatic ring system having ring carbon atoms and 1-4 ring heteroatoms provided in the aromatic ring system, wherein each heteroatom is independently selected from nitrogen, oxygen, and sulfur ("5-10 membered heteroaryl"). In some embodiments, a heteroaryl group is a 5-8 membered aromatic ring system having ring carbon atoms and 1-4 ring heteroatoms provided in the aromatic ring system, wherein each heteroatom is independently selected from nitrogen, oxygen, and sulfur ("5-8 membered heteroaryl"). In some embodiments, a heteroaryl group is a 5-6 membered aromatic ring system having ring carbon atoms and 1-4 ring heteroatoms provided in the aromatic ring system, wherein each heteroatom is independently selected from nitrogen, oxygen, and sulfur ("5-6 membered heteroaryl"). In some embodiments, the 5-6 membered heteroaryl has 1-3 ring heteroatoms selected from nitrogen, oxygen, and sulfur. In some embodiments, the 5-6 membered heteroaryl has 1-2 ring heteroatoms selected from nitrogen, oxygen, and sulfur. In some embodiments, the 5-6 membered heteroaryl has 1 ring heteroatom selected from nitrogen, oxygen, and sulfur. Unless otherwise specified, each instance of a heteroaryl group is independently optionally substituted, i.e., unsubstituted (an "unsubstituted heteroaryl") or substituted (a "substituted heteroaryl") with one or more substituents. In certain embodiments, the heteroaryl group is unsubstituted 5-14 membered heteroaryl. In certain embodiments, the heteroaryl group is substituted 5-14 membered heteroaryl.

Exemplary 5-membered heteroaryl groups containing one heteroatom include, without limitation, pyrrolyl, furanyl and thiophenyl. Exemplary 5-membered heteroaryl groups containing two heteroatoms include, without limitation, imidazolyl, pyrazolyl, oxazolyl, isoxazolyl, thiazolyl, and isothiazolyl. Exemplary 5-membered heteroaryl groups containing three heteroatoms include, without limitation, triazolyl, oxadiazolyl, and thiadiazolyl. Exemplary 5-membered heteroaryl groups containing four heteroatoms include, without limitation, tetrazolyl. Exemplary 6-membered heteroaryl groups containing one heteroatom include, without limitation, pyridinyl. Exemplary 6-membered heteroaryl groups containing two heteroatoms include, without limitation, pyridazinyl, pyrimidinyl, and pyrazinyl. Exemplary 6-membered heteroaryl groups containing three or four heteroatoms include, without limitation, triazinyl and tetrazinyl, respectively. Exemplary 7-membered heteroaryl groups containing one heteroatom include, without limitation, azepinyl, oxepinyl, and thiepinyl. Exemplary 5,6-bicyclic heteroaryl groups include, without limitation, indolyl, isoindolyl, indazolyl, benzotriazolyl, benzothiophenyl, isobenzothiophenyl, benzofuranyl, benzoisofuranyl, benzimidazolyl, benzoxazolyl, benzisoxazolyl, benzoxadiazolyl, benzthiazolyl, benzisothiazolyl, benzthiadiazolyl, indolizinyl, and purinyl. Exemplary 6,6-bicyclic heteroaryl groups include, without limitation, naphthyridinyl, pteridinyl, quinolinyl, isoquinolinyl, cinnolinyl, quinoxalinyl, phthalazinyl, and quinazolinyl.

The term "oxo" refers to the a moiety of the formula: =O.

The term "amide" or "amide group" refers to a moiety of the formula: —N(R$^{pp}$)C(=O)R$^{qq}$, wherein R$^{pp}$ is a nitrogen atom substituent described herein, and R$^{qq}$ is a carbon atom substituent described herein.

The term "ester" or "ester group" refers to a moiety of the formula: —C(=O)OR$^{rr}$ or —OC(=O)R$^{rr}$, wherein R$^{rr}$ is an oxygen atom substituent described herein.

The term "phosphate" or "phosphate group" refers to a moiety of the formula: —OP(=O)(OR$^{oo}$)$_2$, wherein each instance of R$^{oo}$ is independently an oxygen atom substituent described herein or a cationic counterion.

The term "carboxyl" or "carboxyl group" refers to a moiety of the formula: —C(=O)OH.

The term "aldehyde" or "aldehyde group" refers to a moiety of the formula: —C(=O)H.

The term "thialdehyde" or "thialdehyde group" refers to a moiety of the formula: —C(=S)H.

The term "nitrile" or "nitrile group" refers to a moiety of the formula: —CN or -L-CN, wherein L is substituted or unsubstituted, branched or unbranched, $C_{1-16}$ alkylene; substituted or unsubstituted, branched or unbranched, $C_{2-16}$ alkenylene; or substituted or unsubstituted, branched or unbranched, $C_{2-16}$ alkynylene.

The term "alcohol," "alcohol group," "hydroxyl," or "hydroxy" refers to the group —OH. The term "substituted hydroxyl" or "substituted hydroxyl" refers to a hydroxyl group wherein the oxygen atom directly attached to the parent molecule is substituted with a group other than hydrogen, and includes groups selected from —OR$^{aa}$, —ON(R$^{bb}$)$_2$, —OC(=O)SR$^{aa}$, —OC(=O)R$^{aa}$, —OCO$_2$R$^{aa}$, —OC(=O)N(R$^{bb}$)$_2$, —OC(=NR$^{bb}$)R$^{aa}$, —OC(=NR$^{bb}$)OR$^{aa}$, —OC(=NR$^{bb}$)N(R$^{bb}$)$_2$, —OS(=O)R$^{aa}$, —OSO$_2$R$^{aa}$, —OSi(R$^{aa}$)$_3$, —OP(R$^{cc}$)$_2$, —OP(R$^{cc}$)$_3$, —OP(=O)$_2$R$^{aa}$, —OP(=O)(R$^{aa}$)$_2$, —OP(=O)(OR$^{cc}$)$_2$, —OP(=O)$_2$N(R$^{bb}$)$_2$, and —OP(=O)(NR$^{bb}$)$_2$, wherein R$^{aa}$, R$^{bb}$, and R$^{cc}$ are as defined herein.

The term "amino" or "amino group" refers to a moiety of the formula: —N(R$^{ii}$)$_2$, wherein each instance of R$^{ii}$ is independently a nitrogen atom substituent described herein, or two instances of R$^{ii}$ are connected to form substituted or unsubstituted heterocyclyl. In certain embodiments, the amino is unsubstituted amino (i.e., —NH$_2$). In certain embodiments, the amino is a substituted amino group, wherein at least one instance of R$^{ii}$ is not hydrogen.

The term "imino" or "imino group" refers to a moiety of the formula: =NR$^{ss}$, wherein R$^{ss}$ is a nitrogen atom substituent described herein.

The term "ketone" or "ketone group" refers to a moiety of the formula: —C(=O)R$^{tt}$, wherein R$^{tt}$ is a carbon atom substituent described herein.

The term "thione" or "thione group" refers to a moiety of the formula: —C(=S)R$^{uu}$, wherein R$^{uu}$ is a carbon atom substituent described herein.

The term "isonitrile" or "isonitrile group" refers to a moiety of the formula: —NC.

The term "isothiocyanide" or "isothiocyanide group" refers to a moiety of the formula: —SNC.

The term "thioate" or "thioate group" refers to a moiety of the formula: —C(=O)SR$^{zz}$ or —C(=S)OR$^{jj}$, wherein R$^{zz}$ is a sulfur atom substituent described herein, and R$^{jj}$ is an oxygen atom substituent described herein.

The term "thioamide" or "thioamide group" refers to a moiety of the formula: —N(R$^{mm}$)C(=S)R$^{nn}$, wherein R$^{mm}$ is a nitrogen atom substituent described herein, and R$^{nn}$ is a carbon atom substituent described herein.

The term "dithioate" or "dithioate group" refers to a moiety of the formula: —C(=S)SR$^{kk}$, wherein R$^{kk}$ is a sulfur atom substituent described herein.

The term "isocyanato" or "isocyanato group" refers to a moiety of the formula: —NCO.

The term "isothiocyanato" or "isothiocyanato group" refers to a moiety of the formula: —NCS.

The term "carbamate" or "carbamate group" refers to a moiety of the formula: —N(R$^{vv}$)C(=O)OR$^{ww}$ or —OC(=O)N(R$^{vv}$)$_2$, wherein each instance of R$^{vv}$ is independently a nitrogen atom substituent described herein, and R$^{ww}$ is an oxygen atom substituent described herein.

The term "urea" or "urea group" refers to a moiety of the formula: —N(R$^{z1}$)C(=O)N(R$^{z1}$)$_2$, wherein each instance of R$^{z1}$ is independently a nitrogen atom substituent described herein.

The term "thiocarbamate" or "thiocarbamate group" refers to a moiety of the formula: —N(R$^{vv}$)C(=S)OR$^{ww}$ or —OC(=S)N(R$^{vv}$)$_2$, —N(R$^{vv}$)C(=O)SR$^{yy}$ or —SC(=O)N(R$^{vv}$)$_2$, wherein each instance of R$^{vv}$ is independently a nitrogen atom substituent described herein, R$^{ww}$ is an oxygen atom substituent described herein, and R$^{yy}$ is a sulfur atom substituent described herein.

"Halo" or "halogen" refers to fluorine (fluoro, F), chlorine (chloro or Cl), bromine (bromo or Br), or iodine (iodo or I).

An atom, moiety, or group described herein may be unsubstituted or substituted, as valency permits, unless otherwise expressly provided. The term "substituted" refers to that at least one hydrogen present on a group (e.g., a carbon or nitrogen atom) is replaced with a permissible substituent, e.g., a substituent which upon substitution results in a stable compound, e.g., a compound which does not spontaneously undergo transformation such as by rearrangement, cyclization, elimination, or other reaction. Unless otherwise indicated, a "substituted" group has a substituent at one or more substitutable positions of the group, and when more than one position in any given structure is substituted, the substituent is either the same or different at each position. The term "substituted" is contemplated to include substitution with all permissible substituents of organic compounds, any of the substituents described herein that results in the formation of a stable compound. The present disclosure contemplates any and all such combinations in order to arrive at a stable compound. For purposes of this disclosure, heteroatoms such as nitrogen may have hydrogen substituents and/or any suitable substituent as described herein which satisfy the valencies of the heteroatoms and results in the formation of a stable moiety. In certain embodiments, the substituent is a carbon atom substituent. In certain embodiments, the substituent is a nitrogen atom substituent. In certain embodiments, the substituent is an oxygen atom substituent. In certain embodiments, the substituent is a sulfur atom substituent. In certain embodiments, a substituent may contribute to optical isomerism and/or stereo isomerism of a compound.

Exemplary carbon atom substituents include, but are not limited to, halogen, —CN, —NO$_2$, —N$_3$, —SO$_2$H, —SO$_3$H, —OH, —OR$^{aa}$, —ON(R$^{bb}$)$_2$, —N(R$^{bb}$)$_2$, —N(R$^{bb}$)$_3$$^+$X$^-$, —N(OR$^{cc}$)R$^{bb}$, —SH, —SR$^{aa}$, —SSR$^{cc}$, —C(=O)R$^{aa}$, —CO$_2$H, —CHO, —C(OR$^{cc}$)$_2$, —CO$_2$R$^{aa}$, —OC(=O)R$^{aa}$, —OCO$_2$R$^{aa}$, —C(=O)N(R$^{bb}$)$_2$, —OC(=O)N(R$^{bb}$)$_2$, —NR$^{bb}$C(=O)R$^{aa}$, —NR$^{bb}$CO$_2$R$^{aa}$, —NR$^{bb}$C(=O)N(R$^{bb}$)$_2$, —C(=NR$^{bb}$)R$^{aa}$, —C(=NR$^{bb}$)OR$^{aa}$, —OC(=NR$^{bb}$)R$^{aa}$, —OC(=NR$^{bb}$)OR$^{aa}$, —C(=NR$^{bb}$)N(R$^{bb}$)$_2$, —OC(=NR$^{bb}$)N(R$^{bb}$)$_2$, NR$^{bb}$C(=NR$^{bb}$)N(R$^{bb}$)$_2$, —C(=O)NR$^{bb}$SO$_2$R$^{aa}$, —NR$^{bb}$SO$_2$R$^{aa}$, —SO$_2$N(R$^{bb}$)$_2$, —SO$_2$R$^{aa}$, —SO$_2$OR$^{aa}$, —OSO$_2$R$^{aa}$, —S(=O)R$^{aa}$, —OS(=O)R$^{aa}$, —Si(R$^{aa}$)$_3$, —OSi(R$^{aa}$)$_3$—C(=S)N(R$^{bb}$)$_2$, —C(=O)SR$^{aa}$, —C(=S)SR$^{aa}$, —SC(=S)SR$^{aa}$, —SC(=O)SR$^{aa}$, —OC(=O)SR$^{aa}$, —SC(=O)OR$^{aa}$, —SC(=O)R$^{aa}$, —P(=O)$_2$R$^{aa}$, —OP(=O)$_2$R$^{aa}$, —P(=O)(R$^{aa}$)$_2$, —OP(=O)(R$^{aa}$)$_2$, —OP(=O)(OR$^{cc}$)$_2$, —P(=O)$_2$N(R$^{bb}$)$_2$, —OP(=O)$_2$N(R$^{bb}$), —P(=O)(NR$^{bb}$)$_2$, —OP(=O)(NR$^{bb}$)$_2$, —NR$^{bb}$P(=O)(OR$^{cc}$)$_2$, —NR$^{bb}$P(=O)(NR$^{bb}$)$_2$, —P(R$^{cc}$)$_2$, —P(R$^{cc}$)$_3$, —OP(R$^{cc}$)$_2$, —OP(R$^{cc}$)$_3$, —B(R$^{cc}$)$_2$, —B(OR$^{cc}$)$_2$, —BR$^{aa}$(OR$^{cc}$), C$_{1-10}$ alkyl, C$_{1-10}$ perhaloalkyl, C$_{2-10}$ alkenyl, C$_{2-10}$ alkynyl, C$_{3-10}$ carbocyclyl, 3-14 membered heterocyclyl, C$_{6-14}$ aryl, and 5-14 membered heteroaryl, wherein each alkyl, alkenyl, alkynyl, carbocyclyl, heterocyclyl, aryl, and heteroaryl is independently substituted with 0, 1, 2, 3, 4, or 5 R$^{dd}$ groups; or two geminal hydrogens on a carbon atom are replaced with the group =O, =S, =NN(R$^{bb}$)$_2$, =NNR$^{bb}$C(=O)R$^{aa}$, =NNR$^{bb}$C(=O)OR$^{aa}$, =NNR$^{bb}$S(=O)$_2$R$^{aa}$, =NR$^{bb}$, or =NOR$^{cc}$, each instance of R$^{aa}$ is, independently, selected from C$_{1-10}$ alkyl, C$_{1-10}$ perhaloalkyl, C$_{2-10}$ alkenyl, C$_{2-10}$ alkynyl, C$_{3-10}$ carbocyclyl, 3-14 membered heterocyclyl, C$_{6-14}$ aryl, and 5-14 membered heteroaryl, or two R$^{aa}$ groups are joined to form a 3-14 membered heterocyclyl or 5-14 membered heteroaryl ring, wherein each alkyl, alkenyl, alkynyl, carbocyclyl, heterocyclyl, aryl, and heteroaryl is independently substituted with 0, 1, 2, 3, 4, or 5 Rd groups;

each instance of R$^{bb}$ is, independently, selected from hydrogen, —OH, —OR$^{aa}$, —N(R$^{cc}$)$_2$, —CN, —C(=O)R$^{aa}$, —C(=O)N(R$^{cc}$)$_2$, —CO$_2$R$^{aa}$, —SO$_2$R$^{aa}$, —C(=NR$^{cc}$)OR$^{aa}$, —C(=NR$^{cc}$)N(R$^{cc}$)$_2$, —SO$_2$N(R$^{cc}$)$_2$, —SO$_2$R$^{cc}$, —SO$_2$OR$^{cc}$, —SOR$^{aa}$, —C(=S)N(R$^{cc}$)$_2$, —C(=O)SR$^{cc}$, —C(=S)SR$^{cc}$, —P(=O)$_2$R$^{aa}$, —P(=O)(R$^{aa}$)$_2$, —P(=O)$_2$N(R$^{cc}$)$_2$, —P(=O)(NR$^{cc}$)$_2$, C$_{1-10}$ alkyl, C$_{1-10}$ perhaloalkyl, C$_{2-10}$ alkenyl, C$_{2-10}$ to alkynyl, C$_{3-10}$ carbocyclyl, 3-14 membered heterocyclyl, C$_{6-14}$ aryl, and 5-14 membered heteroaryl, or two R$^{bb}$ groups are joined to form a 3-14 membered heterocyclyl or 5-14 membered heteroaryl ring, wherein each alkyl, alkenyl, alkynyl, carbocyclyl, heterocyclyl, aryl, and heteroaryl is independently substituted with 0, 1, 2, 3, 4, or 5 R$^{dd}$ groups;

each instance of R$^{cc}$ is, independently, selected from hydrogen, C$_{1-10}$ alkyl, C$_{1-10}$ perhaloalkyl, C$_{2-10}$ alkenyl, C$_{2-10}$ alkynyl, C$_{3-10}$ carbocyclyl, 3-14 membered heterocyclyl, C$_{6-14}$ aryl, and 5-14 membered heteroaryl, or two R$^{cc}$ groups are joined to form a 3-14 membered heterocyclyl or 5-14 membered heteroaryl ring, wherein each alkyl, alkenyl, alkynyl, carbocyclyl, heterocyclyl, aryl, and heteroaryl is independently substituted with 0, 1, 2, 3, 4, or 5 R$^{dd}$ groups; each instance of R$^{dd}$ is, independently, selected from halogen, —CN, —NO$_2$, —N$_3$, —SO$_2$H, —SO$_3$H, —OH, —OR$^{ee}$, —ON(R$^{ff}$)$_2$, —N(R$^{ff}$)$_2$, —N(R$^{ff}$)$_3$$^+$X$^-$, —N(OR$^{ee}$)R$^{ff}$, —SH, —SR$^{ee}$, —SSR$^{ee}$, —C(=O)R$^{ee}$, —CO$_2$H, —CO$_2$R$^{ee}$, —OC(=O)R$^{ee}$, —OCO$_2$R$^{ee}$, —C(=O)N(R$^{ff}$)$_2$, —OC(=O)N(R$^{ff}$)$_2$, —NR$^{ff}$C(=O)R$^{ee}$, —NR$^{ff}$CO$_2$R$^{ee}$, —NR$^{ff}$C(=O)N(R$^{ff}$)$_2$, —C(=NR)OR$^{ee}$, —OC(=NR)R$^{ee}$, —OC(=NR$^{ff}$)OR$^{ee}$, —C(=NR$^{ff}$)N(R$^{ff}$)$_2$, —OC(=NR$^{ff}$)N(R$^{ff}$)$_2$, —NR$^{ff}$C(=NR$^{ff}$)N(R$^{ff}$)$_2$, —NR$^{ff}$SO$_2$R$^{ee}$, —SO$_2$N(R$^{ff}$)$_2$, —SO$_2$R$^{ee}$, —SO$_2$OR$^{ee}$, —OSO$_2$R$^{ee}$, —S(=O)R$^{ee}$, —Si(R$^{ee}$)$_3$, —OSi(R$^{ee}$)$_3$, —C(=S)N(R$^{ff}$)$_2$, —C(=O)SR$^{ee}$, —C(=S)SR$^{ee}$, —SC(=S)SR$^{ee}$, —P(=O)$_2$R$^{ee}$, —P(=O)(R$^{ee}$)$_2$, —OP(=O)(R$^{ee}$)$_2$, —OP(=O)(OR$^{ee}$)$_2$, C$_{1-6}$ alkyl, C$_{1-10}$ perhaloalkyl, C$_{2-6}$ alkenyl, C$_{2-6}$ alkynyl, C$_{3-10}$ carbocyclyl, 3-10 membered heterocyclyl, C$_{6-10}$ aryl, 5-10 membered heteroaryl, wherein each alkyl, alkenyl, alkynyl, carbocyclyl, heterocyclyl, aryl, and heteroaryl is independently substituted with 0, 1, 2, 3, 4, or 5 R$^{gg}$ groups, or two geminal R$^{dd}$ substituents can be joined to form =O or =S;

each instance of R$^{ee}$ is, independently, selected from C$_{1-6}$ alkyl, C$_{1-6}$ perhaloalkyl, C$_{2-6}$ alkenyl, C$_{2-6}$ alkynyl, C$_{3-10}$ carbocyclyl, C$_{6-10}$ aryl, 3-10 membered heterocyclyl, and 3-10 membered heteroaryl, wherein each alkyl, alkenyl, alkynyl, carbocyclyl, heterocyclyl, aryl, and heteroaryl is independently substituted with 0, 1, 2, 3, 4, or 5 R$^{gg}$ groups;

each instance of R$^{ff}$ is, independently, selected from hydrogen, C$_{1-6}$ alkyl, C$_{1-6}$ perhaloalkyl, C$_{2-6}$ alkenyl, C$_{2-6}$ alkynyl, C$_{3-10}$ carbocyclyl, 3-10 membered heterocyclyl, C$_{6-10}$ aryl and 5-10 membered heteroaryl, or two R$^{ff}$ groups are joined to form a 3-14 membered heterocyclyl or 5-14 membered heteroaryl ring, wherein each alkyl, alkenyl, alkynyl, carbocyclyl, heterocyclyl, aryl, and heteroaryl is independently substituted with 0, 1, 2, 3, 4, or 5 R$^{gg}$ groups; and each instance of R$^{gg}$ is, independently, halogen, —CN, —NO$_2$, —N$_3$, —SO$_2$H, —SO$_3$H, —OH, —OC$_{1-6}$ alkyl, —ON(C$_{1-6}$ alkyl)$_2$, —N(C$_{1-6}$ alkyl)$_2$, —N(C$_{1-6}$ alkyl)$_3$$^+$X$^-$, —NH(C$_{1-6}$ alkyl)$_2$$^+$X$^-$, —NH$_2$(C$_{1-6}$ alkyl)$^+$X$^-$, —NH$_3$$^+$X$^-$, —N(OC$_{1-6}$ alkyl)(C$_{1-6}$ alkyl), —N(OH)(C$_{1-6}$ alkyl), —NH(OH), —SH, —SC$_{1-6}$ alkyl, —SS(C$_{1-6}$ alkyl), —C(=O)(C$_{1-6}$ alkyl), —CO$_2$H, —CO$_2$(C$_{1-6}$ alkyl), —OC(=O)(C$_{1-6}$ alkyl), —OCO$_2$(C$_{1-6}$ alkyl), —C(=O)NH$_2$, —C(=O)N(C$_{1-6}$ alkyl)$_2$, —OC(=O)NH(C$_{1-6}$ alkyl), —NHC(=O)(C$_{1-6}$ alkyl), —N(C$_{1-6}$ alkyl)C(=O)(C$_{1-6}$ alkyl), —NHCO$_2$(C$_{1-6}$ alkyl), —NHC(=O)N($C_{1-6}$ alkyl)$_2$, —NHC(=O)NH($C_{1-6}$ alkyl), —NHC(=O)NH$_2$, —C(=NH)O($C_{1-6}$ alkyl), —OC(=NH)($C_{1-6}$ alkyl), —OC(=NH)O$C_{1-6}$ alkyl, —C(=NH)N($C_{1-6}$ alkyl)$_2$, —C(=NH)NH($C_{1-6}$ alkyl), —C(=NH)NH$_2$, —OC(=NH)N($C_{1-6}$ alkyl)$_2$, —OC(NH)NH($C_{1-6}$ alkyl), —OC(NH)NH$_2$, —NHC(NH)N($C_{1-6}$ alkyl)$_2$, —NHC(=NH)NH$_2$, —NHSO$_2$($C_{1-6}$ alkyl), —SO$_2$N($C_{1-6}$ alkyl)$_2$, —SO$_2$NH($C_{1-6}$ alkyl), —SO$_2$NH$_2$, —SO$_2$$C_{1-6}$ alkyl, —SO$_2$O$C_{1-6}$ alkyl, —OSO$_2$$C_{1-6}$ alkyl, —SO$C_{1-6}$ alkyl, —Si($C_{1-6}$ alkyl)$_3$, —OSi($C_{1-6}$ alkyl)$_3$-C(=S)N($C_{1-6}$ alkyl)$_2$, C(=S)NH($C_{1-6}$ alkyl), C(=S)NH$_2$, —C(=O)S($C_{1-6}$ alkyl), —C(=S)S$C_{1-6}$ alkyl, —SC(=S)S$C_{1-6}$ alkyl, —P(=O)$_2$ ($C_{1-6}$ alkyl), —P(=O)($C_{1-6}$ alkyl)$_2$, —OP(=O)($C_{1-6}$ alkyl)$_2$, —OP(=O)(O$C_{1-6}$ alkyl)$_2$, $C_{1-6}$ alkyl, $C_{1-6}$ perhaloalkyl, $C_{2-6}$ alkenyl, $C_{2-6}$ alkynyl, $C_{3-10}$carbocyclyl, $C_{6-10}$ aryl, 3-10 membered heterocyclyl, 5-10 membered heteroaryl; or two geminal $R^{gg}$ substituents can be joined to form =O or =S; wherein $X^-$ is a counterion.

A "counterion" or "anionic counterion" is a negatively charged group associated with a cationic quaternary amino group in order to maintain electronic neutrality. Exemplary counterions include halide ions (e.g., $F^-$, $Cl^-$, $Br^-$, $F^-$), $NO_3^-$, $ClO_4^-$, $OH^-$, $H_2PO_4^-$, $HSO_4^-$, sulfonate ions (e.g., methansulfonate, trifluoromethanesulfonate, p-toluenesulfonate, benzenesulfonate, 10-camphor sulfonate, naphthalene-2-sulfonate, naphthalene-1-sulfonic acid-5-sulfonate, ethan-1-sulfonic acid-2-sulfonate, and the like), and carboxylate ions (e.g., acetate, ethanoate, propanoate, benzoate, glycerate, lactate, tartrate, and glycolate).

Nitrogen atoms can be substituted or unsubstituted as valency permits, and include primary, secondary, tertiary, and quarternary nitrogen atoms. Exemplary nitrogen atom substituents include, but are not limited to, hydrogen, —OH, —OR$^{aa}$, —N(R$^{cc}$)$_2$, —CN, —C(=O)R$^{aa}$, —C(=O)N(R$^{cc}$)$_2$, —CO$_2$R$^{aa}$, —SO$_2$R$^{aa}$, —C(=NR$^{bb}$)R$^{aa}$, —C(=NR$^{cc}$)OR$^{aa}$, —C(=NR$^{cc}$)N(R$^{cc}$)$_2$, —SO$_2$N(R$^{cc}$)$_2$, —SO$_2$R$^{cc}$, —SO$_2$OR$^{cc}$, —SOR$^{aa}$, —C(=S)N(R$^{cc}$)$_2$, —C(=O)SR$^{cc}$, —C(=S)SR$^{cc}$, —P(=O)$_2$R$^{aa}$, —P(=O)(R$^{aa}$)$_2$, —P(=O)$_2$N(R$^{cc}$)$_2$, —P(=O)(NR$^{cc}$)$_2$, $C_{1-10}$ alkyl, $C_{1-10}$ perhaloalkyl, $C_{2-10}$ alkenyl, $C_{2-10}$ alkynyl, $C_{3-10}$ carbocyclyl, 3-14 membered heterocyclyl, $C_{6-14}$ aryl, and 5-14 membered heteroaryl, or two R$^{cc}$ groups attached to a nitrogen atom are joined to form a 3-14 membered heterocyclyl or 5-14 membered heteroaryl ring, wherein each alkyl, alkenyl, alkynyl, carbocyclyl, heterocyclyl, aryl, and heteroaryl is independently substituted with 0, 1, 2, 3, 4, or 5 R$^{dd}$ groups, and wherein R$^{aa}$, R$^{bb}$, R$^{cc}$, and R$_{dd}$ are as defined herein.

In certain embodiments, the substituent present on a nitrogen atom is a nitrogen protecting group (also referred to as an amino protecting group). Nitrogen protecting groups include, but are not limited to, —OH, —OR$^{aa}$, —N(R$_{cc}$)$_2$, —C(O)R$^{aa}$, —C(=O)N(R$^{cc}$)$_2$, —CO$_2$R$^{aa}$, —SO$_2$R$^{aa}$, —C(=NR$^{cc}$)R$^{aa}$, —C(=NR$^{cc}$)OR$^{aa}$, —C(=NR$^{cc}$)N(R$^{cc}$)$_2$, —SO$_2$N(R$^{cc}$)$_2$, —SO$_2$R$^{cc}$, —SO$_2$OR$^{cc}$, —SOR$^{aa}$, —C(=S)N(R$^{cc}$)$_2$, —C(=O)SR$^{cc}$, —C(=S)SR$^{cc}$, $C_{1-10}$ alkyl (e.g., aralkyl, heteroaralkyl), $C_{2-10}$ alkenyl, $C_{2-10}$ alkynyl, $C_{3-10}$ carbocyclyl, 3-14 membered heterocyclyl, $C_{6-14}$ aryl, and 5-14 membered heteroaryl groups, wherein each alkyl, alkenyl, alkynyl, carbocyclyl, heterocyclyl, aralkyl, aryl, and heteroaryl is independently substituted with 0, 1, 2, 3, 4, or 5 R$^{dd}$ groups, and wherein R$^{aa}$, R$^{bb}$, R$^{cc}$ and R$^{dd}$ are as defined herein. Nitrogen protecting groups are well known in the art and include those described in detail in *Protecting Groups in Organic Synthesis*, T. W. Greene and P. G. M. Wuts, 3$^{rd}$ edition, John Wiley & Sons, 1999, incorporated herein by reference.

For example, nitrogen protecting groups include, but are not limited to, formamide, acetamide, chloroacetamide, trichloroacetamide, trifluoroacetamide, phenylacetamide, 3-phenylpropanamide, picolinamide, 3-pyridylcarboxamide, N-benzoylphenylalanyl derivative, benzamide, p-phenylbenzamide, o-nitophenylacetamide, o-nitrophenoxyacetamide, acetoacetamide, (N'-dithiobenzyloxyacylamino)acetamide, 3-(p-hydroxyphenyl)propanamide, 3-(o-nitrophenyl)propanamide, 2-methyl-2-(o-nitrophenoxy)propanamide, 2-methyl-2-(o-phenylazophenoxy)propanamide, 4-chlorobutanamide, 3-methyl-3-nitrobutanamide, o-nitrocinnamide, N-acetylmethionine derivative, o-nitrobenzamide, and o-(benzoyloxymethyl)benzamide.

Nitrogen protecting groups also include, but are not limited to, methyl carbamate, ethyl carbamante, 9-fluorenylmethyl carbamate (Fmoc), 9-(2-sulfo)fluorenylmethyl carbamate, 9-(2,7-dibromo)fluoroenylmethyl carbamate, 2,7-di-t-butyl-[9-(10,10-dioxo-10,10,10,10-tetrahydrothioxanthyl)]methyl carbamate (DBD-Tmoc), 4-methoxyphenacyl carbamate (Phenoc), 2,2,2-trichloroethyl carbamate (Troc), 2-trimethylsilylethyl carbamate (Teoc), 2-phenylethyl carbamate (hZ), 1-(1-adamantyl)-1-methylethyl carbamate (Adpoc), 1,1-dimethyl-2-haloethyl carbamate, 1,1-dimethyl-2,2-dibromoethyl carbamate (DB-t-BOC), 1,1-dimethyl-2,2,2-trichloroethyl carbamate (TCBOC), 1-methyl-1-(4-biphenylyl)ethyl carbamate (Bpoc), 1-(3,5-di-t-butylphenyl)-1-methylethyl carbamate (t-Bumeoc), 2-(2'- and 4'-pyridyl)ethyl carbamate (Pyoc), 2-(N,N-dicyclohexylcarboxamido)ethyl carbamate, t-butyl carbamate (BOC), 1-adamantyl carbamate (Adoc), vinyl carbamate (Voc), allyl carbamate (Alloc), 1-isopropylallyl carbamate (Ipaoc), cinnamyl carbamate (Coc), 4-nitrocinnamyl carbamate (Noc), 8-quinolyl carbamate, N-hydroxypiperidinyl carbamate, alkyldithio carbamate, benzyl carbamate (Cbz), p-methoxybenzyl carbamate (Moz), p-nitobenzyl carbamate, p-bromobenzyl carbamate, p-chlorobenzyl carbamate, 2,4-dichlorobenzyl carbamate, 4-methylsulfinylbenzyl carbamate (Msz), 9-anthrylmethyl carbamate, diphenylmethyl carbamate, 2-methylthioethyl carbamate, 2-methylsulfonylethyl carbamate, 2-(p-toluenesulfonyl)ethyl carbamate, [2-(1,3-dithianyl)]methyl carbamate (Dmoc), 4-methylthiophenyl carbamate (Mtpc), 2,4-dimethylthiophenyl carbamate (Bmpc), 2-phosphonioethyl carbamate (Peoc), 2-triphenylphosphonioisopropyl carbamate (Ppoc), 1,1-dimethyl-2-cyanoethyl carbamate, m-chloro-p-acyloxybenzyl carbamate, p-(dihydroxyboryl)benzyl carbamate, 5-benzisoxazolylmethyl carbamate, 2-(trifluoromethyl)-6-chromonylmethyl carbamate (Tcroc), m-nitrophenyl carbamate, 3,5-dimethoxybenzyl carbamate, o-nitrobenzyl carbamate, 3,4-dimethoxy-6-nitrobenzyl carbamate, phenyl(o-nitrophenyl)methyl carbamate, t-amyl carbamate, S-benzyl thiocarbamate, p-cyanobenzyl carbamate, cyclobutyl carbamate, cyclohexyl carbamate, cyclopentyl carbamate, cyclopropylmethyl carbamate, p-decyloxybenzyl carbamate, 2,2-dimethoxyacylvinyl carbamate, o-(N,N-dimethylcarboxamido)benzyl carbamate, 1,1-dimethyl-3-(N,N-dimethylcarboxamido)propyl carbamate, 1,1-dimethylpropynyl carbamate, di(2-pyridyl)methyl carbamate, 2-furanylmethyl carbamate, 2-iodoethyl carbamate, isoborynl carbamate, isobutyl carbamate, isonicotinyl carbamate, p-(p'-methoxyphenylazo)benzyl carbamate, 1-methylcyclobutyl carbamate, 1-methylcyclohexyl carbamate, 1-methyl-1-cyclopropylmethyl carbamate, 1-methyl-1-(3,5-dimethoxyphenyl)ethyl carbamate, 1-methyl-1-(p-phenylazophenyl)ethyl carbamate, 1-methyl-1-phenylethyl carbamate, 1-methyl-1-(4-pyridyl)ethyl carbamate, phenyl carbamate, p-(phenylazo)benzyl carbamate, 2,4,6-tri-t-butylphenyl carbamate, 4-(trimethylammonium)benzyl carbamate, and 2,4,6-trimethylbenzyl carbamate.

Nitrogen protecting groups further include, but are not limited to, p-toluenesulfonamide (Ts), benzenesulfonamide, 2,3,6-trimethyl-4-methoxybenzenesulfonamide (Mtr), 2,4,6-trimethoxybenzenesulfonamide (Mtb), 2,6-dimethyl-4-methoxybenzenesulfonamide (Pme), 2,3,5,6-tetramethyl-4-methoxybenzenesulfonamide (Mte), 4-methoxybenzenesulfonamide (Mbs), 2,4,6-trimethylbenzenesulfonamide (Mts), 2,6-dimethoxy-4-methylbenzenesulfonamide (iMds), 2,2,5,7,8-pentamethylchroman-6-sulfonamide (Pmc), methanesulfonamide (Ms), β-trimethylsilylethanesulfonamide (SES), 9-anthracenesulfonamide, 4-(4',8'-dimethoxynaphthylmethyl)benzenesulfonamide (DNMBS), benzylsulfonamide, trifluoromethylsulfonamide, and phenacylsulfonamide.

Other nitrogen protecting groups include, but are not limited to, phenothiazinyl-(10)-acyl derivative, N'-p-toluenesulfonylaminoacyl derivative, N'-phenylaminothioacyl derivative, N-benzoylphenylalanyl derivative, N-acetylmethionine derivative, 4,5-diphenyl-3-oxazolin-2-one, N-phthalimide, N-dithiasuccinimide (Dts), N-2,3-diphenylmaleimide, N-2,5-dimethylpyrrole, N-1,1,4,4-tetramethyldisilylazacyclopentane adduct (STABASE), 5-substituted 1,3-dimethyl-1,3,5-triazacyclohexan-2-one, 5-substituted 1,3-dibenzyl-1,3,5-triazacyclohexan-2-one, 1-substituted 3,5-dinitro-4-pyridone, N-methylamine, N-allylamine, N-[2-(trimethylsilyl)ethoxy]methylamine (SEM), N-3-acetoxypropylamine, N-(1-isopropyl-4-nitro-2-oxo-3-pyroolin-3-yl)amine, quaternary ammonium salts, N-benzylamine, N-di(4-methoxyphenyl)methylamine, N-5-dibenzosuberylamine, N-triphenylmethylamine (Tr), N-[(4-methoxyphenyl)diphenylmethyl]amine (MMTr), N-9-phenylfluorenylamine (PhF), N-2,7-dichloro-9-fluorenylmethyleneamine, N-ferrocenylmethylamino (Fcm), N-2-picolylamino N'-oxide, N-1,1-dimethylthiomethyleneamine, N-benzylideneamine, N-p-methoxybenzylideneamine, N-diphenylmethyleneamine, N-[(2-pyridyl)mesityl]methyleneamine, N—(N',N'-dimethylaminomethylene)amine, N,N'-isopropylidenediamine, N-p-nitrobenzylideneamine, N-salicylideneamine, N-5-chlorosalicylideneamine, N-(5-chloro-2-hydroxyphenyl)phenylmethyleneamine, N-cyclohexylideneamine, N-(5,5-dimethyl-3-oxo-1-cyclohexenyl)amine, N-borane derivative, N-diphenylborinic acid derivative, N-[phenyl(pentaacylchromium- or tungsten)acyl]amine, N-copper chelate, N-zinc chelate, N-nitroamine, N-nitrosoamine, amine N-oxide, diphenylphosphinamide (Dpp), dimethylthiophosphinamide (Mpt), diphenylthiophosphinamide (Ppt), dialkyl phosphoramidates, dibenzyl phosphoramidate, diphenyl phosphoramidate, benzenesulfenamide, o-nitrobenzenesulfenamide (Nps), 2,4-dinitrobenzenesulfenamide, pentachlorobenzenesulfenamide, 2-nitro-4-methoxybenzenesulfenamide, triphenylmethylsulfenamide, and 3-nitropyridinesulfenamide (Npys).

Exemplary oxygen atom substituents include, but are not limited to, —$R^{aa}$, —$C(=O)SR^{aa}$, —$C(=O)R^{aa}$, —$CO_2R^{aa}$, —$C(=O)N(R^{bb})_2$, —$C(=NR^{bb})R^{aa}$, —$C(=NR^{bb})OR^{aa}$, —$C(=NR^{bb})N(R^{bb})_2$, —$S(=O)R^{aa}$, —$SO_2R^{aa}$, —$Si(R^{aa})_3$, —$P(R^{cc})_2$, —$P(R^{cc})_3$, —$P(=O)_2R^{aa}$, —$P(=O)(R^{aa})_2$, —$P(=O)(OR^{cc})$, —$P(=O)_2N(R^{bb})_2$, and —$P(=O)(NR^{bb})_2$, wherein $R^{aa}$, $R^{bb}$, and $R^{cc}$ are as defined herein. In certain embodiments, the oxygen atom substituent present on an oxygen atom is an oxygen protecting group (also referred to as a hydroxyl protecting group). Oxygen protecting groups are well known in the art and include those described in detail in *Protecting Groups in Organic Synthesis*, T. W. Greene and P. G. M. Wuts, $3^{rd}$ edition, John Wiley & Sons, 1999, incorporated herein by reference. Exemplary oxygen protecting groups include, but are not limited to, methyl, t-butyloxycarbonyl (BOC or Boc), methoxylmethyl (MOM), methylthiomethyl (MTM), t-butylthiomethyl, (phenyldimethylsilyl)methoxymethyl (SMOM), benzyloxymethyl (BOM), p-methoxybenzyloxymethyl (PMBM), (4-methoxyphenoxy)methyl (p-AOM), guaiacolmethyl (GUM), t-butoxymethyl, 4-pentenyloxymethyl (POM), siloxymethyl, 2-methoxyethoxymethyl (MEM), 2,2,2-trichloroethoxymethyl, bis(2-chloroethoxy)methyl, 2-(trimethylsilyl)ethoxymethyl (SEMOR), tetrahydropyranyl (THP), 3-bromotetrahydropyranyl, tetrahydrothiopyranyl, 1-methoxycyclohexyl, 4-methoxytetrahydropyranyl (MTHP), 4-methoxytetrahydrothiopyranyl, 4-methoxytetrahydrothiopyranyl S,S-dioxide, 1-[(2-chloro-4-methyl)phenyl]-4-methoxypiperidin-4-yl (CTMP), 1,4-dioxan-2-yl, tetrahydrofuranyl, tetrahydrothiofuranyl, 2,3,3a,4,5,6,7,7a-octahydro-7,8,8-trimethyl-4,7-methanobenzofuran-2-yl, 1-ethoxyethyl, 1-(2-chloroethoxy)ethyl, 1-methyl-1-methoxyethyl, 1-methyl-1-benzyloxyethyl, 1-methyl-1-benzyloxy-2-fluoroethyl, 2,2,2-trichloroethyl, 2-trimethylsilylethyl, 2-(phenylselenyl)ethyl, t-butyl, allyl, p-chlorophenyl, p-methoxyphenyl, 2,4-dinitrophenyl, benzyl (Bn), p-methoxybenzyl, 3,4-dimethoxybenzyl, o-nitrobenzyl, p-nitrobenzyl, p-halobenzyl, 2,6-dichlorobenzyl, p-cyanobenzyl, p-phenylbenzyl, 2-picolyl, 4-picolyl, 3-methyl-2-picolyl N-oxido, diphenylmethyl, p,p'-dinitrobenzhydryl, 5-dibenzosuberyl, triphenylmethyl, a-naphthyldiphenylmethyl, p-methoxyphenyldiphenylmethyl, di(p-methoxyphenyl)phenylmethyl, tri(p-methoxyphenyl)methyl, 4-(4'-bromophenacyloxyphenyl)diphenylmethyl, 4,4',4''-tris(4,5-dichlorophthalimidophenyl)methyl, 4,4',4''-tris(levulinoyloxyphenyl)methyl, 4,4',4''-tris(benzoyloxyphenyl)methyl, 3-(imidazol-1-yl)bis(4',4''-dimethoxyphenyl)methyl, 1,1-bis(4-methoxyphenyl)-1'-pyrenylmethyl, 9-anthryl, 9-(9-phenyl)xanthenyl, 9-(9-phenyl-10-oxo)anthryl, 1,3-benzodisulfuran-2-yl, benzisothiazolyl S,S-dioxido, trimethylsilyl (TMS), triethylsilyl (TES), triisopropylsilyl (TIPS), dimethylisopropylsilyl (IPDMS), diethylisopropylsilyl (DEIPS), dimethylthexylsilyl, t-butyldimethylsilyl (TBDMS), t-butyldiphenylsilyl (TBDPS), tribenzylsilyl, tri-p-xylylsilyl, triphenylsilyl, diphenylmethylsilyl (DPMS), t-butylmethoxyphenylsilyl (TBMPS), formate, benzoylformate, acetate, chloroacetate, dichloroacetate, trichloroacetate, trifluoroacetate, methoxyacetate, triphenylmethoxyacetate, phenoxyacetate, p-chlorophenoxyacetate, 3-phenylpropionate, 4-oxopentanoate (levulinate), 4,4-(ethylenedithio)pentanoate (levulinoyldithioacetal), pivaloate, adamantoate, crotonate, 4-methoxycrotonate, benzoate, p-phenylbenzoate, 2,4,6-trimethylbenzoate (mesitoate), alkyl methyl carbonate, 9-fluorenylmethyl carbonate (Fmoc), alkyl ethyl carbonate, alkyl 2,2,2-trichloroethyl carbonate (Troc), 2-(trimethylsilyl)ethyl carbonate (TMSEC), 2-(phenylsulfonyl)ethyl carbonate (Psec), 2-(triphenylphosphonio)ethyl carbonate (Peoc), alkyl isobutyl carbonate, alkyl vinyl carbonate alkyl allyl carbonate, alkyl p-nitrophenyl carbonate, alkyl benzyl carbonate, alkyl p-methoxybenzyl carbonate, alkyl 3,4-dimethoxybenzyl carbonate, alkyl o-nitrobenzyl carbonate, alkyl p-nitrobenzyl carbonate, alkyl S-benzyl thiocarbonate, 4-ethoxy-1-napthyl carbonate, methyl dithiocarbonate, 2-iodobenzoate, 4-azidobutyrate, 4-nitro-4-methylpentanoate, o-(dibromomethyl)benzoate, 2-formylbenzenesulfonate, 2-(methylthiomethoxy)ethyl, 4-(methylthiomethoxy)butyrate, 2-(methylthiomethoxymethyl)benzoate, 2,6-dichloro-4-methylphenoxyacetate, 2,6-dichloro-4-(1,1,3,3-tetramethylbutyl)phenoxyacetate, 2,4-bis(1,1-dimethylpropyl)phenoxyacetate, chlorodiphenylacetate, isobutyrate, monosuccinoate, (E)-2-methyl-2-butenoate, o-(methoxyacyl)benzoate, α-naphthoate, nitrate, alkyl N,N,N',N'-tetramethylphosphorodiamidate, alkyl N-phenylcarbamate, borate, dimethylphosphinothioyl, alkyl 2,4-dinitrophenylsulfenate, sulfate, methanesulfonate (mesylate), benzylsulfonate, and tosylate (Ts).

Exemplary sulfur atom substituents include, but are not limited to, —$R^{aa}$, —C(=O)$SR^{aa}$, —C(=O)$R^{aa}$, —$CO_2R^{aa}$, —C(=O)N($R^{bb}$)$_2$, —C(=$NR^{bb}$)$R^{aa}$, —C(=$NR^{bb}$)$OR^{aa}$, —C(=$NR^{bb}$)N($R^{bb}$)$_2$, —S(=O)$R^{aa}$, —$SO_2R^{aa}$, —Si($R^{aa}$)$_3$, —P($R^{cc}$)$_2$, —P($R^{cc}$)$_3$, —P(=O)$_2R^{aa}$, —P(=O)($R^{aa}$)$_2$, —P(=O)($OR^{cc}$)$_2$, —P(=O)$_2$N($R^{bb}$)$_2$, and —P(=O)(N$R^{bb}$)$_2$, wherein $R^{aa}$, $R^{bb}$, and $R^{cc}$ are as defined herein. In certain embodiments, the sulfur atom substituent present on a sulfur atom is a sulfur protecting group (also referred to as a thiol protecting group). Sulfur protecting groups are well known in the art and include those described in detail in *Protecting Groups in Organic Synthesis*, T. W. Greene and P. G. M. Wuts, 3$^{rd}$ edition, John Wiley & Sons, 1999, incorporated herein by reference.

The compound represented by compound name "RJn" is the same as the compound represent by compound name "RJ-n", wherein n is an integer between 1 and 100, inclusive.

An exemplary process for preparing compounds of Formula (I) (e.g., a compound of Formula (I-A) or (I-B)) is described as follows. A compound of Formula (I) may be prepared according to Scheme 1:

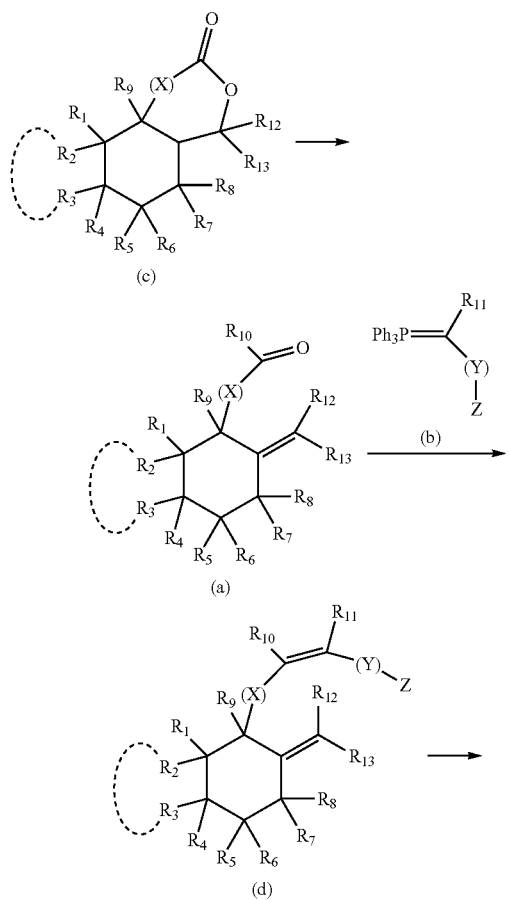

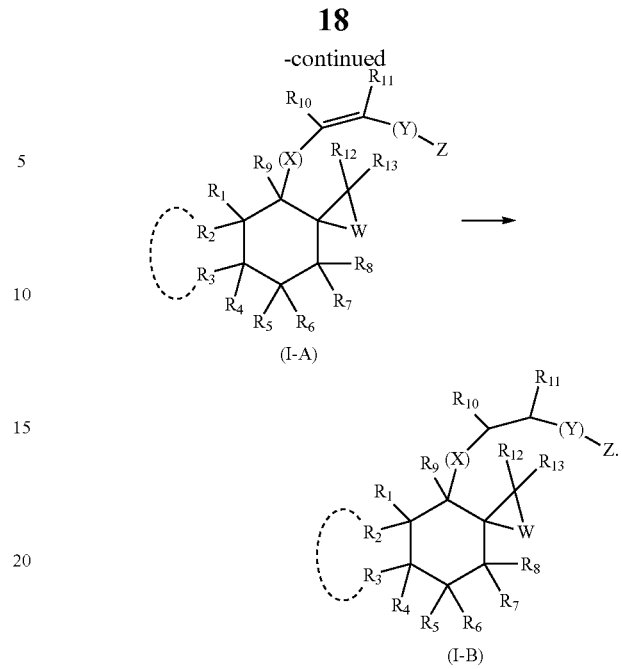

A compound of Formula (a) may be prepared from a compound of Formula (c), which may be a natural product and/or commercially available, and/or may be readily prepared according to methods known in the art. A compound of Formula (a) may be reacted with a compound of Formula (b) to form a compound of Formula (d), which includes a C=C double bond between the two carbon atoms directly bonded with $R_{10}$ and $R_{11}$, respectively. The C=C double bond directly on the cyclohexyl ring and directly bonded with $R_{12}$ and $R_{13}$ of a compound of Formula (d) may be converted to a 3-membered ring

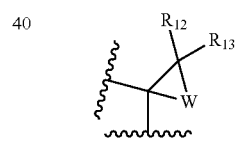

to give a compound of Formula (I-A). A compound of Formula (I-A) may be hydrogenated to yield a compound of Formula (I-B).

Galanal or a galanal analogue may be prepared by cyclizing a compound of Formula (I) (e.g., a compound of Formula (I-A) or (I-B)) to form a compound of Formula (II):

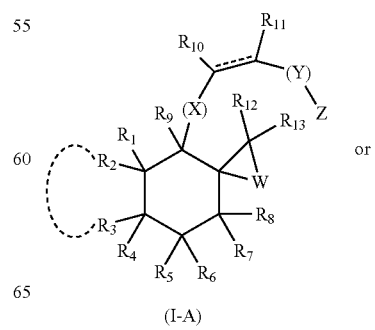

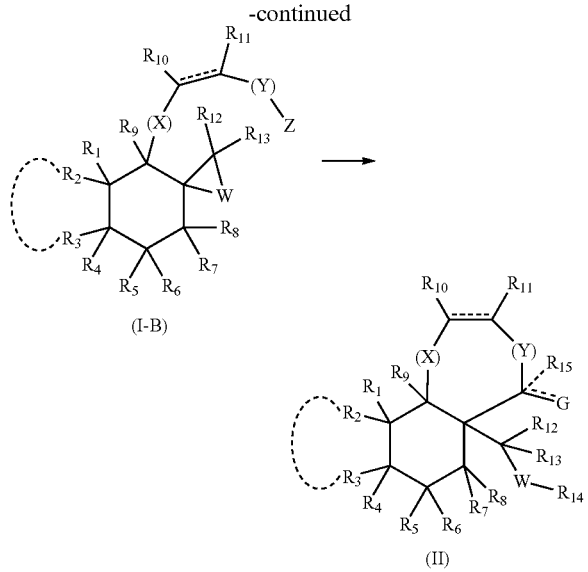

wherein:

R$_{14}$ is hydrogen or a saturated or unsaturated, substituted or unsubstituted, branched or unbranched, (hetero)aliphatic group having 1-16 carbon atoms;

R$_{15}$ is hydrogen, or a saturated or unsaturated, substituted or unsubstituted, branched or unbranched, (hetero)aliphatic group having 1-6 carbon atoms; and G is hydrogen, =O, =S, —NR'H, —SR', or —OR'.

The present disclosure also provides compounds of any one of Formulae (III) to (V), which are useful in in preparing compounds of galanal A, galanal B, and galanal analogues (e.g., compounds of Formula (II) or (VI)), such as by a process shown in Scheme 2:

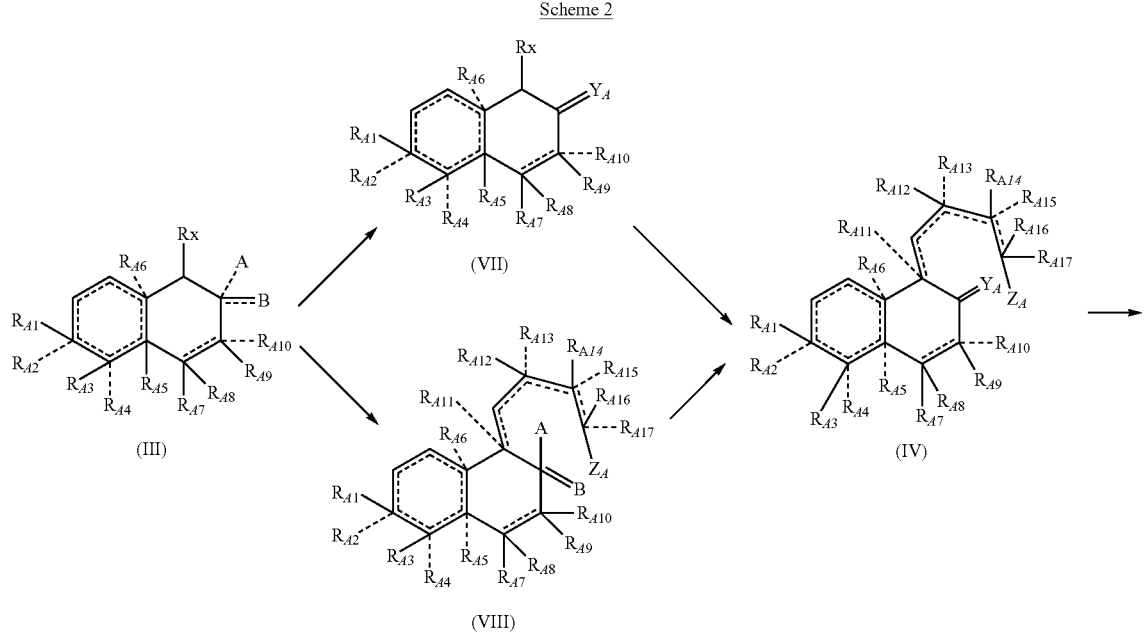

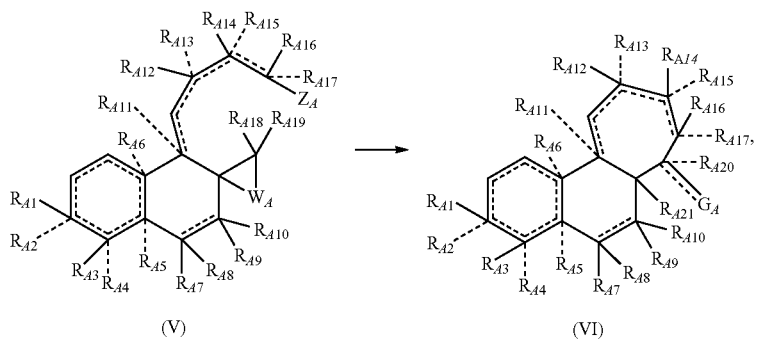

wherein:
R$_x$ represents halogen, =O, =S, —NR"H, —SR", —OR", alkyl, alkenyl, alkynyl, an amide group, an ester group, an aldehyde group, a nitrile group, an imino group, a ketone group, a thione group, an isonitrile group, an isothiocyanide group, a carbamate group, or a thiocarbamate group, wherein R" is hydrogen, a cyclic or acyclic, saturated or unsaturated, substituted or unsubstituted, branched or unbranched, (hetero)aliphatic group having 1 to 16 carbon atoms, an ester group, a ketone group, or a thione group;

group A represents hydrogen, halogen, or a cyclic or acyclic, substituted or unsubstituted, branched or unbranched, (hetero)aliphatic group having 1 to 6 carbon atoms;

group B represents halogen, =O, =S, —NR"H, —SR", —OR", alkenyl, alkynyl, an amide group, an ester group, an aldehyde group, a nitrile group, an imino group, a ketone group, a thione group, an isonitrile group, an isothiocyanide group, a carbamate group, or a thiocarbamate group;

G$_A$ is hydrogen, halogen, =O, =S, —N(R")$_2$, —SR", —OR", alkenyl, alkynyl, an amide group, an ester group, a phosphate group, an aldehyde group, a nitrile group, an imino group, a ketone group, a thione group, an isonitrile group, an isothiocyanide group, a carbamate group, a thiocarbamate group, or a cyclic or acyclic, substituted or unsubstituted, branched or unbranched, (hetero)aliphatic group having 1 to 6 carbon atoms;

W$_A$ is —O—, —S—, or —NR"—;

Y$_A$ is =O, =S, =NR" (R" is hydrogen, a cyclic or acyclic, saturated or unsaturated, substituted or unsubstituted, branched or unbranched, (hetero)aliphatic group having 1 to 16 carbon atoms, an ester group, a ketone group, or a thione group), or a cyclic or acyclic, substituted or unsubstituted, branched or unbranched, (hetero)aliphatic group having 1 to 6 carbon atoms; and Z$_A$ is alkenyl, alkynyl, an amide group, an ester group, an aldehyde group, a nitrile group, an imino group, a ketone group, a thione group, an isonitrile group, an isothiocyanide group, a thioate group, a thioamide, a dithioate, a carbamate group, a thiocarbamate group, an isocyanato group, or an isothiocyanato group;

R$_{A1}$, R$_{A2}$, R$_{A3}$, R$_{A4}$, R$_{A5}$, R$_{A6}$, R$_{A7}$, R$_{A8}$, R$_{A9}$, and R$_{A10}$ are each independently hydrogen, halogen, or a cyclic or acyclic, substituted or unsubstituted, branched or unbranched, (hetero)aliphatic group having 1 to 6 carbons;

R$_{A11}$, R$_{A13}$, R$_{A15}$, and R$_{A17}$ are each independently hydrogen, halogen, or a cyclic or acyclic, substituted or unsubstituted, branched or unbranched, (hetero)aliphatic group having 1 to 6 carbon atoms;

R$_{A12}$, R$_{A14}$, and R$_{A16}$ are each independently halogen, —N(R")$_2$, —SR", —OR", alkyl, alkenyl, alkynyl, an amide group, a carboxyl group, an ester group, an aldehyde group, a nitrile group, an imino group, a ketone group, a thione group, an isonitrile group, an isothiocyanide group, a urea group, a carbamate group, or a thiocarbamate group, or R$_{A14}$ and R$_{A15}$ are joined to form =O or =S;

R$_{A18}$ and R$_{A19}$ are each independently hydrogen, halogen, or a cyclic or acyclic, substituted or unsubstituted, branched or unbranched, (hetero)aliphatic group having 1 to 6 carbon atoms;

R$_{A20}$ is hydrogen, halogen, or a cyclic or acyclic, substituted or unsubstituted, branched or unbranched, (hetero) aliphatic group having 1 to 6 carbon atoms; and R$_{A21}$ is hydrogen, halogen, —N(R")$_2$, —SR", —OR", alkenyl, alkynyl, an amide group, a carboxyl group, an ester group, an aldehyde group, a nitrile group, an imino group, a ketone group, a thione group, an isonitrile group, an isothiocyanide group, a carbamate group, a thiocarbamate group, or a cyclic or acyclic, substituted or unsubstituted, branched or unbranched, (hetero)aliphatic group having 1 to 6 carbon atoms;

or R$_x$ and group A join to form a ring.

A compound of Formula (III) may be converted to a compound of Formula (IV). In certain embodiments, a compound of Formula (III) can be converted to a compound of Formula (VII), and the compound of Formula (VII) can be converted to a compound of Formula (IV). In certain embodiments, a compound of Formula (III) can be converted to a compound of Formula (VIII), and the compound of Formula (VIII) can be converted to a compound of Formula (IV).

A compound of Formula (IV) may be converted to a compound of Formula (V), e.g., by olefin peroxidation, by olefin peroxidation followed by reaction with a thiocyanate or thiourea, or by olefin aziridination.

A compound of Formula (V) may be converted to a compound of Formula (VI) as galanal or its analogue, through at least one step comprising a cyclization reaction between the group Z$_A$ and the three-membered ring

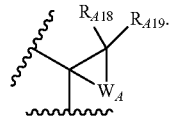

In some embodiments, the C-15, C-16, and C-17 carbon atoms of galanal can be converted into various combinations of functional groups by utilizing the different reaction selectivities of the C-15, C-16, and C-17 carbon atoms.

In certain embodiments, the synthesis processes of this disclosure can be particularly useful in preparing galanals or analogues of galanals, specifically, analogues with different substituents at C-8, C-13, C-15, C-16, and/or C-17, and/or stereoisomers thereof.

Galanal A, galanal B, and their analogues may be used as pharmaceutical agents themselves or be used as lead compounds in developing new pharmaceutical agents. Thus, another aspect of the present disclosure relates to pharmaceutical compositions comprising a compound described herein (e.g., galanal A, galanal B, or a galanal analogue) and a pharmaceutically acceptable excipient.

In another aspect, the present disclosure provides methods of using the compounds described herein (e.g., galanal A, galanal B, or a galanal analogue) to treat a disease mediated by the GLP-1 receptor (e.g., diabetes, a metabolic disorder, neurodegenarative disease, or cardiovascular disease) in a subject in need thereof. The method of using these compounds to treat a disease mediated by the GLP-1 receptor may include administered an effective amount of these compounds (e.g., orally or by injection (intravenous (i.v.) or subcutaneious)) or an effective amount of a pharmaceutical composition described herein to a subject in need thereof (e.g., human patients with, at risk for, or suspected of having diseases mediated by the GLP-1 receptor.

In further another aspect, the present disclosure features kits comprising a pharmaceutical composition described herein and optionally, instructions for using the kits.

Also within the scope of this present disclosure are a pharmaceutical composition described herein for use in treating a disease mediated by the GLP-1 receptor (e.g., diabetes, a metabolic disorder, neurodegenarative disease, or cardiovascular disease) in a subject, the use of lowering blood glucose levels in a subject, and the use of such a pharmaceutical composition for the manufacture of a medicament for treating a disease mediated by the GLP-1 receptor (e.g., diabetes) in a subject.

The details of one or more embodiments of the disclosure are set forth herein. Other features, objects, and advantages of the disclosure will be apparent from the Detailed Description, Examples, and Claims.

DETAILED DESCRIPTION

Figure 1:
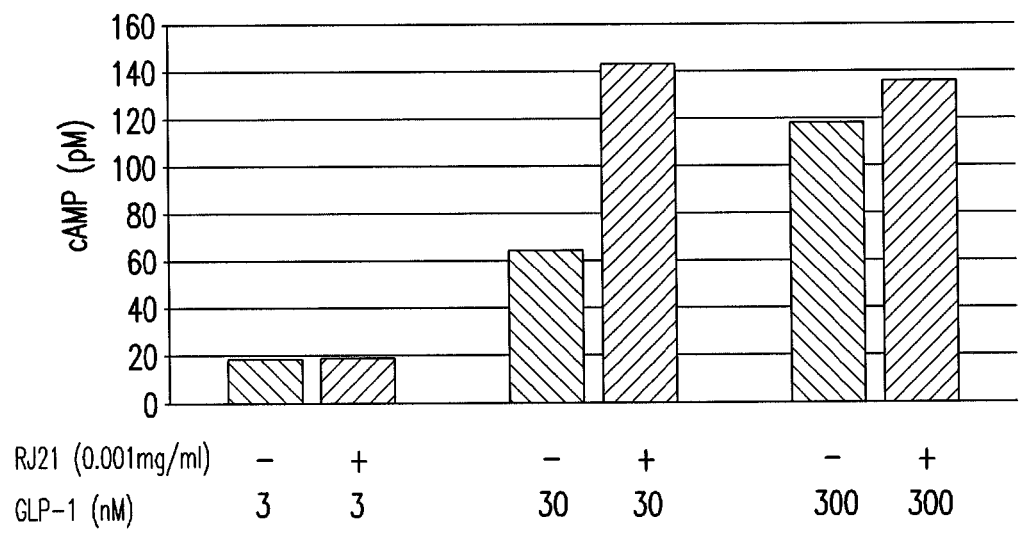
FIG. 1 shows the positive modulating effect of galanal B (RJ21) on GLP-1 dependent cAMP production from RIN-m5F cells in an in vitro biological assay.

This disclosure is further explained with the following embodiments, which are not intended to limit the scope of this disclosure.

I. Compounds

In one aspect, the present disclosure provides compounds of Formula (I):

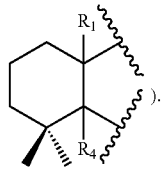

(I)

In Formula (I), W is —O—, —S— or —NR'—, and the epoxide (when W is —O—), thiirane (when W is —S—), or aziridine (when W is —NR'—) group can be opened and then react with the group Z. In certain embodiments, W can be —O—. In certain embodiments, Z can be alkenyl, alkynyl, an amide group, an ester group, an aldehyde group, a nitrile group, an imino group, a ketone group, a thione group, an isonitrile group, an isothiocyanide group, a thioate group, a thioamide, a dithioate, a carbamate group, a thiocarbamate group, an isocyanato group, or an isothiocyanato group. In certain embodiments, Z can be alkenyl, alkynyl, an amide group, an ester group, an aldehyde group, a nitrile group, an imino group, a ketone group, a thione group, an isonitrile group, an isothiocyanide group, a carbamate group, or a thiocarbamate group. In certain embodiments, Z can be an amide group, an ester group, an aldehyde group, a nitrile group, an imino group, or a ketone group. In certain embodiments, Z can be a nitrile group. An example of the nitrile group is cyano (—CN). The combination of W and Z may be selected according to the functional groups of the target molecule to be formed from the compound of Formula (I).

In certain embodiments, each of X and Y can independently be methylene, ethanediyl, vinylene bridge, or propanediyl. In certain embodiments, X can be methylene. In certain embodiments, Y can be methylene. The species of X and Y are selected according to the structure of the target molecule to be formed from the compound of Formula (I).

In certain embodiments, $R_1$ can be methyl. In certain embodiments, $R_2$ and $R_3$ may join to form cycloalkyl (e.g., substituted or unsubstituted cyclohexyl, such as, with substituents $R_1$ and $R_4$:

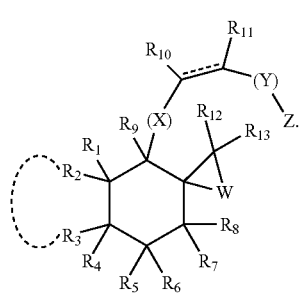

In certain embodiments, $R_4$ can be hydrogen. In certain embodiments, $R_5$ can be hydrogen. In certain embodiments, $R_6$ can be hydrogen. In certain embodiments, $R_7$ can be hydrogen. In certain embodiments, $R_8$ can be hydrogen. In certain embodiments, $R_9$ can be hydrogen. In certain embodiments, $R_{12}$ can be hydrogen. In certain embodiments, $R_{13}$ can be hydrogen. The species of $R_1$, $R_2$, $R_3$, $R_4$, $R_5$, $R_6$, $R_7$, $R_8$, $R_9$, $R_{12}$ and $R_{13}$ are selected according to the structure of the target molecule to be formed from the compound of Formula (I).

In certain embodiments, $R_{10}$ and $R_{11}$ can each independently be hydrogen, halogen, a cyclic or acyclic, saturated or unsaturated, substituted or unsubstituted, branched or unbranched, (hetero)aliphatic group having 1 to 6 carbon atoms, an amino group, an amide group, an ester group, an aldehyde group, a nitrile group, an imino group, a ketone group, a thione group, an isonitrile group, an isothiocyanide group, a carbamate group, or a thiocarbamate group. In certain embodiments, $R_{10}$ can be hydrogen. In certain embodiments, $R_{11}$ can be hydrogen. In certain embodiments, $R_{11}$ can be a cyclic or acyclic, saturated or unsaturated, substituted or unsubstituted, branched or unbranched, (hetero)aliphatic group having 1 to 6 carbon atoms (e.g., an acyclic, substituted or unsubstituted, branched or unbranched $C_{1-6}$ aliphatic, such as acyclic, substituted or unsubstituted, branched or unbranched, $C_{1-6}$ alkyl (e.g., —CH$_2$OR', such as —CH$_2$OH)). In certain embodiments, $R_{11}$ can be an ester group (e.g., —C(=O)O(acyclic, substituted or unsubstituted, branched or unbranched, $C_{1-6}$ alkyl), such as —C(=O)OMe). In certain embodiments, $R_{11}$ can be an aldehyde group. The species of $R_{10}$ and $R_{11}$ are selected according to the structure of the target molecule to be formed from the compound of Formula (I).

In certain embodiments, X and Y can be each methylene; $R_1$ can be methyl; $R_2$, $R_3$, and the two carbon atoms directly bonded therewith form a 3,3-dimethyl cyclohexane ring; $R_4$, $R_5$, $R_6$, $R_7$, $R_8$, $R_9$, $R_{10}$, $R_{12}$, and $R_{13}$ can be hydrogen; $R_{11}$ can be an amide group, an ester group, an aldehyde group, an alcohol group, a carbamate group, a thiocarbamate, a carbonate, a nitrile group, an amino group, an imino group; and the bond between the two carbon atoms directly bonded with $R_{10}$ and $R_{11}$ can be a double bond.

In another aspect, the present disclosure provides compounds of Formula (III).

In another aspect, the present disclosure provides compounds of Formula (IV).

In another aspect, the present disclosure provides compounds of Formula (V).

In another aspect, the present disclosure provides compounds of Formula (VI).

In another aspect, the present disclosure provides compounds of Formula (VII).

In another aspect, the present disclosure provides compounds of Formula (VIII).

In formula (V), $W_A$ is —O—, —S— or —NR"—, and the epoxide (when $W_A$ is —O—), thiirane (when $W_A$ is —S—), or aziridine (when $W_A$ is —NR"—) group can be opened and then react with the group $Z_A$. The combination of $W_A$ and $Z_A$ may be selected according to the functional groups of the target molecule to be formed from the compound of Formula (III).

In certain embodiments, group A can be alkyl (e.g., acyclic, substituted or unsubstituted, branched or unbranched, $C_{1-6}$ alkyl, such as methyl). In certain embodiments, - - - A can be absent. In certain embodiments, group B can be —OR" (e.g., —OH). In certain embodiments, ====== B can be alkenyl (e.g., acyclic, substituted or unsubstituted, branched or unbranched, $C_{2-6}$ alkenyl, such as =$CH_2$). In certain embodiments, $R_x$ can be halogen, =O, =S, —NR"H, —SR", —OR" (R" is hydrogen, a cyclic or acyclic, saturated or unsaturated, substituted or unsubstituted, branched or unbranched, (hetero)aliphatic group having 1 to 16 carbon atoms, an ester group, a ketone group, or a thione group), alkenyl, alkynyl, an amide group, an ester group, an aldehyde group, a nitrile group, an imino group, a ketone group, a thione group, an isonitrile group, an isothiocyanide group, a carbamate group, or a thiocarbamate group. In certain embodiments, $R_x$ can be alkyl (e.g., acyclic, saturated or unsaturated, substituted or unsubstituted, branched or unbranched $C_{1-6}$ alkyl). In certain embodiments, $Y_A$ can be acyclic, substituted or unsubstituted, branched or unbranched, (hetero)aliphatic group having 1 to 6 carbon atoms (e.g., acyclic, substituted or unsubstituted, branched or unbranched, $C_{1-6}$ alkenyl, such as =$CH_2$). In certain embodiments, $Z_A$ can be alkenyl, alkynyl, an amide group, an ester group, an aldehyde group, a nitrile group, an imino group, a ketone group, a thione group, an isonitrile group, an isothiocyanide group, a carbamate group, or a thiocarbamate group. In certain embodiments, $Z_A$ can be an amide group, an ester group, an aldehyde group, a nitrile group, an imino group, or a ketone group. In certain embodiments, $Z_A$ can be cyano. In certain embodiments, $W_A$ can be —O—. In certain embodiments, $G_A$ can be hydrogen. In certain embodiments, $G_A$ can be =O, =S, —SR", —OR", —N(R")$_2$, —OH, —SH, or —NH$_2$. In certain embodiments, $G_A$ can be can be =O. In certain embodiments, $G_A$ can be —OR" (e.g., —OH, —O(substituted or unsubstituted $C_{1-6}$ alkyl), or —OC(=O) (substituted or unsubstituted $C_{1-6}$ alkyl)). In certain embodiments, $G_A$ can be can be =S. In certain embodiments, $G_A$ can be —SR" (e.g., —SH). In certain embodiments, $G_A$ can be —N(R")$_2$, —NHR" (such as —NH (substituted or unsubstituted $C_{1-6}$ alkyl) or —NHC(=O) (substituted or unsubstituted $C_{1-6}$ alkyl)), or —NH$_2$. In certain embodiments, $G_A$ can be can be alkenyl (e.g., acyclic, substituted or unsubstituted, $C_{1-6}$ alkenyl, such as =CHC(=O) (substituted or unsubstituted $C_{1-6}$ alkyl))). In certain embodiments, $G_A$ can be can be a phosphate group (e.g., —OP(=O) (acyclic, substituted or unsubstituted, $C_{1-6}$ alkyl)$_2$). In certain embodiments, $R_{A1}$ can be hydrogen. In certain embodiments, $R_{A1}$ can be halogen. In certain embodiments, $R_{A1}$ can be an acyclic, substituted or unsubstituted, branched or unbranched, aliphatic group having 1 to 6 carbons (e.g., acyclic, substituted or unsubstituted, branched or unbranched, $C_{1-6}$ alkyl (such as —CF$_3$)). In certain embodiments, $R_{A1}$ can be —OR" (e.g., —OH). In certain embodiments, $R_{A1}$ can be —N(R")$_2$ (e.g., —NMe$_2$). In certain embodiments, $R_{A2}$ can be hydrogen. In certain embodiments, $R_{A1}$ and $R_{A2}$ can be joined to form =O. In certain embodiments, $R_{A3}$ can be hydrogen. In certain embodiments, $R_{A3}$ can be acyclic, substituted or unsubstituted, branched or unbranched, $C_{1-6}$ alkyl (e.g., methyl, —CF$_3$, —CH$_2$Br, —CH$_2$OH, —CH$_2$OC(=O) (substituted or unsubstituted $C_{1-6}$ alkyl), or ethyl). In certain embodiments, $R_{A3}$ can be carboxyl. In certain embodiments, $R_{A4}$ can be hydrogen. In certain embodiments, $R_{A4}$ can be acyclic, substituted or unsubstituted, branched or unbranched, $C_{1-6}$ alkyl (e.g., methyl, —CF$_3$, —CH$_2$OC(=O) (substituted or unsubstituted $C_{1-6}$ alkyl), or ethyl)). In certain embodiments, $R_{A3}$ and $R_{A4}$ can be joined to form alkenyl (e.g., =CH$_2$). In certain embodiments, $R_{A5}$ can be hydrogen. In certain embodiments, $R_{A5}$ can be acyclic, substituted or unsubstituted, branched or unbranched, $C_{1-6}$ alkyl (e.g., methyl or —CH$_2$OCF$_3$). In certain embodiments, $R_{A6}$ can be acyclic, substituted or unsubstituted, branched or unbranched, $C_{1-6}$ alkyl (e.g., methyl, ethyl, —CH$_2$OH, —CH$_2$OC(=O)Me, or —CH$_2$OC(=S)Me). In certain embodiments, $R_{A7}$ can be hydrogen. In certain embodiments, $R_{A7}$ can be acyclic, substituted or unsubstituted, branched or unbranched, $C_{1-6}$ alkyl (e.g., methyl). In certain embodiments, $R_{A7}$ can be —OR" (e.g., —OH). In certain embodiments, $R_{A8}$ can be hydrogen. In certain embodiments, $R_{A8}$ can be acyclic, substituted or unsubstituted, branched or unbranched, $C_{1-6}$ alkyl (e.g., methyl). In certain embodiments, $R_{A9}$ can be hydrogen. In certain embodiments, $R_{A9}$ can be acyclic, substituted or unsubstituted, branched or unbranched, $C_{1-6}$ alkyl (e.g., methyl). In certain embodiments, $R_{A10}$ can be hydrogen. In certain embodiments, $R_{A11}$ can be hydrogen. In certain embodiments, $R_{A12}$ can be hydrogen. In certain embodiments, $R_{A12}$ can be an amino group (e.g., —N(R")$_2$, —NHR", or —NH$_2$). In certain embodiments, - - - $R_{A13}$ is absent. In certain embodiments, $R_{A14}$ can be halogen, —NR"H, —SR", —OR", alkenyl, alkynyl, an amide group, a carboxyl group, an ester group, an aldehyde group, a nitrile group, an imino group, a ketone group, a thione group, an isonitrile group, an isothiocyanide group, a carbamate group, or a thiocarbamate group. In certain embodiments, $R_{A14}$ can be hydrogen. In certain embodiments, $R_{A14}$ can be alkyl (e.g., acyclic, substituted or unsubstituted, branched or unbranched, $C_{1-6}$ alkyl (e.g., —CH$_2$CF$_3$, —CH$_2$OR" (such as —CH$_2$OH), —CH$_2$SR" (such as —CH$_2$SH), —CH$_2$N(R")$_2$ (such as —CH$_2$NHMe or —CH$_2$NH$_2$), —CH$_2$OC(=O) (acyclic, substituted or unsubstituted, branched or unbranched, $C_{1-20}$ aliphatic (such as

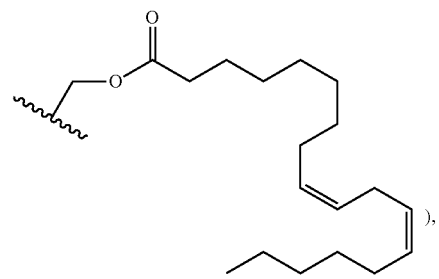 [SMILES: *COC(=O)CCCCCCC/C=C\C/C=C\CCCCC]

), or —CH$_2$C(=O)N(R")$_2$ (such as —CH$_2$C(=O)NH (substituted or unsubstituted $C_{1-6}$ alkyl))). In certain embodiments, $R_{A14}$ Can be a carboxyl group. In certain embodiments, $R_{A14}$ can be an ester group (e.g., —C(=O)O(acyclic, substituted or unsubstituted, branched or unbranched, $C_{1-6}$ alkyl), such as —C(=O)OMe). In certain embodiments, $R_{A14}$ can be an aldehyde group. In certain embodiments, $R_{A14}$ Can be a ketone group (e.g., —C(=O)-(acyclic, substituted or unsubstituted, branched or unbranched, $C_{1-6}$ alkyl), such as —C(=O)Me). In certain embodiments, $R_{A14}$ can be a urea group (e.g., —NHC(=O)—NH (substituted or unsubstituted phenyl), such as —NHC(=O)—NHPh). In certain embodiments, - - - $R_{A15}$ can be absent. In certain embodiments, $R_{A14}$ and $R_{A15}$ can be joined to form =O or =S. In certain embodiments, $R_{A16}$ can be hydrogen. In certain embodiments, $R_{A16}$ can be a carbamate group (e.g., —NHC(=O)O(acyclic, substituted or unsubstituted, branched or unbranched, $C_{1-6}$ alkyl), such as —NHC(=O)OEt). In certain embodiments, $R_{A17}$ can be hydrogen. In certain embodiments, $R_{A20}$ can be hydrogen. In certain embodiments, - - - $R_{A20}$ can be absent. In certain embodiments, $R_{A21}$ can be hydrogen. In certain embodiments, $R_{A21}$ can be a cyclic or acyclic, substituted or unsubstituted, branched or unbranched, (hetero)aliphatic group having 1 to 6 carbon atoms. In certain embodiments, $R_{A21}$ can be acyclic, substituted or unsubstituted, branched or unbranched, $C_{1-6}$ alkyl (e.g., —CH$_2$OR" (such as —CH$_2$OH, —CH$_2$OC(=O)OMe, or —CH$_2$OC(=O) (acyclic, substituted or unsubstituted, branched or unbranched, $C_{1-20}$ aliphatic (such as

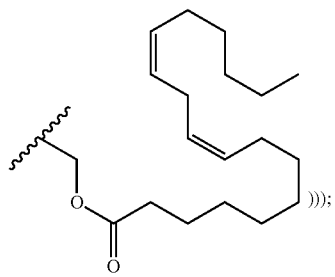 [SMILES: *COC(=O)CCCCCCC/C=C\C/C=C\CCCCC]

—CH$_2$SR" (such as —CH$_2$SH, —CH$_2$SC(=O) (substituted or unsubstituted phenyl); or —CH$_2$N(R")$_2$ (such as —CH$_2$NHR" (e.g., —CH$_2$NHMe) or —CH$_2$NH$_2$)). In certain embodiments, $R_{A21}$ can be acyclic, substituted or unsubstituted, branched or unbranched, $C_{2-6}$ alkenyl (e.g., —CH=CHCH$_3$ or —CH=NBn). In certain embodiments, $R_{A21}$ can be an aldehyde group. In certain embodiments, $R_{A21}$ can be a carboxyl group. In certain embodiments, each instance of R" can independently be hydrogen. In certain embodiments, each instance of R" can independently be acyclic, substituted or unsubstituted, branched or unbranched, $C_{1-6}$ alkyl (e.g., methyl, ethyl, propyl, or butyl).

The tricyclic ring system (e.g., 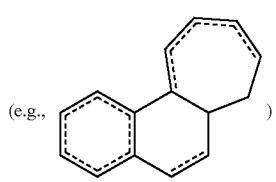 )

of Formula (I) may include substituents in addition to one or more of $R_{A1}$ to $R_{A17}$, $R_{A20}$ to $R_{A21}$, and $G_A$, as valency permits. In certain embodiments, the tricyclic ring system of Formula (I) can further be substituted at one or two of the positions marked with "*":

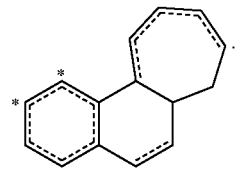

In certain embodiments, the tricyclic ring system of Formula (I) can further be substituted with one or more substituents independently selected from the group consisting of halogen; substituted and unsubstituted $C_{1-6}$ aliphatic (e.g., unsubstituted $C_{1-6}$ alkyl, such as —CH$_3$); and —OR" (e.g., —OH).

In certain embodiments, the compound of Formula (III) can be of Formula (III-A):

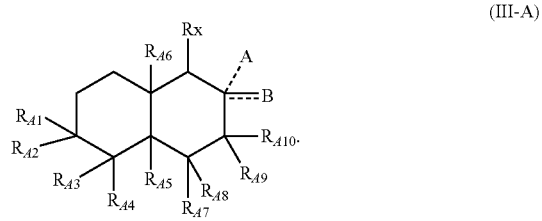

(III-A)

In certain embodiments, the compound of Formula (III) can be of Formula (III-B):

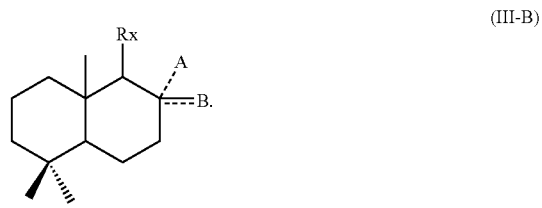

(III-B)

In certain embodiments, the compound of Formula (IV) can be of Formula (IV-A):

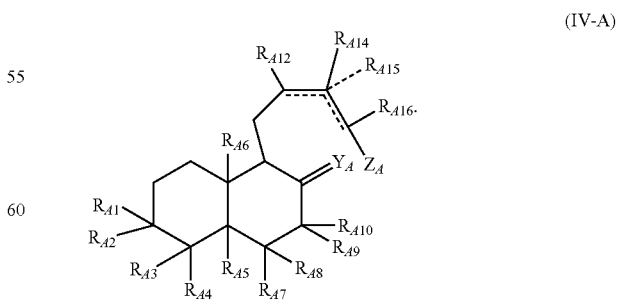

(IV-A)

In certain embodiments, the compound of Formula (IV) can be of Formula (IV-B):

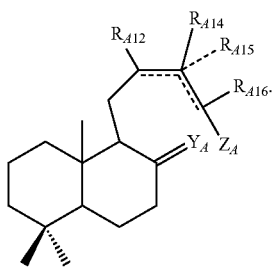
(IV-B)

In certain embodiments, the compound of Formula (IV) can be of Formula (IV-C):

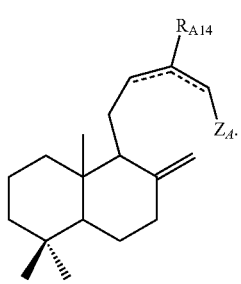
(IV-C)

In certain embodiments, the compound of Formula (V) can be of Formula (V-A):

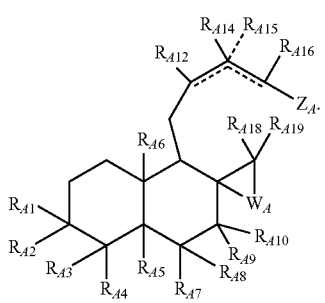
(V-A)

In certain embodiments, the compound of Formula (V) can be of Formula (V-B):

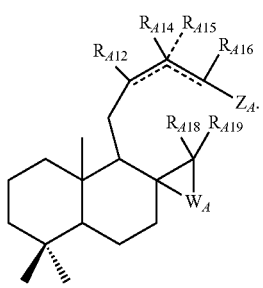
(V-B)

In certain embodiments, the compound of Formula (V) can be of the Formula

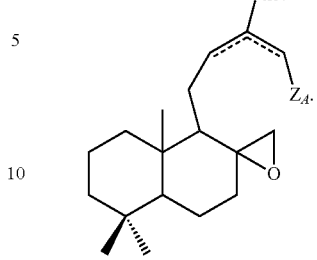
(V-C)

In certain embodiments, the compound of Formula (VI) can be of Formula (VI-A):

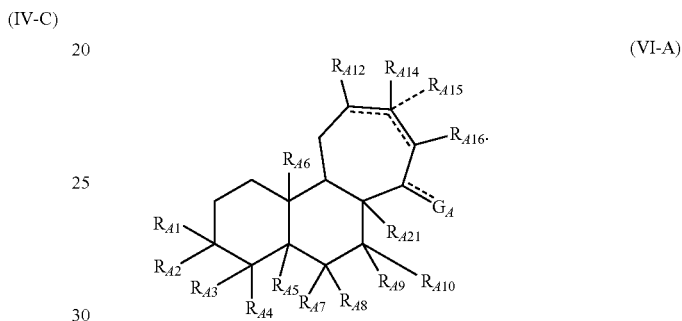
(VI-A)

In certain embodiments, the compound of Formula (VI) can be of the formula:

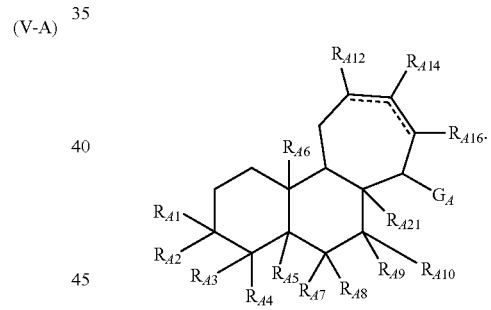

In certain embodiments, the compound of Formula (VI) can be of Formula (VI-B):

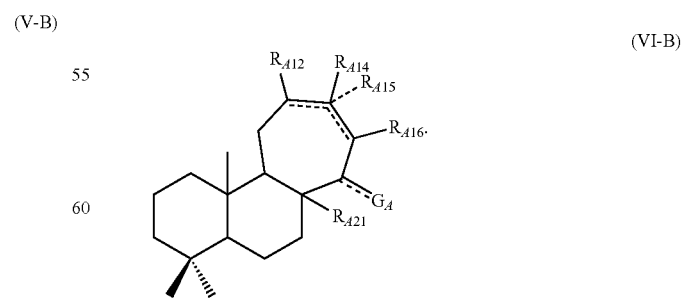
(VI-B)

In certain embodiments, the compound of Formula (VI) can be of Formula (VI-C):

(VI-C)

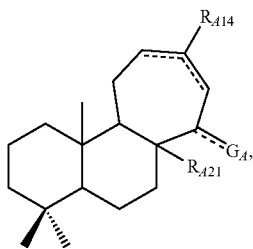

wherein $G_A$ can be =O or —OR", and $R_{A21}$ can be —CH$_2$OR" or an aldehyde group, wherein the two instances of R" may be the same or different.

In certain embodiments, the compound of Formula (VI) can be of Formula (VI-D):

(VI-D)

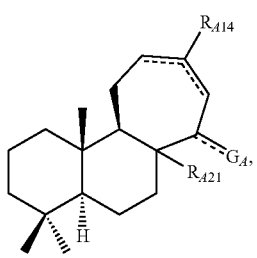

wherein $G_A$ can be =O or —OR", and $R_{A21}$ can be —CH$_2$OR" or an aldehyde group, wherein the two instances of R" may be the same or different.

In certain embodiments, a compound can be prepared by a method described herein can be galanal A, galanal B, or of the formula:

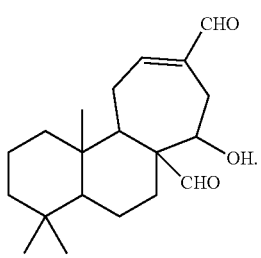 [SMILES: CC1(C)CCCC2(C)C1CCC1(C=O)C(O)CC(C=O)=CCC21]

In certain embodiments, a compound can be prepared by a method described herein can be compound RJ27, RJ28, RJ29, RJ30, or RJ131:

RJ27

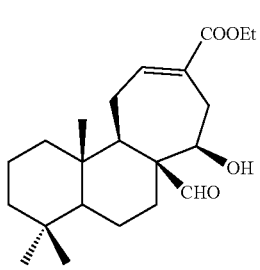

RJ28

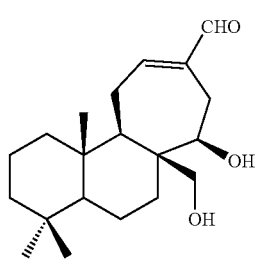

RJ29

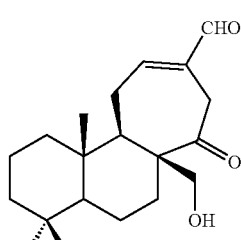

RJ30

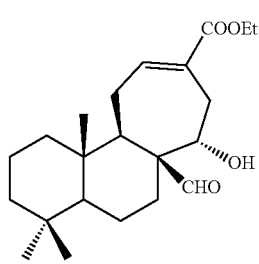

RJ31

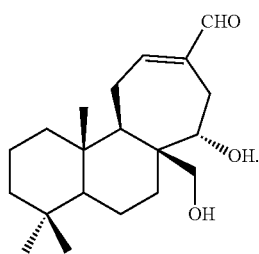

In certain embodiments, a compound can be prepared by a method described herein can be of the formula:

RJ-011

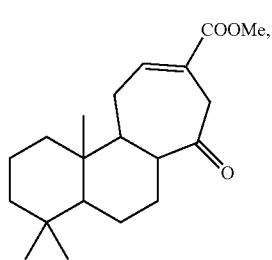

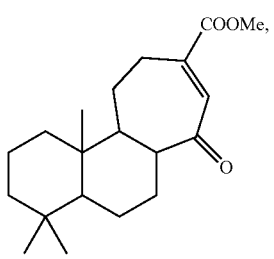
RJ-012
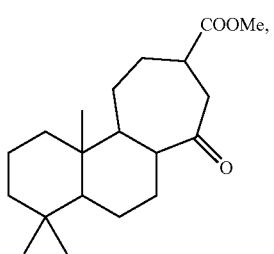
RJ-015
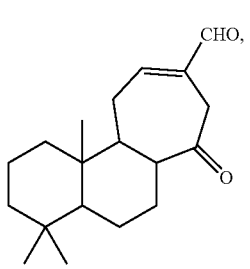
RJ-017
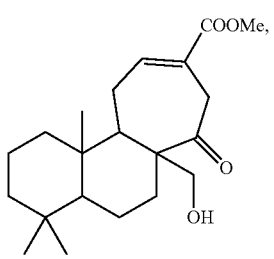
RJ-022
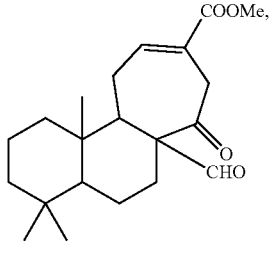
RJ-029
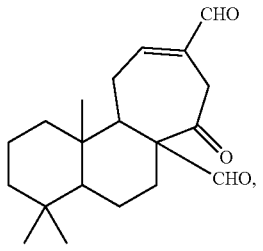
RJ-030
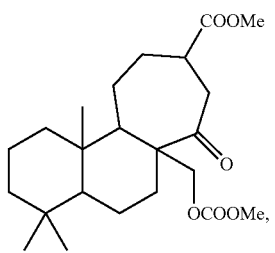
RJ-38
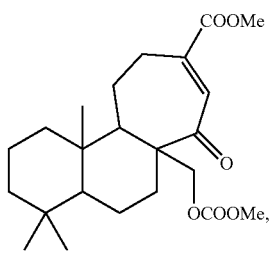
RJ-39
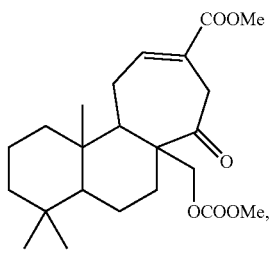
RJ-40
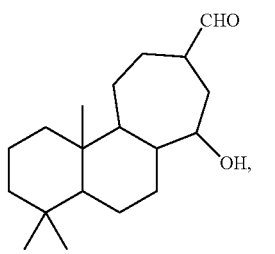
RJ-002
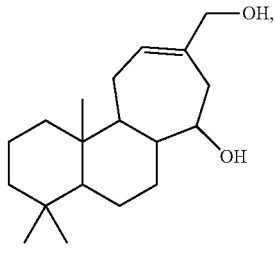
RJ-013
RJ-014
RJ-018
RJ-019
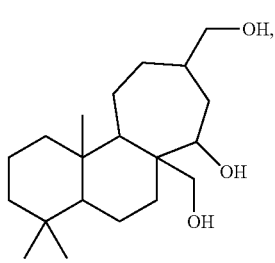
RJ-023
RJ-024

-continued
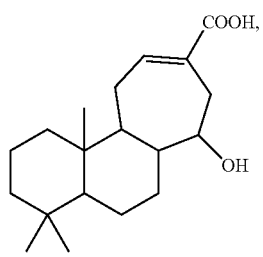
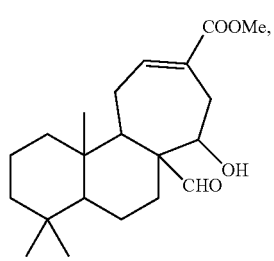
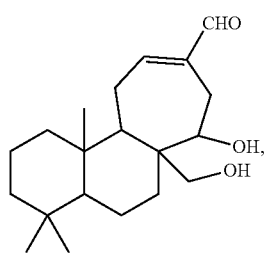
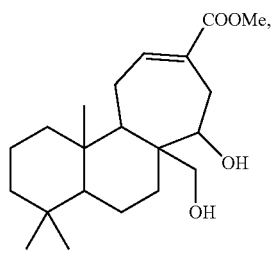
RJ-031
RJ-032
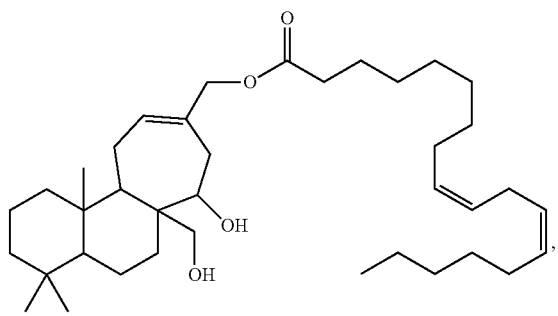
-continued
RJ-026
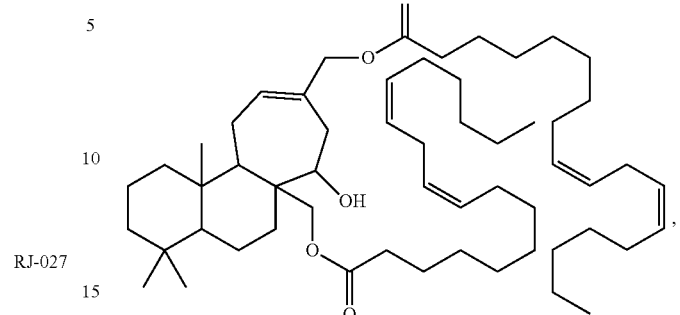
RJ-027
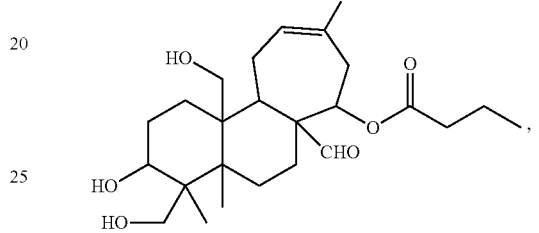
RJ-028
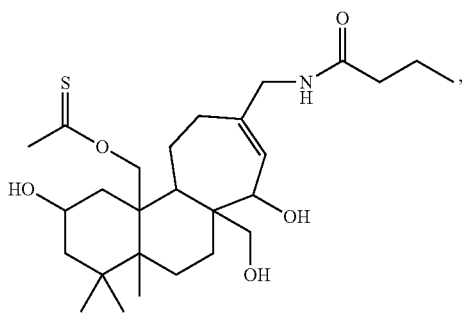
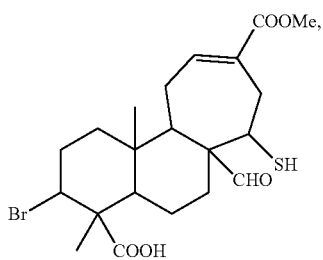
RJ-33
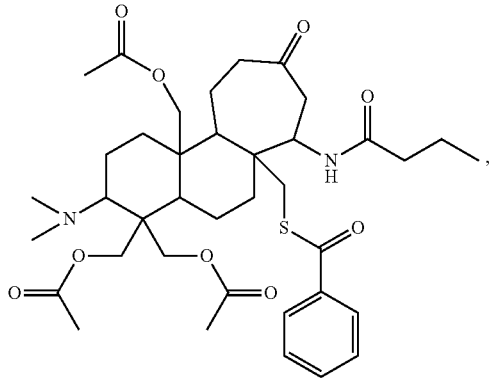
RJ-34

-continued
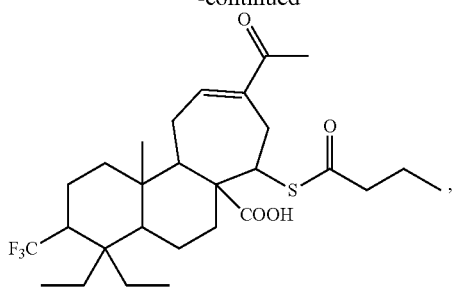
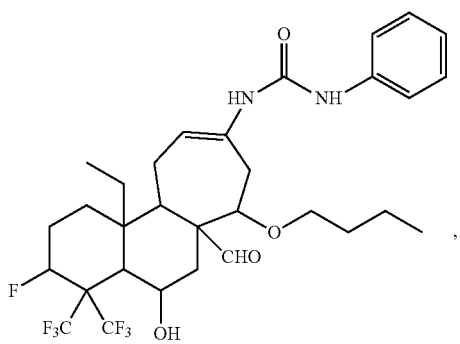
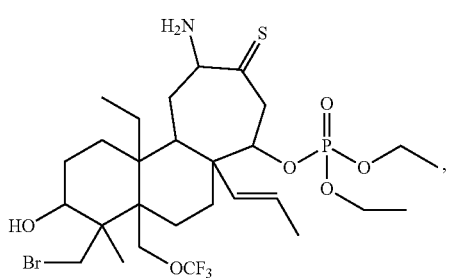
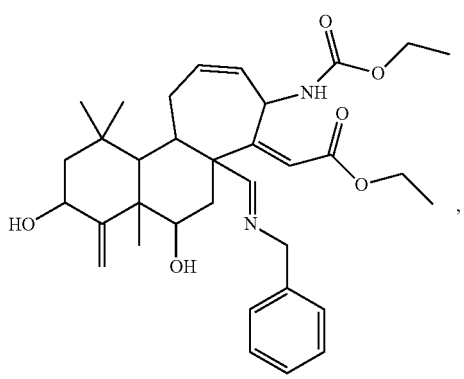
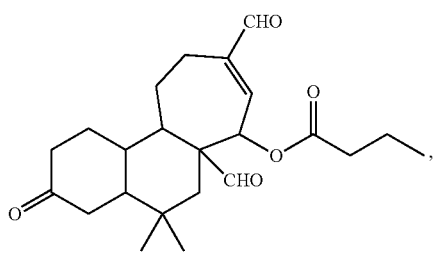
-continued
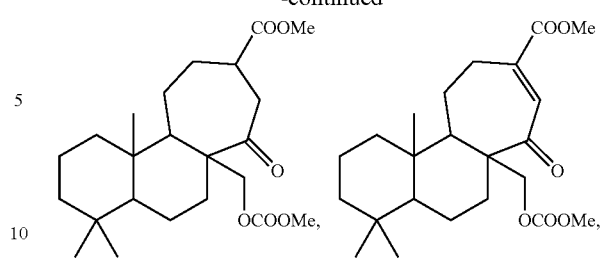
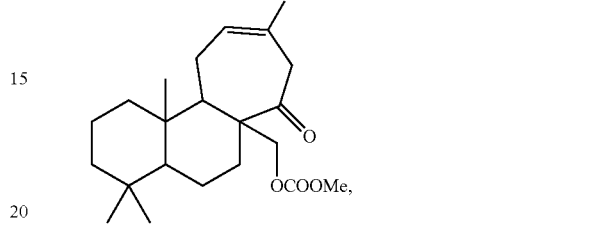
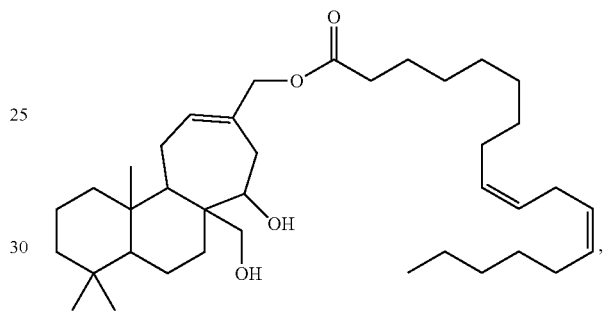
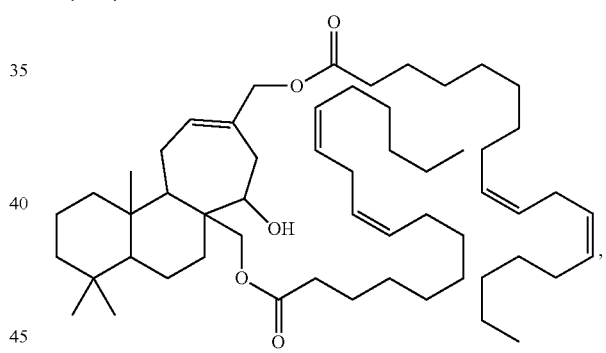
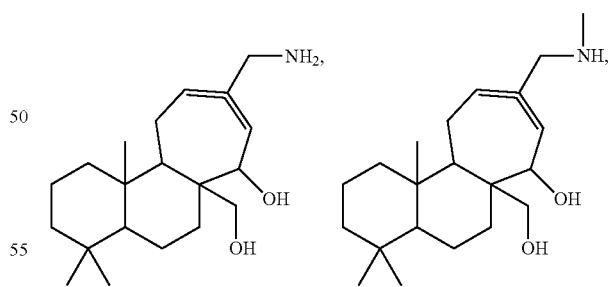
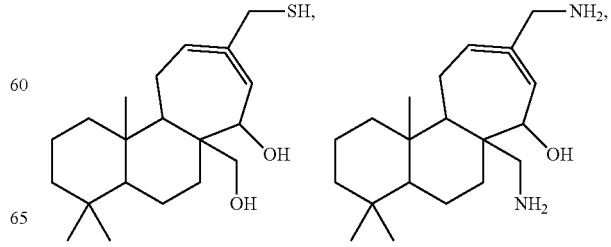

-continued
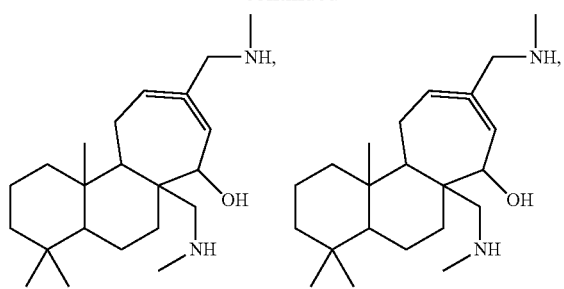 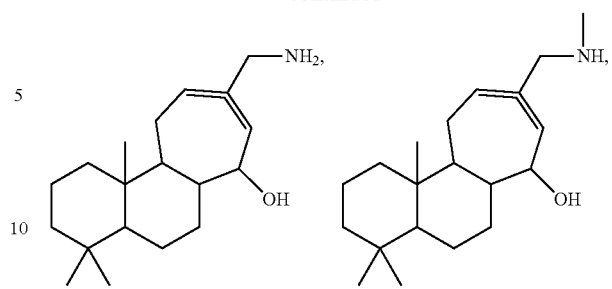
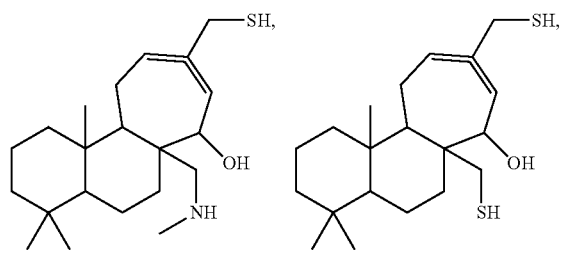 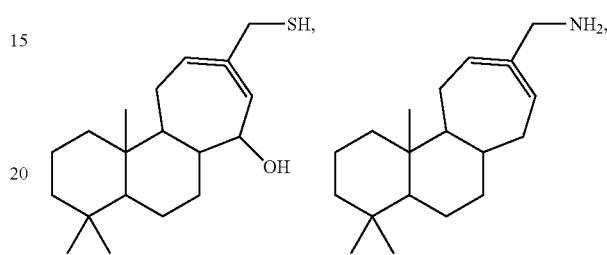
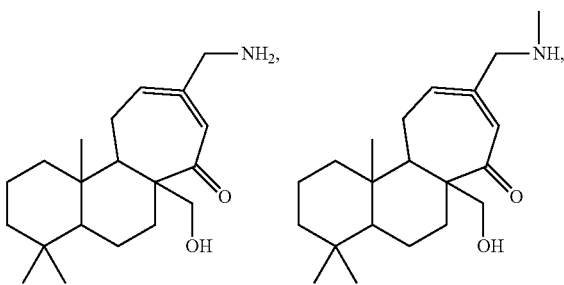 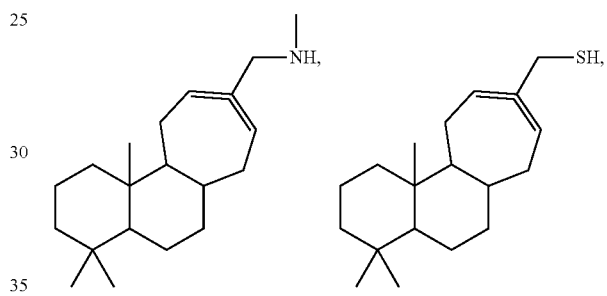
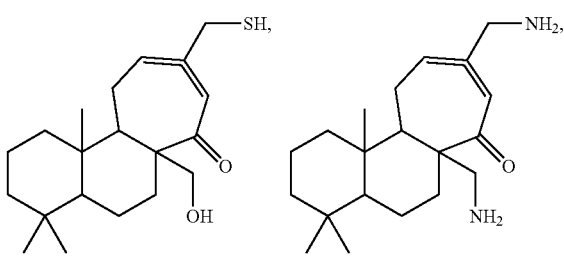 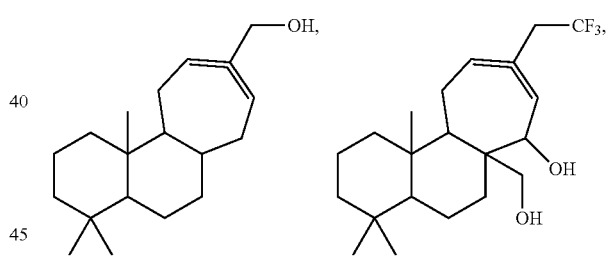
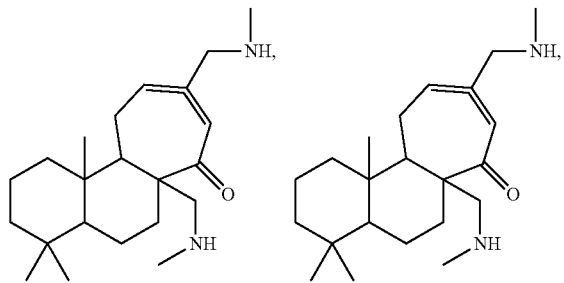 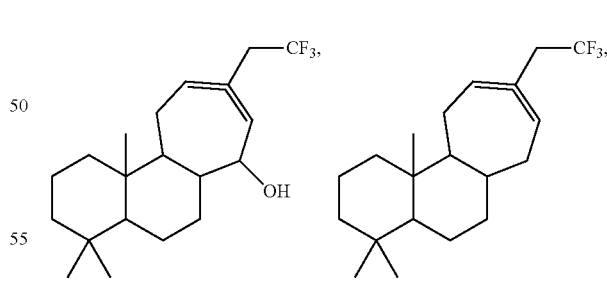
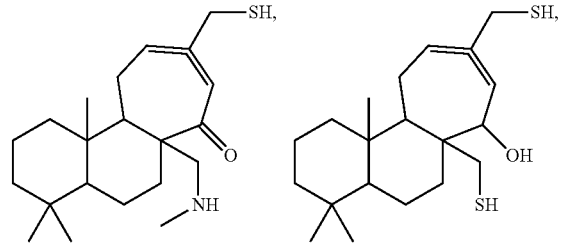 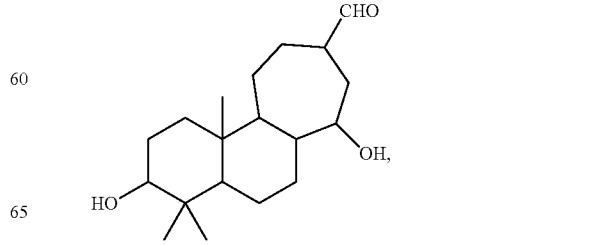

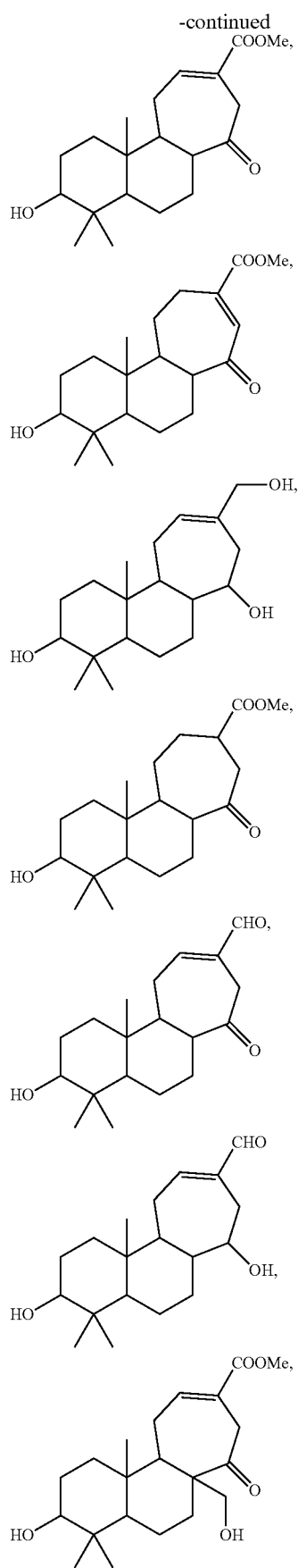
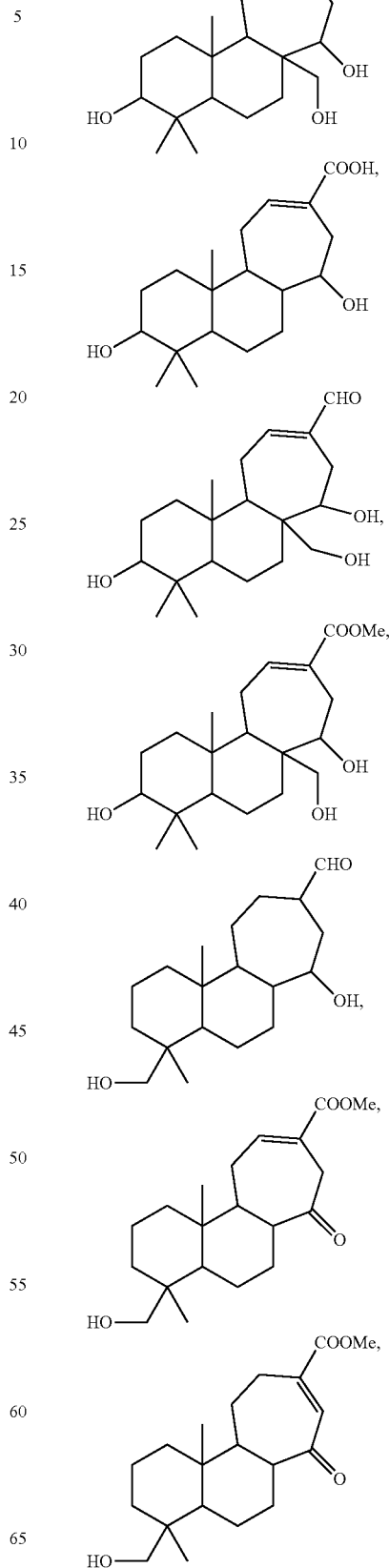

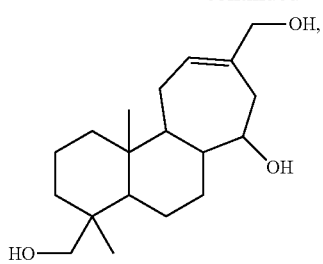

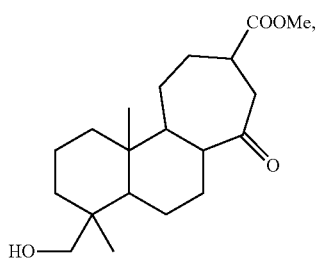

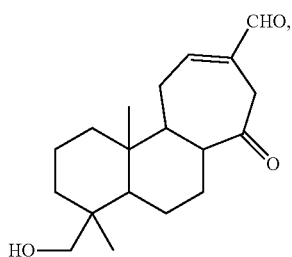

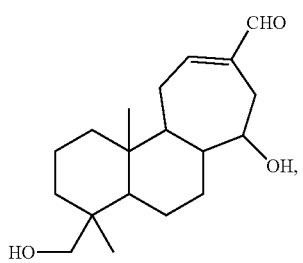

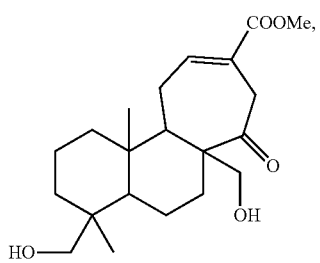

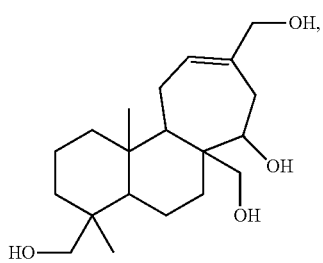

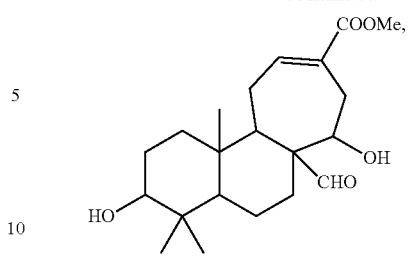

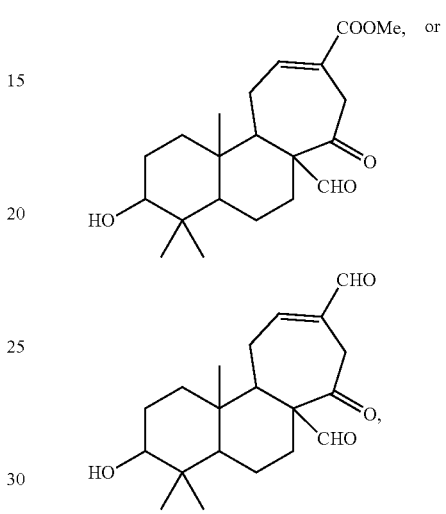

or a pharmaceutically acceptable salt thereof, wherein

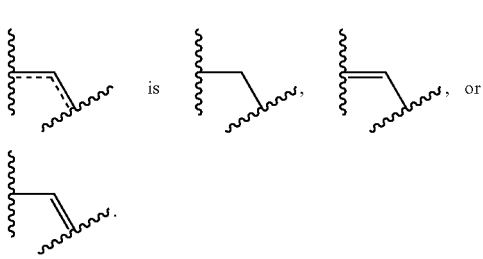

II. Preparation of the Compounds According to Scheme 1

Compounds of Formula (II) may be prepared by a process according to Scheme 1. Firstly, a compound of Formula (c) can be converted to a compound of Formula (a). Examples of a compound of Formula (c) include sclareolide, ambrox, γ-bicyclohomofarnesal, albicanol, larixol, and Wieland-Miescher ketone that are shown below.

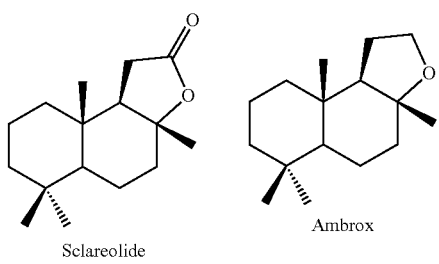

-continued

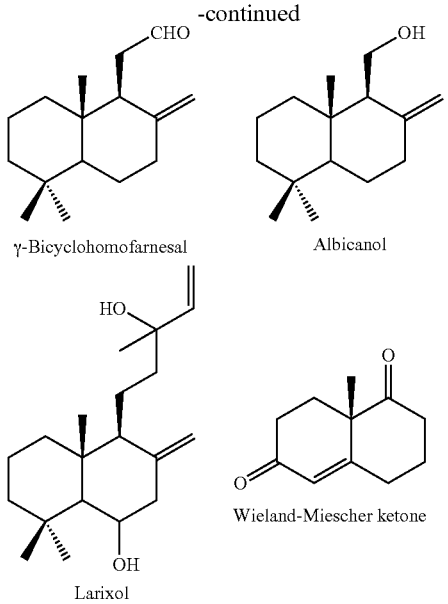

γ-Bicyclohomofarnesal    Albicanol

Larixol    Wieland-Miescher ketone

Next, a compound of Formula (a) may be reacted with a compound of Formula (b) to provide a compound of Formula (d), wherein a C═C double bond is formed between the two carbon atoms directly bonded with $R_{10}$ and $R_{11}$, respectively. The solvent used in the reaction may be a suitable solvent described herein (e.g., toluene, benzene, diethyl ether, THF, methylcyclohexane, cyclohexene, or dichloromethane).

Then, the C═C double bond directly on the cyclohexyl ring and directly bonded with $R_{12}$ and $R_{13}$ of a compound of Formula (d) may be selectively converted to an epoxide ring (when W is —O—), a thiirane ring (when W is —S—), or an aziridine ring (when W is —NR'—) to generate a compound of Formula (I-A). The selective conversion may be carried out using m-chloroperoxybenzoic acid (mCPBA) in a suitable solvent described herein (e.g., dichloromethane (DCM)) at a suitable temperature described herein (e.g., a temperature of 0° C. to room temperature), or using hydrogen peroxide, peroxycarboxylic acids (generated in-situ or preformed), alkyl hydroperoxides, oxygen, bis(acetylacetonate)oxovanadium, sodium hypochlorite, sodium periodate, titanium(iv) oxide, molybdenum(vi) oxide, magnesium monoperoxyphthalate hexahydrate, vanadyl acetylacetonate dimethyldioxirane, or other peroxide-containing reagents.

Moreover, a preparation process described herein may further include hydrogenating a compound of Formula (I-A) to form a compound of Formula (I-B). The hydrogenation step may uses $H_2$ (the pressure of which is about 1 atmosphere or greater than 1 atmosphere) or a silane, in the presence of a transition metal catalyst (e.g., palladium on carbon, platinum on carbon, palladium, platinum, nickel, or Raney nickel).

When G is ═O, a process described herein may further comprise converting G to —OH. When the moiety —$CR_{12}R_{13}$—W—$R_{14}$ is —$CH_2$—OH, a process described herein may further comprise converting —$CR_{12}R_{13}$—W—$R_{14}$ to —CHO.

In certain embodiments, $R_{14}$ and $R_{15}$ can be hydrogen. In certain embodiments, G can be ═O. In certain embodiments, G can be —OR' (e.g., —OH, —O(substituted or unsubstituted $C_{1-6}$ alkyl), or —OC(═O) (substituted or unsubstituted $C_{1-6}$ alkyl)). In certain embodiments, G can be can be ═S. In certain embodiments, G can be —SR' (e.g., —SH or —S(substituted or unsubstituted $C_{1-6}$ alkyl)). In certain embodiments, G can be —NHR' (such as —NH (substituted or unsubstituted $C_{1-6}$ alkyl) or —NHC(═O) (substituted or unsubstituted $C_{1-6}$ alkyl)) or —$NH_2$. In certain embodiments, W can be —O—. In certain embodiments, W can be —S—. In certain embodiments, W can be —NR'— (e.g., —N(substituted or unsubstituted $C_{1-6}$ alkyl)- or —NH—). In certain embodiments, Y can be methylene. In certain embodiments, Y can be ethanediyl, vinylene bridge, or propanediyl. In certain embodiments, Z can be an amide group, an ester group, an aldehyde group, a nitrile group, an imino group, or a ketone group. In certain embodiments, Z can be cyano (—CN). In certain embodiments, X can be methylene. In certain embodiments, X can be ethanediyl, vinylene bridge, or propanediyl. In certain embodiments, $R_1$ can be substituted or unsubstituted, branched or unbranched, $C_{1-6}$ alkyl (e.g., methyl, —$CH_2OH$, —$CH_2OC(═O)Me$, or —$CH_2OC(═S)Me$). In certain embodiments, $R_2$, $R_3$, and the two carbon atoms directly bonded therewith can form cycloalkyl (e.g., a 3,3-dimethyl cyclohexane ring (e.g., 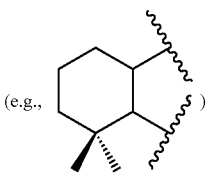 )

that is unsubstituted or substituted (e.g., substituted with —OH)). In certain embodiments, $R_4$, $R_5$, $R_6$, $R_7$, $R_8$, $R_9$, $R_{10}$, $R_{12}$, and $R_{13}$ can be hydrogen. In certain embodiments, $R_4$ can be hydrogen. In certain embodiments, $R_4$ can be substituted or unsubstituted, branched or unbranched, $C_{1-6}$ alkyl (e.g., methyl or —$CH_2OCF_3$). In certain embodiments, $R_5$ can be hydrogen. In certain embodiments, $R_5$ can be substituted or unsubstituted, branched or unbranched, $C_1$-alkyl (e.g., methyl). In certain embodiments, $R_5$ can be —OR' (e.g., —OH). In certain embodiments, $R_6$ can be hydrogen. In certain embodiments, $R_6$ can be substituted or unsubstituted, branched or unbranched, $C_{1-6}$ alkyl (e.g., methyl). In certain embodiments, $R_7$ can be hydrogen. In certain embodiments, $R_7$ can be substituted or unsubstituted, branched or unbranched, $C_{1-6}$ alkyl (e.g., methyl). In certain embodiments, $R_8$ can be hydrogen. In certain embodiments, $R_9$ can be hydrogen. In certain embodiments, $R_{10}$ can be hydrogen. In certain embodiments, $R_{10}$ can be an amino group (e.g., —$N(R')_2$, —NHR', or —$NH_2$). In certain embodiments, $R_{11}$ can be hydrogen. In certain embodiments, $R_{11}$ can be an amide group, an ester group, an aldehyde group, an alcohol group, a carbamate group, a thiocarbamate, a carbonate, a nitrile group, an amino group, an imino group, or acyclic, substituted or unsubstituted, branched or unbranched, $C_{1-6}$ alkyl. In certain embodiments, $R_{11}$ can be an ester group, an aldehyde group, a ketone group, or substituted or unsubstituted, branched or unbranched, $C_{1-6}$ alkyl. In certain embodiments, $R_{11}$ can be substituted or unsubstituted, branched or unbranched, $C_{1-6}$ alkyl (e.g., —$CH_2CF_3$, —$CH_2OR'$ (such as —$CH_2OH$), —$CH_2SR'$ (such as —$CH_2SH$), —$CH_2N(R')_2$ (such as —$CH_2NHMe$ or —$CH_2NH_2$), or —$CH_2C(═O)N(R')_2$ (such as —$CH_2C(═O)NH$ (substituted or unsubstituted $C_{1-6}$ alkyl))). In certain embodiments, $R_{11}$ can be an ester group (e.g., —C(═O)O(substituted or unsubstituted, branched or unbranched, $C_{1-6}$ alkyl), such as —C(═O)OMe). In certain embodiments, $R_{11}$ can be an aldehyde group. In certain embodiments, $R_{11}$ can be a ketone group (e.g., —C(═O)— (substituted or unsubstituted, branched or unbranched, $C_{1-6}$ alkyl), such as —C(=O)Me). In certain embodiments, $R_{12}$ can be hydrogen. In certain embodiments, $R_{13}$ can be hydrogen. In certain embodiments, $R_{14}$ can be hydrogen. In certain embodiments, $R_{14}$ can be substituted or unsubstituted, branched or unbranched, $C_{1-6}$ alkyl (e.g., —C(=O)OMe or —C(=O) (substituted or unsubstituted, $C_{2-20}$ alkenyl). In certain embodiments, —$CR_{12}R_{13}$—W—$R_{14}$ can be —$CH_2OH$. In certain embodiments, $R_{15}$ can be hydrogen. In certain embodiments, - - - $R_{15}$ can be absent. In certain embodiments, R' can be hydrogen. In certain embodiments, R' can be substituted or unsubstituted, branched or unbranched, $C_{1-6}$ alkyl (e.g., methyl, ethyl, propyl, or butyl). In certain embodiments, the bond between the two carbon atoms directly bonded with $R_{10}$ and $R_{11}$ in Formula (I) or (II) can be a double bond. In certain embodiments, the bond between the two carbon atoms directly bonded with $R_{10}$ and $R_{11}$ in Formula (I) or (II) can be a single bond.

For example, when galanal A and galanal B is to be formed from a compound of Formula (I), W can be —O—; X and Y can be each methylene; Z can be alkenyl, alkynyl, an amide group, an ester group, an aldehyde group, a nitrile group, an imino group, a ketone group, a thione group, an isonitrile group, an isothiocyanide group, a thioate group, a thioamide, a dithioate, a carbamate group, a thiocarbamate group, an isocyanato group, or an isothiocyanato group; $R_1$ can be methyl; $R_2$, $R_3$, and the two carbon atoms directly bonded therewith form a 3,3-dimethyl cyclohexane ring; $R_4$, $R_5$, $R_6$, $R_7$, $R_8$, $R_9$, $R_{10}$, $R_{12}$ and $R_{13}$ can be hydrogen; $R_{11}$ can be an amide group, an ester group, an aldehyde group, an alcohol group, a carbamate group, a thiocarbamate, a carbonate, a nitrile group, an amino group, an imino group, a heteroaliphatic group or other functional group that can be converted to the corresponding aldehyde group of galanal A and galanal B; and the bond between the two carbon atoms directly bonded with $R_{10}$ and $R_{11}$ can be a double bond.

Moreover, formations of the following galanal analogues (a1) to (a7) are discussed below.

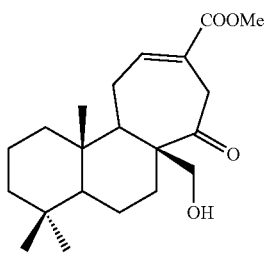
(a1)

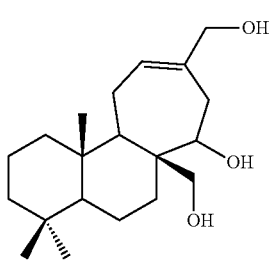
(a2)

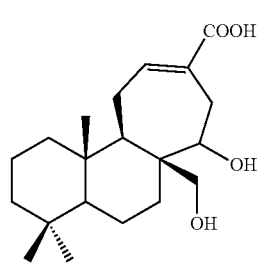
(a3)

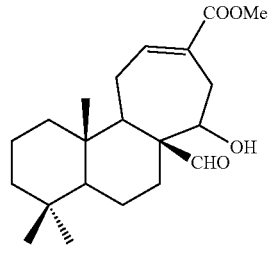
(a4)

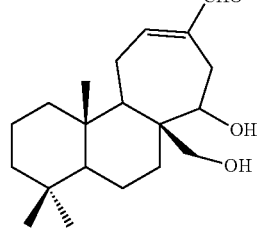
(a5)

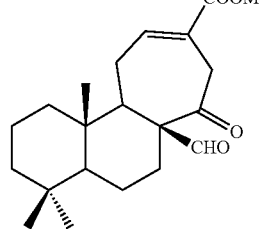
(a6)

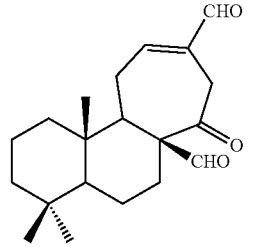
(a7)

In a case where the galanal analogue (a1) is to be formed from a compound of Formula (I), W, X, Y, $R_1$, $R_2$, $R_3$, $R_4$, $R_5$, $R_6$, $R_7$, $R_8$, $R_9$, $R_{10}$, $R_{12}$, and $R_{13}$ can be the same as in the case of galanal A or galanal B; Z can be an amide group, an ester group, an aldehyde group, a nitrile group, an imino group, or a ketone group; and $R_{11}$ can be an ester group.

In a case where the galanal analogue (a2) is to be formed from a compound of Formula (I), W, X, Y, $R_1$, $R_2$, $R_3$, $R_4$, $R_5$, $R_6$, $R_7$, $R_8$, $R_9$, $R_{10}$, $R_{12}$, and $R_{13}$ can be the same as in the case of galanal A or galanal B; Z can be an amide group, an ester group, an aldehyde group, a nitrile group, an imino group, or a ketone group; and $R_{11}$ can be hydroxymethyl.

In a case where the galanal analogue (a3) is to be formed from a compound of Formula (I), W, X, Y, $R_1$, $R_2$, $R_3$, $R_4$, $R_5$, $R_6$, $R_7$, $R_8$, $R_9$, $R_{10}$, $R_{12}$, and $R_{13}$ can be the same as in the case of galanal A or galanal B; and $R_{11}$ can be a carboxyl group or an ester group.

In a case where the galanal analogue (a4) is to be formed from a compound of Formula (I), W, X, Y, $R_1$, $R_2$, $R_3$, $R_4$, $R_5$, $R_6$, $R_7$, $R_8$, $R_9$, $R_{10}$, $R_{12}$, and $R_{13}$ can be the same as in the case of galanal A or galanal B; Z can be an amide group, an ester group, an aldehyde group, a nitrile group, an imino group, or a ketone group; and $R_{11}$ can be an ester group.

In a case where the galanal analogue (a5) is to be formed from a compound of Formula (I), W, X, Y, $R_1$, $R_2$, $R_3$, $R_4$, $R_5$, $R_6$, $R_7$, $R_8$, $R_9$, $R_{10}$, $R_{12}$, and $R_{13}$ can be the same as in the case of galanal A or galanal B; Z can be an amide group, an ester group, an aldehyde group, a nitrile group, an imino group, or a ketone group; and $R_{11}$ can be an aldehyde group.

In a case where the galanal analogue (a6) is to be formed from a compound of Formula (I), W, X, Y, $R_1$, $R_2$, $R_3$, $R_4$, $R_5$, $R_6$, $R_7$, $R_8$, $R_9$, $R_{10}$, $R_{12}$, and $R_{13}$ can be the same as in the case of galanal A or galanal B; Z can be an amide group, an ester group, an aldehyde group, a nitrile group, an imino group, or a ketone group; and $R_{11}$ can be an ester group.

In a case where the galanal analogue (a7) is to be formed from a compound of Formula (I), W, X, Y, $R_1$, $R_2$, $R_3$, $R_4$, $R_5$, $R_6$, $R_7$, $R_8$, $R_9$, $R_{10}$, $R_{12}$, and $R_{13}$ can be the same as in the case of galanal A or galanal B; Z can be an amide group, an ester group, an aldehyde group, a nitrile group, an imino group, or a ketone group; and $R_{11}$ can be an aldehyde group.

III. Preparation of the Compounds According to Scheme 2

Galanal A, galanal B, or an analogue thereof, may also be prepared according to Scheme 2. A step of converting a compound of Formula (III) to a compound of Formula (IV) may include first converting a compound of Formula (III) to a compound of Formula (VII) by forming a C=$Y_A$ double bond; and then converting the compound of Formula (VII) to a compound of Formula (IV) by converting the moiety $R_x$ to the moiety

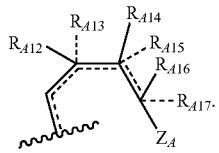

A step of converting a compound of Formula (III) to a compound of Formula (IV) may also include first converting a compound of Formula (III) to a compound of Formula (VIII) by converting the moiety $R_x$ to the moiety

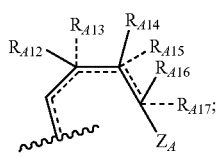

and then converting the compound of Formula (VIII) to a compound of Formula (IV) by forming a C=$Y_A$ double bond. In certain embodiments, $R_x$ can comprise an aldehyde or ketone moiety,

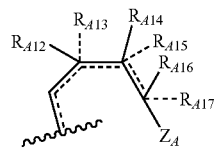

can be of the formula:

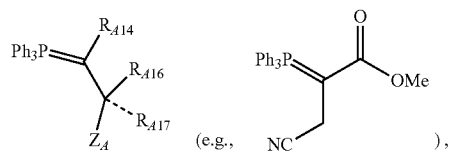

and the aldehyde or ketone moiety can couple (e.g., through a Wittig reaction) with the $Ph_3P$=moiety to form a C=C double bond, which may further be hydrogenated to form a C—C single bond.

Examples of compounds of Formula (III) include sclareolide, ambrox, γ-bicyclohomofarnesal, albicanol, larixol, and Wieland-Miescher ketone.

A compound of Formula (IV) may be converted to a compound of Formula (V). When $W_A$ is —O—, a compound of Formula (IV) may be converted to a compound of Formula (V) by olefin peroxidation. When $W_A$ is —S—, a compound of Formula (IV) may be converted to a compound of Formula (V) by olefin peroxidation followed by reacting the resulting epoxide with an alkali metal thiocyanate or thiourea. When $W_A$ is —NR″—, a compound of Formula (IV) may be converted to a compound of Formula (V) by olefin aziridination (e.g., in the presence of p-toluenesulfonamide and a transition metal catalyst; $Ph_2P$(=O)$ONH_2$; $Me_3SiCH_2CH_2SO_2N_3$ and a transition metal catalyst; $TosNCl_2$ and a transition metal catalyst; $PhI(OAc)_2$, a sulfonamide, and a transition metal catalyst; or an azide and triflic acid).

A compound of Formula (V) may be converted to a compound of Formula (VI) by a cyclization reaction, e.g., a reductive cyclization, e.g., a reductive cyclization using a metal as a reductant. The cyclization reaction may be catalyzed by a transition metal catalyst (e.g., a titanium complex or titanium salt). A desired $R_{A14}$ may be introduced by adding a corresponding reagent after the cyclization reaction, as in a general etherification reaction. The respective species of $R_{A15}$ and $G_A$ in Formula (II) will depend on the species of $Z_A$. When $Z_A$ is an aldehyde group, $R_{A15}$ can be hydrogen, and $G_A$ can be —OH or —OR″. When $Z_A$ is a thialdehyde group, $R_{A15}$ can be hydrogen, and $G_A$ can be —SH or —SR″. When $Z_A$ is a ketone group, $R_{A15}$ can be a saturated or unsaturated, substituted or unsubstituted, branched or unbranched, (hetero)aliphatic group having 1-6 carbon atoms, and $G_A$ can be —OH or —OR″. When $Z_A$ is a thione group, $R_{A15}$ can be a saturated or unsaturated, substituted or unsubstituted, branched or unbranched, (hetero)aliphatic group having 1-6 carbon atoms, and $G_A$ can be —SH or —SR″. When $Z_A$ is an ester group, an amide group, a nitrile group, or a carbamate group, $G_A$ can be =O. When $Z_A$ is a thioate group, a dithioate group or a thioamide group, $G_A$ can be =S. When $Z_A$ is a thioate group, a dithioate group or a thioamide group, $G_A$ can be =S. When $Z_A$ is an imino group, $G_A$ can be —NHR″. When $Z_A$ is an alkenyl group, or an alkynyl group, $R_{A15}$ can be a saturated or unsaturated, substituted or unsubstituted, branched or unbranched, (hetero)aliphatic group having 1-6 carbon atoms, and $G_A$ can be hydrogen.

In certain embodiments, $G_A$ can be =O or —OR".

In certain embodiments, $R_{A21}$ can be —CH$_2$OR" or an aldehyde group.

In certain embodiments, $W_A$ can be —O—.

In certain embodiments, $Z_A$ can be an amide group, an ester group, an aldehyde group, a nitrile group, an imino group, or a ketone group.

In certain embodiments, $Z_A$ can be cyano.

In certain embodiments, $Y_A$ can be =CH$_2$.

In certain embodiments, $R_{A14}$ can be alky, a carboxyl group, an ester group, or an aldehyde group.

For example, when galanal A or galanal B is to be formed, $W_A$ can be —O—; each of $X_A$ and $Y_A$ can be methylene; $Z_A$ can be cyano; $R_{A1}$ to $R_{A11}$ can be as aforementioned (e.g., $R_{A1}$ can be methyl; $R_{A2}$, $R_{A3}$, and the two carbon atoms directly bonded therewith can form a 3,3-dimethyl cyclohexane ring (e.g., 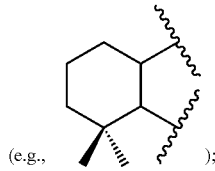 );

each of $R_{A4}$, $R_{A5}$, $R_{A6}$, $R_{A7}$, $R_{A}$, $R_{A9}$, and $R_{A10}$, can be hydrogen; and $R_{A11}$ can be an aldehyde group or —CH$_2$OR" (e.g., —CH$_2$OH)), $R_{A12}$ can be hydrogen; $R_{A13}$ can be hydrogen; $G_A$ can be =O; and the bond between the two carbon atoms directly bonded with $R_{A10}$ and $R_{A11}$ can be a double bond. In certain embodiments, $X_A$ and $Y_A$ can be each methylene; $R_{A1}$ can be methyl; $R_{A2}$, $R_{A3}$ and the two carbon atoms directly bonded therewith form a 3,3-dimethyl cyclohexane ring; $R_{A4}$, $R_{A5}$, $R_{A6}$, $R_{A7}$, $R_{A8}$, $R_{A9}$, $R_{A10}$, $R_{A12}$, and $R_{A13}$ can be hydrogen; $R_{A11}$ can be an amide group, a carboxyl group, an ester group, an aldehyde group, an alcohol group, a carbamate group, a thiocarbamate, a carbonate, a nitrile group, an amino group, an imino group; $W_A$ can be —O—; $R_{A12}$, $R_{A13}$, $R_{A14}$, and $R_{A15}$ can be hydrogen; $G_A$ can be =O; and the bond between the two carbon atoms directly bonded with $R_{A10}$ and $R_{A11}$ can be a double bond. In certain embodiments, a preparation process described herein may further include converting $G_A$ to —OH. In certain embodiments, a preparation process described herein may further include converting —CR$_{A2}$R$_{A13}$—W$_A$—R$_{A14}$ to —CHO, wherein $W_A$ is —O—, and each of $R_{A12}$, $R_{A13}$, and $R_{A14}$ is hydrogen. In certain embodiments, a preparation process described herein may further include converting $R_{A11}$ to —CHO.

The step(s) of the processes of preparing the compounds described herein may be performed under any suitable conditions. A suitable condition is a combination of physical and chemical parameters under which an intended product (e.g., a compound described herein) or intermediate may be formed using the processes. A suitable condition may include the absence of a solvent (i.e., neat). A suitable condition may include a suitable solvent. In certain embodiments, the suitable solvent can be an organic solvent. In certain embodiments, the suitable solvent can be an aprotic organic solvent (e.g., acetonitrile, N,N-dimethylformamide (DMF), N,N-dimethylacetamide (DMA), N-methyl-2-pyrrolidone (NMP), dimethyl sulfoxide (DMSO), tetrahydrofuran (THF), 2-methly-tetrahydrofuran, tetrahydropyran, dioxane, diethyl ether, methyl t-butyl ether (MTBE), dimethoxyethane (DME), diglyme, acetone, butanone, dichloromethane, chloroform, carbon tetrachloride, or 1,2-dichloroethane). In certain embodiments, the suitable solvent can be a protic organic solvent (e.g., an alcohol, such as methanol, ethanol, propanol, or butanol). In certain embodiments, the suitable solvent can be an inorganic solvent (e.g., water). In certain embodiments, the suitable solvent can be a mixture of two or more solvents. In certain embodiments, the suitable solvent can be commercially available. In certain embodiments, the suitable solvent can be toluene, benzene, diethyl ether, THF, methylcyclohexane, cyclohexene, or dichloromethane.

A suitable condition may also include a suitable temperature under which a step of a process of preparing a compound described herein is performed. In certain embodiments, the suitable temperature can be at least about 0° C., at least about 23° C., at least about 40° C., at least about 60° C., at least about 80° C., or at least about 100° C. In certain embodiments, the suitable temperature can be at most about 100° C., at most about 80° C., at most about 60° C., at most about 40° C., at most about 23° C., or at most about 0° C. Combinations of the above-referenced ranges (e.g., at least about 23° C. and at most about 80° C.) are also within the scope of the disclosure. A suitable temperature may be a variable temperature (e.g., from 23° C. to about 80° C.) during a step of a process of preparing a compound described herein.

A suitable condition may also include a suitable pressure under which a step of a process of preparing a compound described herein is performed. In certain embodiments, the suitable pressure can be about 1 atmosphere or greater than 1 atmosphere.

A suitable condition may also include a suitable atmosphere under which a step of a process of preparing a compound described herein is performed. In certain embodiments, the suitable atmosphere can be air. In certain embodiments, the suitable atmosphere can be an inert atmosphere (e.g., a nitrogen or argon atmosphere). In certain embodiments, the suitable atmosphere is a hydrogen atmosphere.

A suitable condition may also include a suitable time duration that a step of a process of preparing a compound described herein lasts. In certain embodiments, the suitable time duration can be in the order of minutes (e.g., about 10 minutes or about 30 minutes), hours (e.g., about 1 hour, about 2 hours, about 3 hours, about 4 hours, about 6 hours, or about 12 hours), or days (e.g., about 1 day or 2 days).

One or more intermediates resulting from a step of a process of preparing the compounds described herein may be isolated and/or purified, and the isolated and/or purified intermediates may be reacted in a next step of the process. The isolated and/or purified intermediates may be substantially free of impurities or may contain one or more other components, such as reagents and solvents employed in the step yielding the intermediates, and byproducts. The intermediates may also be reacted in a next step without being isolated and/or purified. The intermediates and/or intended products of a process of preparing a compound described herein may be isolated and/or purified using process known in the art, such as distillation, chromatography (e.g., normal phase chromatography (e.g., silica gel flash chromatography), reverse phase chromatography (e.g., high performance liquid chromatography (HPLC)), precipitation, decanting, filtration, centrifuge, trituration, crystallization, recrystallization, liquid-liquid phase separation, evaporation, and drying. In certain embodiments, an intended product described herein can be substantially pure (e.g., substantially free of impurities) (e.g., at least about 90%, at least about 95%, at least about 98%, at least about 99%, at least about 99.5%, at least about 99.9%, or more pure) prior to or without purification.

In certain embodiments, a process described herein can be according to the scheme:

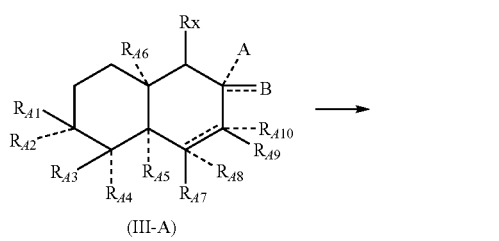
(III-A)
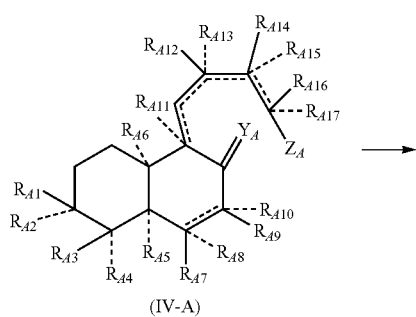
(IV-A)
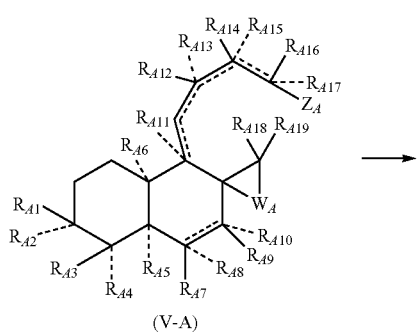
(V-A)
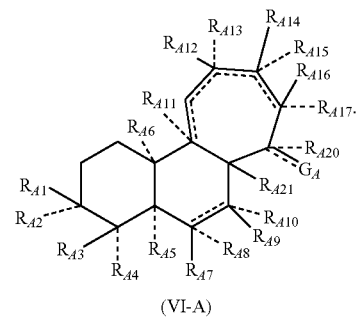
(VI-A)
In certain embodiments, a process described herein can be according to the scheme:
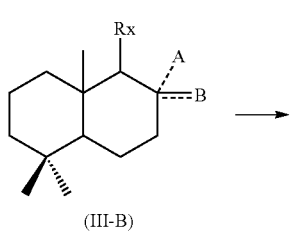
(III-B)
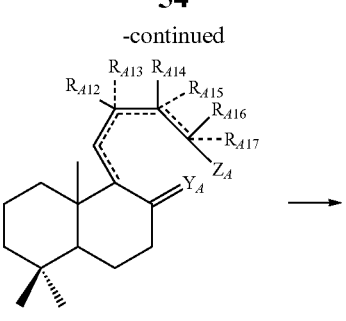
(IV-B)
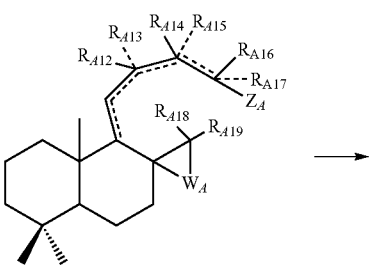
(V-B)
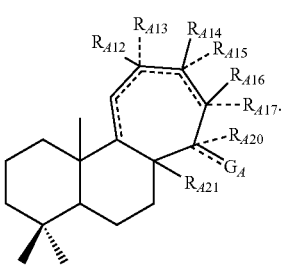
(VI-B)
In certain embodiments, a process described herein can be according to the scheme:
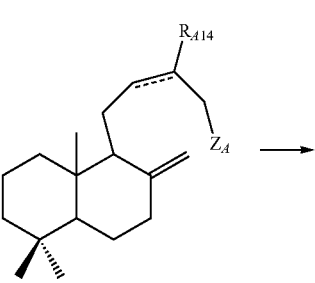
(IV-C)
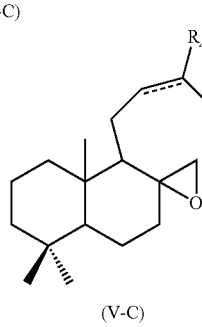
(V-C)

-continued

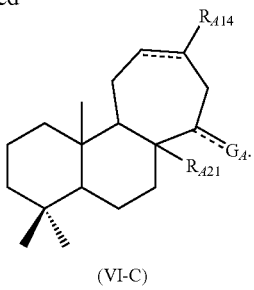

(VI-C)

IV. Pharmaceutical Compositions Comprising GLP-1 Receptor Modulators and Therapeutic Uses Thereof Any of the compounds (e.g., compounds of Formula (II) or (VI)) described herein, which can be prepared by the synthetic methods also described herein, may be useful in treating a disease mediated by GLP-1 receptor (e.g., diabetes, obesity, excessive appetite, insufficient satiety, a metabolic disorder, neurodegenarative disease, or cardiovascular disease) in a subject or in lowering blood glucose levels. In certain embodiments, the disease is treated or the blood glucose levels are lowered by a method described herein via, e.g., modulating the GLP-1 receptor signaling pathways. Such compounds can also be used in activating GLP-1 receptor in the presence of GLP-1.

A pharmaceutical composition that includes one or more compound described herein and a pharmaceutically acceptable excipient. In certain embodiments, a pharmaceutical composition described herein includes a compound described herein in an amount sufficient to treat a disease mediated by GLP-1 receptor or lower blood glucose levels in a subject. The excipient in the pharmaceutical composition must be "acceptable" in the sense that it is compatible with the active ingredient of the composition, and preferably, capable of stabilizing the active ingredient and not deleterious to the subject to be treated. For example, solubilizing agents such as cyclodextrins, which form specific, more soluble complexes with the compounds described herein, or one or more solubilizing agents, can be utilized as pharmaceutical excipients for delivery of the compounds described herein. Examples of other excipients include colloidal silicon dioxide, magnesium stearate, cellulose, sodium lauryl sulfate, and D&C Yellow #10.

To practice the methods described herein, an effective amount of a pharmaceutical composition as described herein can be administered to a subject in need of the treatment via a suitable route.

An "effective amount" is that amount of the one or more GLP-1 receptor modulator that alone, or together with further doses, produces the desired response, e.g. reduce the blood glucose levels in the subject. In the case of treating a particular disease or condition such as Type I or Type II diabetes, characterized by dysregulated GLP-1 receptor signaling, the desired response is inhibiting the progression of the disease or condition. This may involve only slowing the progression of the disease temporarily, although more preferably, it involves halting the progression of the disease permanently. This can be monitored by routine methods or can be monitored according to routine medical practices. The desired response to treatment of the disease or condition also can be delaying the onset or even preventing the onset of the disease or condition.

Effective amounts will depend, of course, on the particular condition being treated, the severity of the condition, the individual patient parameters including age, physical condition, size, gender and weight, the duration of the treatment, the nature of concurrent therapy (if any), the specific route of administration and like factors within the knowledge and expertise of the health practitioner. These factors are well known to those of ordinary skill in the art and can be addressed with no more than routine experimentation. It is generally preferred that a maximum dose of the individual components or combinations thereof be used, that is, the highest safe dose according to sound medical judgment. It will be understood by those of ordinary skill in the art, however, that a patient may insist upon a lower dose or tolerable dose for medical reasons, psychological reasons or for virtually any other reasons.

The subject to be treated by any of the methods described herein can be a human patient, e.g., a human patient having, at risk for, or suspected of having an elevated blood glucose level or any disease/condition associated therewith, such as Type I or Type II diabetes. Such a human patient can be identified by routine medical practices. Alternatively, the subject can be a non-human mammal, e.g., dog, cat, cow, pig, horse, sheep, or goat.

The terms "treatment," "treat," and "treating" refer to reversing, alleviating, delaying the onset of, or inhibiting the progress of diabetes. In some embodiments, treatment may be administered after one or more signs or symptoms have developed or have been observed. In other embodiments, treatment may be administered in the absence of signs or symptoms of diabetes. For example, treatment may be administered to a susceptible individual prior to the onset of symptoms (e.g., in light of a history of symptoms and/or in light of genetic or other susceptibility factors). Treatment may also be continued after symptoms have resolved, for example, to delay or prevent recurrence.

The pharmaceutical composition described herein can be administered orally, parenterally, by inhalation spray, topically, rectally, nasally, buccally, vaginally or via an implanted reservoir. The term "parenteral" as used herein includes subcutaneous, intracutaneous, intravenous, intramuscular, intraarticular, intraarterial, intrasynovial, intrasternal, intrathecal, intralesional and intracranial injection or infusion techniques.

A sterile injectable composition, e.g., a sterile injectable aqueous or oleaginous suspension, can be formulated according to techniques known in the art using suitable dispersing or wetting agents (such as TWEEN® 80) and suspending agents. The sterile injectable preparation can also be a sterile injectable solution or suspension in a non-toxic parenterally acceptable diluent or solvent, for example, as a solution in 1,3-butanediol. Among the acceptable vehicles and solvents that can be employed are mannitol, water, Ringer's solution and isotonic sodium chloride solution. In addition, sterile, fixed oils are conventionally employed as a solvent or suspending medium (e.g., synthetic mono- or di-glycerides). Fatty acids, such as oleic acid and its glyceride derivatives are useful in the preparation of injectables, as are natural pharmaceutically-acceptable oils, such as olive oil or castor oil, especially in their polyoxyethylated versions. These oil solutions or suspensions can also contain a long-chain alcohol diluent or dispersant, or carboxymethyl cellulose or similar dispersing agents. Other commonly used surfactants such as Tweens or Spans or other similar emulsifying agents or bioavailability enhancers which are commonly used in the manufacture of pharmaceutically acceptable solid, liquid, or other dosage forms can also be used for the purposes of formulation.

A pharmaceutical composition for oral administration can be any orally acceptable dosage form including, but not limited to, capsules, tablets, emulsions and aqueous suspensions, dispersions and solutions. In the case of tablets for oral use, excipients which are commonly used include lactose and corn starch. Lubricating agents, such as magnesium stearate, are also typically added. For oral administration in a capsule form, useful diluents include lactose and dried corn starch. When aqueous suspensions or emulsions are administered orally, the active ingredient can be suspended or dissolved in an oily phase combined with emulsifying or suspending agents. If desired, certain sweetening, flavoring, or coloring agents can be added. A nasal aerosol or inhalation composition can be prepared according to techniques well-known in the art of pharmaceutical formulation and can be prepared as solutions in saline, employing benzyl alcohol or other suitable preservatives, absorption promoters to enhance bioavailability, fluorocarbons, and/or other solubilizing or dispersing agents known in the art. A pharmaceutical composition described herein can also be administered in the form of suppositories for rectal administration.

Also within the scope of the present disclosure are kits (e.g., pharmaceutical packs) comprising a compound or pharmaceutical composition described herein. Such a kit can further comprise a container (e.g., a vial, ampule, bottle, syringe, dispenser package, or other suitable container) for placing the compounds or compositions. In some embodiments, a kit described herein may include a second container comprising a pharmaceutically acceptable excipient for dilution or suspension of a compound or pharmaceutical composition described herein. In some embodiments, the compound or pharmaceutical composition provided in the first container and the second container are combined to form one unit dosage form.

A kit described herein may include instructions for using the kit (e.g., for administering a compound or pharmaceutical composition contained therein to a subject). A kit described herein may also include information as required by a regulatory agency such as the FDA. In certain embodiments, the information included in the kit is prescribing information. A kit described herein may include one or more additional pharmaceutical agents as a separate composition.

A compound or pharmaceutical composition described herein may be administered concurrently with, prior to, or subsequent to one or more additional pharmaceutical agents, which may be useful as, e.g., combination therapies. The additional pharmaceutical agents may be therapeutically active agents or prophylactically active agents.

Without further elaboration, it is believed that one skilled in the art can, based on the above description, utilize the present invention to its fullest extent. The following specific embodiments are, therefore, to be construed as merely illustrative, and not limitative of the remainder of the disclosure in any way whatsoever. All publications cited herein are incorporated by reference for the purposes or subject matter referenced herein.

EXAMPLES

Without intent to limit the scope of the present disclosure, exemplary compounds and methods of using or making such, as well as their related results according to the embodiments of the present disclosure are given below. Note that titles or subtitles may be used in the examples for convenience of a reader, which in no way should limit the scope of the present disclosure. Moreover, certain theories are proposed and disclosed herein; however, in no way should they limit the scope of the present disclosure so long as the present disclosure is practiced according to the present disclosure without regard for any particular theory or scheme of action.

Example 1

Synthesis of Galanal A and Galanal B (RJ-21)

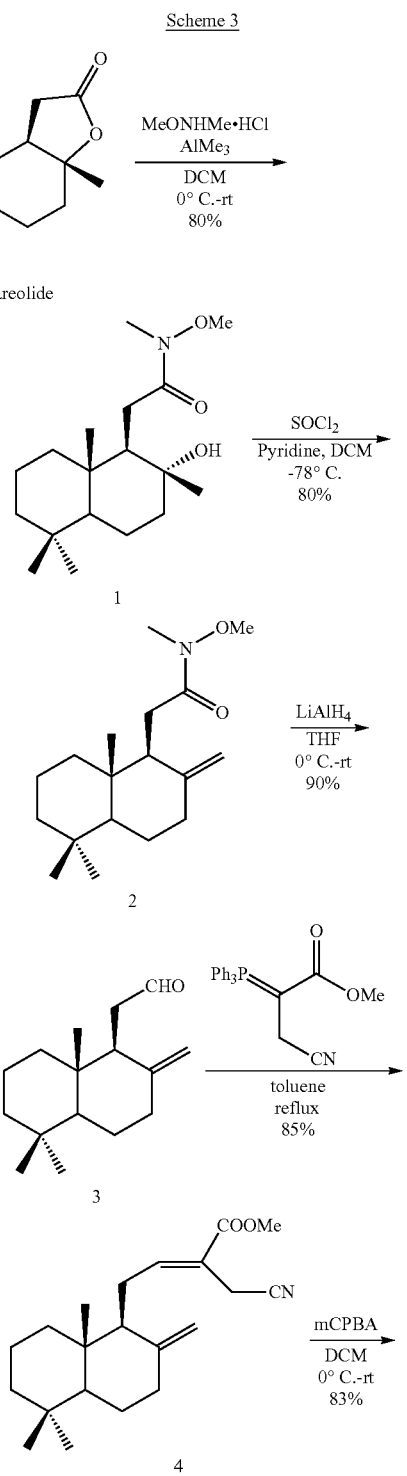

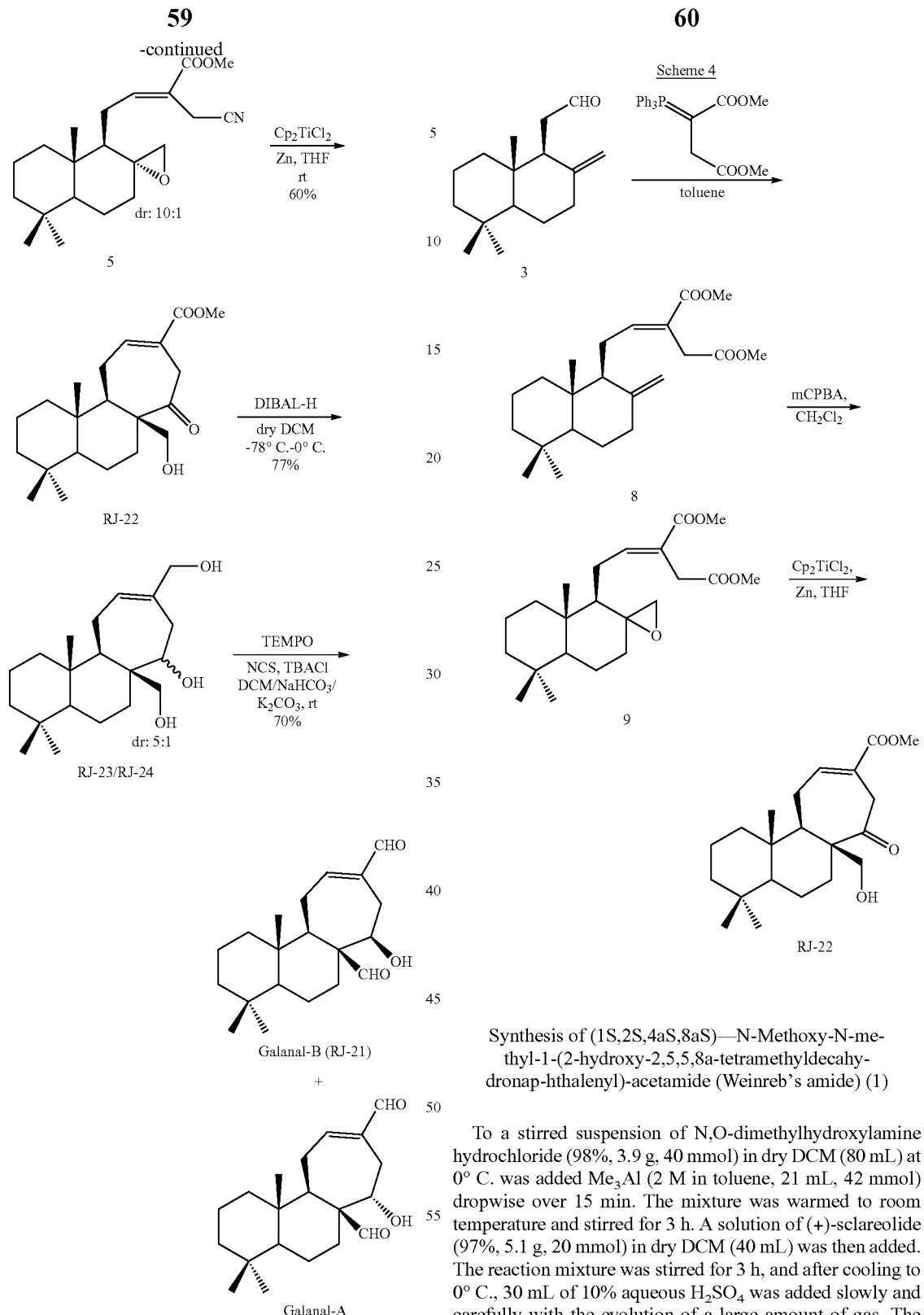

In this example, Galanal A and Galanal B (RJ-21) is synthesized according to the above Scheme 3.

Alternatively, the compound RJ-22 can be achieved by Scheme 4.

Synthesis of (1S,2S,4aS,8aS)—N-Methoxy-N-methyl-1-(2-hydroxy-2,5,5,8a-tetramethyldecahydronap-hthalenyl)-acetamide (Weinreb's amide) (1)

To a stirred suspension of N,O-dimethylhydroxylamine hydrochloride (98%, 3.9 g, 40 mmol) in dry DCM (80 mL) at 0° C. was added Me$_3$Al (2 M in toluene, 21 mL, 42 mmol) dropwise over 15 min. The mixture was warmed to room temperature and stirred for 3 h. A solution of (+)-sclareolide (97%, 5.1 g, 20 mmol) in dry DCM (40 mL) was then added. The reaction mixture was stirred for 3 h, and after cooling to 0° C., 30 mL of 10% aqueous H$_2$SO$_4$ was added slowly and carefully with the evolution of a large amount of gas. The resulting reaction mixture was allowed to warm to room temperature, and the organic layer was separated. The aqueous phase was extracted with DCM (3×40 mL). The combined organic layers were dried, filtered, and concentrated under reduced pressure. The crude residue was column chromatographed (EtOAc-hexanes, 1:1) to give amide 1 (5 g, 80%) as an amorphous solid.

Synthesis of (1S,4aS,8aS)—N-Methoxy-N-methyl1-(5,5,8a-trimethyl-2-methylenedecahydronaphthalenyl)-acetamide (2)

To a stirred solution of Weinreb amide 1 (4.2 g, 13.5 mmol) in dry DCM (60 mL) at room temperature was added dry pyridine (2.2 mL, 2.0 equiv.). After cooling to −78° C., a solution of thionyl chloride (4.9 mL, 67.5 mmol, 5 equiv.) in dry DCM (25 mL) and dry pyridine (9 mL, 8.2 equiv.) was added dropwise over 30 min. The reaction mixture was stirred for 1 h at the same temperature before quenching with saturated aqueous $NaHCO_3$ (85 mL). The reaction mixture was allowed to warm to room temperature, and the organic layer was separated. The aqueous phase was extracted with DCM (3×30 mL). The combined organic layers were washed with 5% aqueous HCl (3×20 mL) and brine, and then dried, filtered, and concentrated under reduced pressure to give the crude olefin. This crude was column chromatographed (EtOAc-hexanes, 1:9) to give amide olefin 2 (3.16 g, 80%) as an amorphous solid.

Synthesis of 13,14,15,16-tetranor-8(17)-labden-12-al (3)

To a suspension of $LiAlH_4$ (516 mg, 13.6 mmol) in THF (70 mL), under nitrogen and at 0° C., a solution of amide 2 (2 g, 6.8 mmol) in THF (100 mL) was added dropwise. The mixture was allowed to reach room temperature and it was stirred overnight. The reaction mixture was quenched by adding 10% w/v KOH solution. The mixture was filtered, the organic phase was removed, and the aqueous phase was extracted with EtOAc (3×50 mL). The combined organic extracts were dried and concentrated under reduced pressure. The residue was column chromatographed (EtOAc-hexanes, 1:49) to give (1.43 g, 90%) of pure 3 as a colorless oil.

Synthesis of (E)-methyl2-cyanomethyl-4-(1S,8aS)-5,5,8a-trimethyl-2-methylenedecahydronapthalen-1-yl)but-2-enoate (4)

Under nitrogen, to a solution of 3 (1.57 g, 6.7 mmol) in dry toluene (35 mL) was added ylide 8 (7.5 g, 20.1 mmol, 3 equiv.), and the mixture was refluxed for until the starting material was consumed (48 h). After cooling and evaporation of the volatiles, the residue was column chromatographed (EtOAc-hexanes, 1:19) to afford 4 as colorless oil (1.87 g, 85%).

Exemplary data for compound 4: $[\alpha]^{25}_D$ +5.1 (c 0.93, $CHCl_3$); $^1H$ NMR (400 MHz, $CDCl_3$) δ 6.99 (t, J=6.6 Hz, 1H), 4.86 (s, 1H), 4.35 (s, 1H), 3.78 (s, 3H), 3.47-3.33 (m, 2H), 2.51-2.38 (m, 2H), 2.36-2.23 (m, 1H), 2.03 (td, J=13.0, 5.2 Hz, 1H), 1.90 (d, J=11.3 Hz, 1H), 1.78-1.71 (m, 2H), 1.60 (dt, J=6.8, 3.1 Hz, 1H), 1.42 (d, J=14.7 Hz, 1H), 1.37-1.29 (m, 2H), 1.24-1.06 (m, 3H), 0.89 (s, 3H), 0.83 (s, 3H), 0.75 (s, 3H) ppm; $^{13}C$ NMR (100 MHz, $CDCl_3$) δ 165.8, 149.5, 148.0, 121.3, 116.7, 107.7, 56.4, 55.4, 52.3, 42.0, 39.6, 39.3, 37.8, 33.6, 24.4, 24.1, 21.7, 19.3, 15.4, 14.4 ppm; IR (film) 2937, 2844, 2249, 1714, 1644, 1437, 1388, 1366, 1213, 1118, 1057, 973, 891, 830, 735 $cm^{-1}$; HRMS m/z (ESI+) calculated for $C_{21}H_{31}NO_2Na$ $[(M+Na)^+]$352.2252. Found 352.2244.

Synthesis of (E)-methyl2-(cyanomethyl)-4-((1R,2R,8aS)-5,5,8a-trimethyloctahydro-1H-spiro[naphthalene-2,2′-oxiran]-1-yl)but-2-enoate (5)

To the stirred solution of olefin 4 (1.5 g, 4.55 mmol) in $CH_2Cl_2$ (12 mL) was added 70% of mCPBA (1.57 g, 9.1 mmol) in $CH_2Cl_2$ (10 mL) at 0° C., and the mixture was stirred for 6 h at room temperature. After completion of the reaction, the mixture was diluted with 10% aqueous $Na_2SO_3$ solution (5 mL) and extracted with $CH_2Cl_2$ (2×25 mL). The organic layer was washed with saturated $NaHCO_3$ solution (2×10 mL), brine, dried over $Na_2SO_4$, concentrated, and column chromatographed (EtOAc-hexanes, 1:9) to furnish 5 as colorless oil (1.25 g, 80%).

Exemplary data for compound 5: $[\alpha]^{25}_D$ −10.7 (c 1, $CHCl_3$); $^1H$ NMR (400 MHz, $CDCl_3$) δ 7.08 (t, J=7.4 Hz, 1H), 3.79 (s, 3H), 3.38 (s, 2H), 2.72 (dd, J=4.0, 2.0 Hz, 1H), 2.58 (d, J=4.0 Hz, 1H), 2.10-2.01 (m, 1H), 1.96-1.81 (m, 3H), 1.73 (t, J=5.5 Hz, 1H), 1.66-1.58 (m, 2H), 1.52-1.39 (m, 4H), 1.18 (td, J=13.2, 4.1 Hz, 1H), 1.10-1.01 (m, 2H), 0.91 (s, 3H), 0.88 (s, 3H), 0.85 (s, 3H) ppm; $^{13}C$ NMR (100 MHz, $CDCl_3$) δ 165.9, 149.8, 120.4, 117.1, 58.6, 54.9, 54.4, 52.3, 50.5, 41.7, 40.1, 39.4, 35.9, 33.4, 33.3, 21.9, 21.6, 21.6, 18.6, 15.1, 14.5 ppm; IR (film) 2918, 2848, 2249, 1713, 1650, 1462, 1435, 1389, 1367, 1293, 1214, 1116, 1057, 974 $cm^{-1}$; HRMS m/z (ESI+) calculated for $C_{21}H_{31}NO_3Na$ $[(M+Na)^+]$368.2202. Found 368.2196.

Synthesis of (6aR,11aR,11bS)-methyl6a-(hydroxymethyl)-4,4,11b-trimethyl-7-oxo-2,3,4,4a,5,6,6a,7,8,11,11a,11b-dodecahydro-1H-cyclohepta[a]naphthalene-9-carboxylate (RJ-22) according to Scheme 3

A mixture of bis(cyclopentadienyl)titanium(IV) dichloride ($Cp_2TiCl_2$) (794 mg, 2.20 equiv.) and Zinc powder (625 mg, 6.60 equiv) in deoxygenated THF (14 mL) was stirred at room temperature (30 min) until the red solution turned green. The resulting green Ti(III) solution was slowly added via cannula to the stirred solution of epoxy nitrile 5 (500 mg, 1.45 mmol) in THF (15 mL), and the resulting mixture was stirred for 12 h. After this, an excess of saturated $NaH_2PO_4$ was added, and the mixture was stirred for 30 min. The mixture was filtered to remove insoluble titanium salts. The product was extracted into ether (3×30 mL), and the combined organic layers were washed with saturated $NaHCO_3$ (20 mL) and brine, dried over $Na_2SO_4$, concentrated, and the crude product was column chromatographed (EtOAc-hexanes, 1:9) to afford ketone, RJ-22 as colorless needles (302 mg, 60%).

Exemplary data for compound RJ-22: $[\alpha]^{25}_D$ −21.1 (c 0.93, $CHCl_3$); mp 179-180° C.; $^1H$ NMR (400 MHz, $CDCl_3$) δ 7.07 (dt, J=6.2, 3.1 Hz, 1H), 4.14-3.98 (m, 2H), 3.93 (ddd, J=13.9, 6.7, 2.8 Hz, 1H), 3.74 (s, 3H), 3.49 (d, J=13.9 Hz, 1H), 2.80 (dd, J=8.0, 5.8 Hz, 1H), 2.65-2.44 (m, 2H), 2.18 (dd, J=11.8, 2.1 Hz, 1H), 2.02-1.95 (m, 1H), 1.81 (d, J=12.4 Hz, 1H), 1.66 (ddd, J=14.0, 8.7, 3.8 Hz, 2H), 1.53-1.34 (m, 5H), 1.18 (td, J=13.5, 4.1 Hz, 2H), 0.95 (s, 3H), 0.88 (s, 3H), 0.82 (s, 3H) ppm; $^3C$ NMR (100 MHz, $CDCl_3$) δ 214.6, 167.0, 143.7, 124.3, 63.3, 56.8, 56.5, 52.2, 50.6, 41.6, 39.8, 37.9, 37.7, 33.4, 33.1, 32.4, 26.3, 21.3, 18.4, 18.1, 16.1 ppm; IR (film) 3542, 2935, 1708, 1702, 1640, 1440, 1386, 1263, 1165, 1115, 1060, 753 $cm^{-1}$; HRMS m/z (FAB+) calculated for $C_{21}H_{33}O_4$ $[(M+H)^+]$349.2379. Found 349.2380.

Synthesis of (6aR,11aR,11bS)-methyl6a-(hydroxymethyl)-4,4,11b-trimethyl-7-oxo-2,3,4,4a,5,6,6a,7,8,11,11a,11b-dodecahydro-1H-cyclohepta[a]naphthalene-9-carboxylate (RJ-22) according to Scheme 4

A mixture of $Cp_2TiCl_2$ (71 mg, 2.20 equiv.) and Zinc powder (56 mg, 6.60 equiv) in deoxygenated THF (1.2 mL) was stirred at room temperature (30 min) until the red solution turned green. The resulting green Ti(III) solution was slowly added via cannula to the stirred solution of epoxy ester 9 (50 mg, 0.13 mmol) in THF (1.5 mL), and the resulting mixture was stirred for 6 h. After this, an excess of saturated $NaH_2PO_4$ was added, and the mixture was stirred for 30 min. The mixture was filtered to remove insoluble titanium salts. The product was extracted into ether (3×10 mL), and the combined organic layers were washed with saturated $NaHCO_3$ (10 mL) and brine, dried over $Na_2SO_4$, concentrated, and the crude product was column chromatographed (EtOAc-hexanes, 1:9) to afford ketone RJ-22 as colorless needles.

Synthesis of ((6aR,7R,11aR,11bS)-7-hydroxy-4,4, 11b-trimethyl-2,3,4,4a,5,6,6a,7,8,11,a,11b-dodecahydro-1H-cyclohepta[a]naphthalene-6a,9-diyl)dimethanol (RJ-23/RJ-24)

To a stirred solution of RJ-22 (200 mg, 0.57 mmol) in dry $CH_2Cl_2$ (3 mL) at −78° C. was added DIBAL-H (1 M in toluene, 4.5 mL) slowly under nitrogen atmosphere. The resulting solution was stirred at −78° C. for 2 h and slowly warmed to 0° C. for 6 h before quenching with 10% aqueous HCl (5 mL). The resulting mixture was allowed to warm to room temperature, and the organic layer was separated. The aqueous phase was extracted with $CH_2Cl_2$ (3×20 mL). The combined organic layers were washed with brine, dried over $Na_2SO_4$, concentrated, and the resulting residue was column chromatographed (EtOAc-hexanes, 1:1) to give (140 mg, 77%) of triol RJ-23/RJ-24 as white solid.

Exemplary data for compound RJ-23/RJ-24: $[\alpha]^{25}_D$ −25.3 (c 0.53, $CHCl_3$); mp 169-171° C.; $^1$H NMR (400 MHz, $CDCl_3$) δ 5.89 (dd, J=8.1, 3.3 Hz, 1H), 4.21 (d, J=11.2 Hz, 1H), 3.99 (s, 2H), 3.95 (d, J=11.3 Hz, 1H), 3.53 (d, J=8.3 Hz, 1H), 2.87 (brs, 1H), 2.69 (dd, J=16.2, 8.6 Hz, 2H), 2.45 (d, J=16.3 Hz, 1H), 2.26 (dt, J=13.3, 3.2 Hz, 1H), 2.21-2.09 (m, 1H), 2.04 (dd, J=16.8, 8.2 Hz, 1H), 1.76 (d, J=12.5 Hz, 1H), 1.67-1.51 (m, 2H), 1.48-1.24 (m, 5H), 1.14 (dd, J=13.3, 4.1 Hz, 1H), 1.11-0.97 (m, 1H), 0.86 (s, 3H), 0.79 (s, 3H), 0.75 (s, 3H) ppm; $^{13}$C NMR (100 MHz, $CDCl_3$) δ 136.7, 129.2, 79.5, 68.5, 62.6, 56.4, 56.1, 46.4, 41.9, 39.7, 38.4, 33.8, 33.4, 33.3, 33.2, 22.7, 21.3, 18.7, 18.5, 16.2 ppm; IR (film) 3381, 2923, 2358, 1650, 1455, 1385, 1005, 966, 732 cm$^{-1}$; HRMS m/z (ESI+) calculated for $C_{20}H_{34}O_3Na$ [(M+Na)$^+$] 345.2406. Found 345.2398.

Synthesis of (E)-dimethyl2-(2-((1S,8aS)-5,5,8a-trimethyl-2-methylene-decahydronaphthalen-1-yl)ethylidene)succinate (8)

Under nitrogen, to a solution of 3 (340 mg, 1.45 mmol) in dry toluene (8 mL) was added ylide (2.3 g, 5.8 mmol, 4 equiv.), and the mixture was refluxed for 72 h. After cooling and evaporation of the volatiles, the residue was column chromatographed (EtOAc-hexanes, 1:19) to afford 8 as colorless product (420 mg, 80%).

Synthesis of (E)-dimethyl2-(2-((1R,2R,8aS)-5,5,8a-trimethyloctahydro-1H-spiro[naphthalene-2,2'-oxiran]-1-yl)ethylidene)succinate (9)

To the stirred solution of olefin 8 (100 mg, 0.27 mmol) in $CH_2Cl_2$ (1 mL) was added 70% of mCPBA (93 mg, 0.54 mmol) in $CH_2Cl_2$ (1 mL) at 0° C., and the mixture was stirred for 6 h at room temperature. After completion of the reaction, the mixture was diluted with 10% aq. $Na_2SO_3$ solution (2 mL) and extracted with $CH_2Cl_2$ (2×10 mL). The organic layer was washed with saturated $NaHCO_3$ solution (2×5 mL), brine, dried over $Na_2SO_4$, concentrated, and column chromatographed (EtOAc-hexanes, 1:9) to furnish 9 as colorless oil (83 mg, 80%).

Exemplary data for compound 9: $[\alpha]^{25}_D$ −1.1 (c 1, $CHCl_3$); IR (film) 2948, 1770, 1712, 1680, 1433, 1383, 1273, 1205, 1159, 1118, 1085, 998, 736, 677 cm$^{-1}$; $^1$H NMR (400 MHz, $CDCl_3$) δ 6.99 (t, J=7.3 Hz, 1H), 3.72 (s, 3H), 3.67 (s, 3H), 3.34 (s, 2H), 2.67 (dd, J=4.1, 1.9 Hz, 1H), 2.53 (d, J=4.2 Hz, 1H), 1.99-1.74 (m, 4H), 1.71 (t, J=5.4 Hz, 1H), 1.58-1.36 (m, 6H), 1.17 (td, J=13.2, 4.0 Hz, 1H), 1.08-0.98 (m, 2H), 0.89 (s, 3H), 0.84 (s, 3H), 0.83 (s, 3H) ppm; $^{13}$C NMR (100 MHz, $CDCl_3$) δ 171.3, 167.5, 147.9, 123.8, 67.9, 58.6, 54.9, 54.2, 51.9, 50.5, 41.7, 40.1, 39.3, 36.0, 33.4, 33.3, 32.1, 25.6, 21.7, 21.6, 18.6, 14.5 ppm; HRMS m/z (ESI+) calculated for $C_{21}H_{34}O_4Na$ [(M+Na)$^+$] 401.2304. Found 401.2313.

Synthesis of Galanal B (RJ-21) & Galanal A

A solution of RJ-23/RJ-24 (100 mg, 0.31 mmol), 2,2,6,6-tetramethyl-1-piperidinyloxy, free radical, 2,2,6,6-Tetramethylpiperidine 1-oxyl (TEMPO) (9.7 mg, 0.062 mmol), tetrabutylammonium chloride (TBACl) (17.2 mg, 0.062 mmol), and an appropriate amount of an internal standard in 3 mL of dichloromethane and 3 mL of an aqueous solution of $NaHCO_3$ (0.5 M) and $K_2CO_3$ (0.05 M) were vigorously stirred at room temperature, solid N-chlorosuccinimide (NCS) (165 mg, 4 equiv.) was then added to the above mixture. Stirring was continued until the completion of the reaction monitored by TLC. After 6 h, the reaction mixture was quenched with saturated $NH_4Cl$ solution and the organic layer was separated, and the aqueous phase was extracted with $CH_2Cl_2$ (3×10 mL). The organic extracts were washed with brine, dried over $Na_2SO_4$, and the residue was column chromatographed (EtOAc-hexanes, 1:9) to separate Galanal B and Galanal A as colorless needles.

Exemplary data for Galanal B (RJ-21): $[\alpha]^{25}_D$ −71.4 (c 0.97, $CHCl_3$); mp 148-158° C.; $^1$H NMR (400 MHz, $CDCl_3$) δ 10.21 (s, 1H), 9.41 (s, 1H), 7.04 (dd, J=8.4, 4.1 Hz, 1H), 3.54 (dd, J=8.2, 4.2 Hz, 1H), 3.20-3.05 (m, 1H), 2.92 (dd, J=16.3, 9.0 Hz, 1H), 2.68 (d, J=16.3 Hz, 1H), 2.57 (dd, J=20.8, 11.8, 5.8 Hz, 2H), 1.87 (d, J=12.7 Hz, 1H), 1.78 (d, J=4.9 Hz, 1H), 1.70-1.63 (m, 1H), 1.52-1.43 (m, 2H), 1.44-1.36 (m, 1H), 1.30 (ddd, J=16.8, 13.4, 4.2 Hz, 2H), 1.20-1.07 (m, 2H), 0.90 (dd, J=13.0, 4.1 Hz, 1H), 0.86 (s, 3H), 0.79 (s, 3H), 0.78 (s, 3H) ppm; $^{13}$C NMR (125 MHz, $CDCl_3$) δ 208.1, 193.4, 157.6, 140.7, 78.7, 55.6, 55.5, 55.4, 41.6, 38.9, 38.8, 34.4, 33.4, 33.3, 28.7, 24.1, 21.3, 19.1, 18.6, 15.9 ppm; IR (film) 3457, 2917, 2848, 1710, 1673, 1644, 1462, 1384, 1260, 1090, 1024, 800 cm$^{-1}$; HRMS m/z (ESI+) calculated for $C_{20}H_{30}O_3Na$ [(M+Na)$^+$] 341.2093. Found 341.2095.

Data for Galanal A: $[\alpha]^{25}_D$ −65.3 (c 0.83, $CHCl_3$); mp 169-175° C.; $^1$H NMR (400 MHz, $CDCl_3$) δ 10.11 (s, 1H), 9.38 (s, 1H), 6.89 (dd, J=8.2, 2.0 Hz, 1H), 4.08-4.04 (m, 1H), 2.83-2.74 (m, 1H), 2.69-2.58 (m, 2H), 2.49 (dd, J=18.6, 8.3 Hz, 1H), 2.30-2.24 (m, 1H), 1.82-1.74 (m, 2H), 1.61 (d, J=10.3 Hz, 1H), 1.59-1.56 (m, 1H), 1.53-1.49 (m, 2H), 1.47-1.37 (m, 3H), 1.21-1.10 (m, 1H), 0.94-0.89 (m, 1H), 0.88 (s, 3H), 0.80 (s, 3H), 0.78 (s, 3H) ppm; $^{13}$C NMR (100 MHz, $CDCl_3$) δ 206.5, 193.3, 156.1, 142.3, 71.3, 55.7, 55.5, 53.6, 41.7, 38.6, 38.5, 33.4, 33.2, 28.4, 27.6, 23.6, 21.3, 18.6, 18.4, 16.6 ppm; IR (film) 3467, 2921, 2844, 1710, 1673, 1632, 1292, 1111, 1084, 989, 830 cm$^{-1}$; HRMS m/z (ESI−) calculated for $C_{20}H_{29}O_3$ [(M−H)$^+$] 317.2117. Found 317.2110.

Example 2

Synthesis of Exemplary Galanal Analogues

Synthesis of RJ 27 and RJ 30

Galanal analogues RJ 27 and RJ 30 were synthesized according to Scheme 5.

RJ-31/RJ-32: To a solution of RJ-22 (100 mg, 0.28 mmol) in anhyd. MeOH (1.2 mL) at 0° C., was added NaBH$_4$ (5.3 mg, 0.14 mmol) and the mixture was stirred for until the starting material was consumed (3 h). After completion of reaction (TLC), the reaction mixture was worked it up by adjusting pH (5-6) by 1N HCl drop wise and methanol was removed under reduced pressure. The residue was and then dissolved in CH$_2$Cl$_2$ (10 mL) and washed with H$_2$O (5 mL) and brine solution (5 mL). Solvent was removed and the crude compound was column chromatographed (EtOAc-hexanes, 1:4) to afford two diasteromeric separable alcohols.

Data for major isomer RJ-31: $^1$H NMR (400 MHz, CDCl$_3$) δ 7.21 (dd, J=8.5, 3.8 Hz, 1H), 4.23 (dd, J=11.3, 1.5 Hz, 1H), 3.99 (d, J=11.3 Hz, 1H), 3.73 (s, 3H), 3.54 (dd, J=8.9, 1.4 Hz, 1H), 3.02 (dd, J=16.5, 8.9 Hz, 1H), 2.82 (d, J=16.6 Hz, 1H), 2.31 (dt, J=13.5, 3.3 Hz, 2H), 2.16 (dd, J=16.9, 8.8 Hz, 2H), 1.75 (d, J=12.7 Hz, 1H), 1.67-1.51 (m, 2H), 1.47-1.34 (m, 3H), 1.30-1.24 (m, 2H), 1.16-0.99 (m, 2H), 0.86 (s, 3H), 0.79 (s, 3H), 0.77 (s, 3H). $^{13}$C NMR (101 MHz, CDCl$_3$) δ 168.3, 146.1, 129.9, 79.5, 62.5, 56.4, 55.6, 51.9, 46.5, 41.8, 39.8, 38.5, 33.8, 33.4, 33.2, 31.2, 23.6, 21.3, 18.6, 18.4, 16.2.

RJ-27/RJ-30: A solution of RJ-31/RJ-32 (40 mg, 0.11 mmol), TEMPO (1.7 mg, 0.011 mmol), TBACl (3.1 mg, 0.011 mmol), and an appropriate amount of an internal standard in 1.1 mL of dichloromethane and 1.1 mL of an aqueous solution of NaHCO$_3$ (0.5 M) and K$_2$CO$_3$ (0.05 M) were vigorously stirred at room temperature, NCS (29 mg, 2 equiv.) was then added to the above mixture. Stirring was continued until the completion of the reaction monitored by TLC. After 3 h, the reaction mixture was quenched with saturated NH$_4$Cl solution and the organic layer was separated, and the aqueous phase was extracted with CH$_2$Cl$_2$ (2×10 mL). The organic extracts were washed with brine, dried over Na$_2$SO$_4$ and the residue was column chromatographed (EtOAc-hexanes, 1:9) to obtain RJ-27/RJ-30 as white solid (80%).

Data for RJ-27: mp 114-116° C. IR (film) 3458, 2945, 1710, 1644, 1436, 1385, 1264, 1201, 1094, 971, 754, 724 cm$^{-1}$. $^1$H NMR (400 MHz, CDCl$_3$) δ 10.25 (s, 1H), 7.29 (dd, J=8.3, 5.1 Hz, 1H), 3.74 (s, 3H), 3.48 (d, J=9.2 Hz, 1H), 3.05 (dd, J=16.0, 9.7 Hz, 1H), 2.98-2.85 (m, 1H), 2.79 (d, J=16.0 Hz, 1H), 2.68-2.54 (m, 1H), 2.36 (dd, J=15.9, 8.9 Hz, 1H), 1.85 (d, J=12.8 Hz, 2H), 1.68-1.54 (m, 3H), 1.54-1.44 (m, 2H), 1.43-1.36 (m, 2H), 1.28 (ddd, J=26.2, 13.2, 3.1 Hz, 2H), 1.13 (td, J=13.3, 4.0 Hz, 2H), 0.86 (s, 3H), 0.77 (s, 3H), 0.76 (s, 3H). $^{13}$C NMR (101 MHz, CDCl$_3$) δ 208.6, 167.8, 146.3, 130.1, 78.9, 55.9, 55.5, 55.4, 52.0, 41.7, 38.8, 38.7, 34.8, 33.3, 33.2, 32.3, 23.1, 21.3, 19.0, 18.6, 15.8. HRMS (ES−) calcd for $C_{21}H_{31}O_4$ [(M−H)$^+$] 347.2222. Found 347.2223.

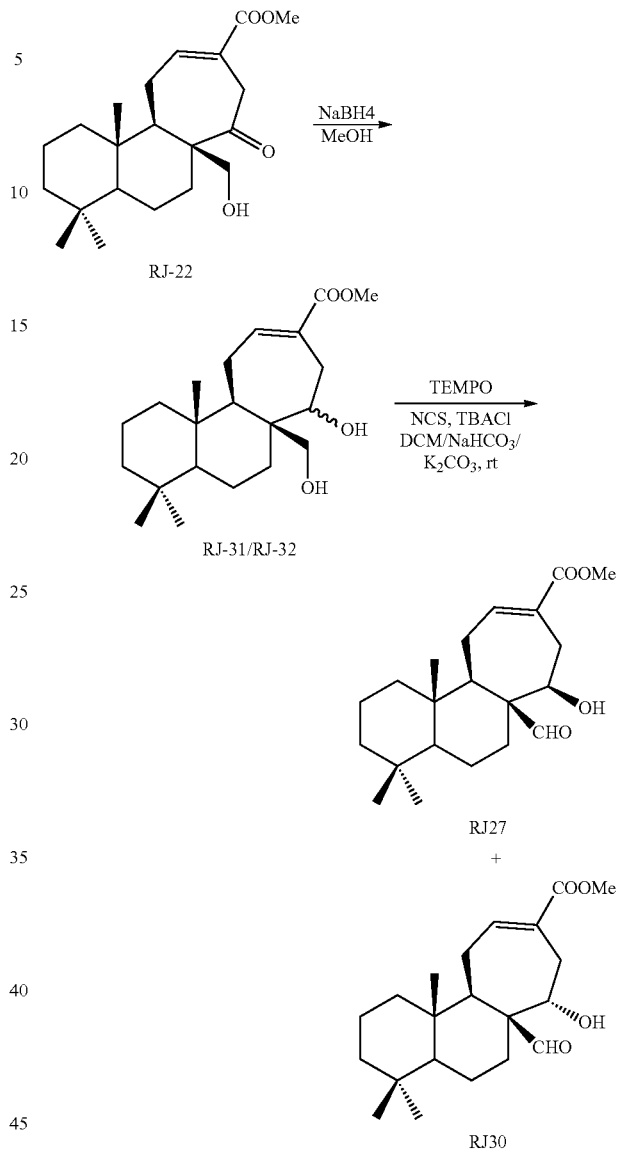

Scheme 5

Syntheses of RJ 28 and RJ 31

Galanal analogues RJ 28 and RJ 31 were synthesized according to Scheme 6.

RJ-28/RJ-31: A solution of RJ-23/RJ-24 (32 mg, 0.1 mmol), TEMPO (1.5 mg, 0.01 mmol), TBACl (2.8 mg, 0.01 mmol), and an appropriate amount of an internal standard in 1 mL of dichloromethane and 1 mL of an aqueous solution of NaHCO$_3$ (0.5 M) and K$_2$CO$_3$ (0.05 M) were vigorously stirred at room temperature, NCS (20 mg, 1.5 equiv.) was then added to the above mixture. Stirring was continued until the completion of the reaction monitored by TLC. After 3 h, the reaction mixture was quenched with saturated NH$_4$Cl solution and the organic layer was separated, and the aqueous phase was extracted with CH$_2$Cl$_2$ (2×10 mL). The organic extracts were washed with brine, dried over Na$_2$SO$_4$ and the residue was column chromatographed (EtOAc-hexanes, 1:4) to obtain RJ-028/RJ-31 as white solid (50%).

Data for RJ-GLA-028: mp ° C. IR (film) 3417, 2923, 1681, 1644, 1387, 1200, 1114, 970, 736 cm$^{-1}$. $^1$H NMR (400 MHz, CDCl$_3$) δ 9.39 (s, 1H), 6.95 (dd, J=8.3, 3.4 Hz, 1H), 4.18 (d, J=11.2 Hz, 1H), 4.00 (d, J=11.2 Hz, 1H), 3.60 (d, J=7.4 Hz, 1H), 2.90 (dd, J=16.8, 8.5 Hz, 1H), 2.69 (d, J=16.9 Hz, 1H), 2.58-2.47 (m, 1H), 2.37 (dd, J=17.6, 8.4 Hz, 1H), 2.22 (dt, J=13.3, 3.1 Hz, 1H), 1.78 (d, J=12.6 Hz, 1H), 1.70-1.53 (m, 4H), 1.43 (dd, J=19.5, 9.0 Hz, 3H), 1.35 (d, J=9.6 Hz, 2H), 1.15 (dd, J=13.4, 4.1 Hz, 1H), 1.11-1.00 (m, 1H), 0.87 (s, 3H), 0.81 (s, 6H). $^{13}$C NMR (100 MHz, CDCl$_3$) 194.0, 158.0, 140.6, 78.7, 68.4, 62.5, 56.4, 55.6, 41.9, 41.8, 39.8, 33.5, 33.4, 33.1, 27.4, 24.7, 21.3, 18.6, 18.4, 16.2. HRMS (ES−) calcd for C$_{20}$H$_{31}$O$_3$ [(M−H)$^+$] 319.2273. Found 319.2285.

residue was column chromatographed (EtOAc-hexanes, 1:11) to obtain RJ-29 as white solid (80%).

Data for RJ-29: mp 86-88° C. IR (film) 2948, 1727, 1693, 1645, 1437, 1389, 1366, 1258, 1115, 1064, 733 cm$^{-1}$. $^1$H NMR (400 MHz, CDCl$_3$) δ 9.84 (d, J=1.0 Hz, 1H), 7.16 (dt, J=6.3, 3.1 Hz, 1H), 3.92-3.80 (m, 1H), 3.75 (d, J=6.6 Hz, 3H), 3.54 (d, J=14.2 Hz, 1H), 2.89-2.65 (m, 2H), 2.40-2.26 (m, 2H), 1.84-1.70 (m, 2H), 1.68-1.58 (m, 1H), 1.53-1.39 (m, 4H), 1.18 (td, J=13.4, 4.3 Hz, 1H), 1.01-0.92 (m, 2H), 0.89 (s, 3H), 0.79 (s, 3H), 0.75 (s, 3H). $^{13}$C NMR (101 MHz, CDCl$_3$) δ 206.2, 199.6, 166.6, 142.6, 125.0, 66.5, 55.4, 52.4, 51.4, 41.6, 38.8, 38.2, 37.6, 33.3, 33.2, 31.2, 25.5, 21.3, 18.8, 18.5, 15.2. HRMS (ES−) calcd for C$_{21}$H$_{29}$O$_4$ [(M−H)$^+$] 345.2066. Found 345.2059.

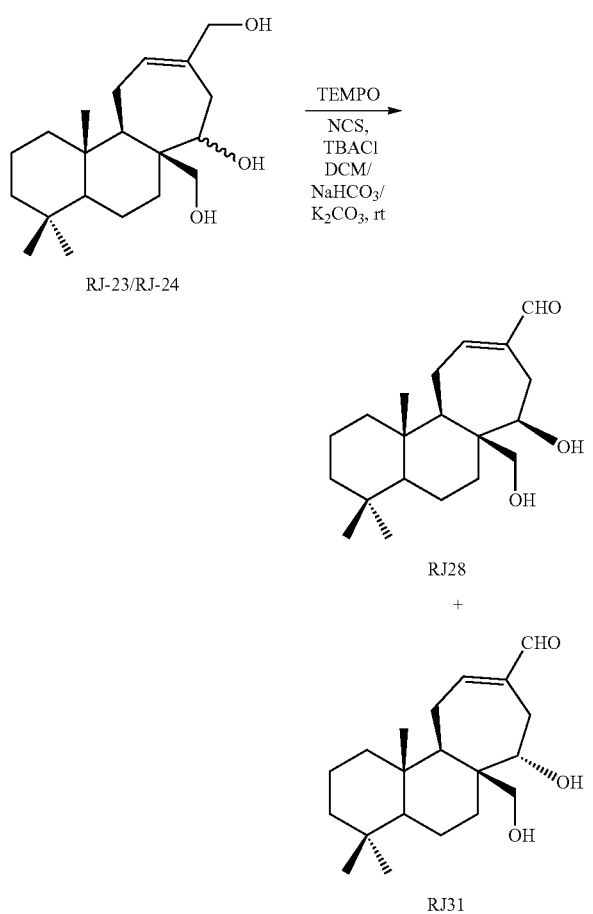

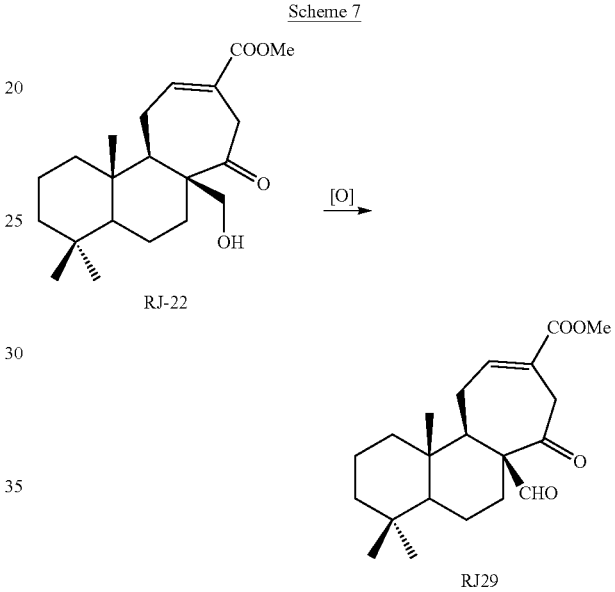

Synthesis of RJ 29

Galanal analogues RJ 29 was synthesized according to Scheme 7.

RJ-29: A solution of RJ-22 (40 mg, 0.11 mmol) in DCM (1 mL) was treated with Dess Martin periodinane (70 mg, 0.16 mmol), which was added in portions at room temperature. After being stirred for 1 h, the mixture was diluted with saturated aqueous Na$_2$S$_2$O$_3$ (1 mL) and NaHCO$_3$ (1 mL) were added. The resulting mixture was stirred vigorously for 30 min and the layers were separated. The aqueous phase was extracted with CH$_2$Cl$_2$ and the combined organic extracts were washed with brine and concentrated under vacuum. The As indicated by the above examples, by using the compounds represented by Formula (I) of this disclosure as a precursor, Galanal A and Galanal B or a Galanal analogue can be easily obtained in a high yield.

This disclosure has been disclosed above in the preferred embodiments, but is not limited to those. It is known to persons skilled in the art that some modifications and innovations may be made without departing from the spirit and scope of this disclosure. Hence, the scope of this disclosure should be defined by the following claims.

Example 3

In-Vitro Biological Assays

I. Material and Methods

A. Cell Culture

RIN-m5F cells were seeded at a density of 80,000 cells per well (96 well plate) in 90% RPMI 1640 medium with 2 mM L-glutamine containing 1.5 g/L sodium bicarbonate, 4.5 g/L glucose, 10 mM HEPES, 1.0 mM sodium pyruvate and 10% fetal bovine serum. The cells were cultured in 37° C. with 5% CO$_2$ for 42 hours prior to cAMP production experiment.

B. Stimulation of cAMP Generation by GLP-1 and Compound Galanal B(RJ-21)

Prior to GLP-1 treatment, cells were pre-incubated with fresh 0.15 ml/well of stimulation phenol red free medium containing 0.1% (W/W) bovine serum albumin, 5 mM HEPES pH 7.0, 1% DMSO and 0.5 mM IBMX at room temperature for 10 min. After removing the pre-incubation medium, 0.1 ml per well of stimulation medium containing indicated concentration of GLP-1 (3 nM, 30 nM and 300 nM) of and/or compound RJ21 (0.001 mg/ml) were incubated at room temperature for 15 min to stimulate the production of cAMP. The stimulation process was terminated by replacing the stimulation medium with 0.05 ml per well of ice-cold absolute ethanol, and further incubated at −20° C. for 20 min. The cellular cAMP was extracted with 0.085 ml PBS after the ethanol in the wells were evaporated in a vacuum desiccator for 35 min.

C. Determination of Cellular cAMP

The total cAMP from each well was determined by ELISA method according the procedure recommended by the supplier. Exemplary results are shown in FIG. 1.

II. Exemplary Results

It has been shown that GLP-1 receptor activation leads to Gαs coupling and the consequent production of intracellular cAMP, to delineate the effect of RJ21 on GLP-1 receptor activation the following hypoglycemic effect, the effect of RJ21 on the ability of GLP-1 to activate GLP-1 receptor-Gαs signaling was examined. As shown in FIG. 1, GLP-1 dose dependently stimulated RIN-m5F cells to produce cAMP, and the maximal production of cAMP was reached as GLP-1 concentration increased to 300 nM. By itself, compound RJ21 did not affect RIN-m5F cells to generate cAMP as little cAMP response was found at 3 nM of GLP-1, instead it potentiated the cAMP production by GLP-1. The maximal potential effect of compound RJ21 on GLP-1 dependent cAMP production was found at 30 nM of GLP-1, 0.001 mg/ml of compound RJ21 potentiate the effect of GLP-1 by a factor of 2. This observation shows that RJ21 is not an agonist on GLP-1 receptor signaling, revealed that RJ21 may act as a positive modulator on GLP-1 stimulated cAMP production by RIN-m5F cells.

Example 4

In-Vivo Biological Assays

I. Material and Methods

DIO mice were male C56BL/6J-Narl mice at age of 13 to 15 weeks that have been fed with Western Diet (TestDiet 5342) for 6 to 8 weeks. DIO mice were fasted for five hours and then gavaged with a compound described herein (e.g., compounds RJ21 and RJ27) at indicated dose or with vehicle alone. Thirty minutes later, the mice were gavaged with glucose (2 g/kg body weight). The level of blood glucose was measured right before and every 30 minutes after the glucose challenge up to 90 minutes. The data are expressed as mean±SD and analyzed by Student's t-test using Prism (GraphPad).

II. Exemplary Results

The compounds described herein displayed hypoglycemic effect on diet-induced obese (DIO) mice.

Figure 2A:
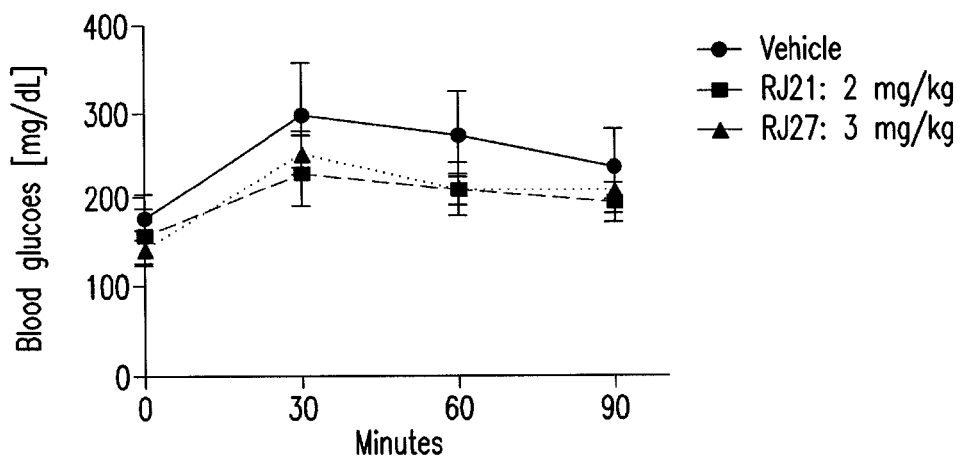
FIG. 2A shows the evolutions of the levels of blood glucose of DIO mice fed with RJ21, a galanal analogue (RJ27), or vehicle in an in vivo biological assay.
Figure 2B:
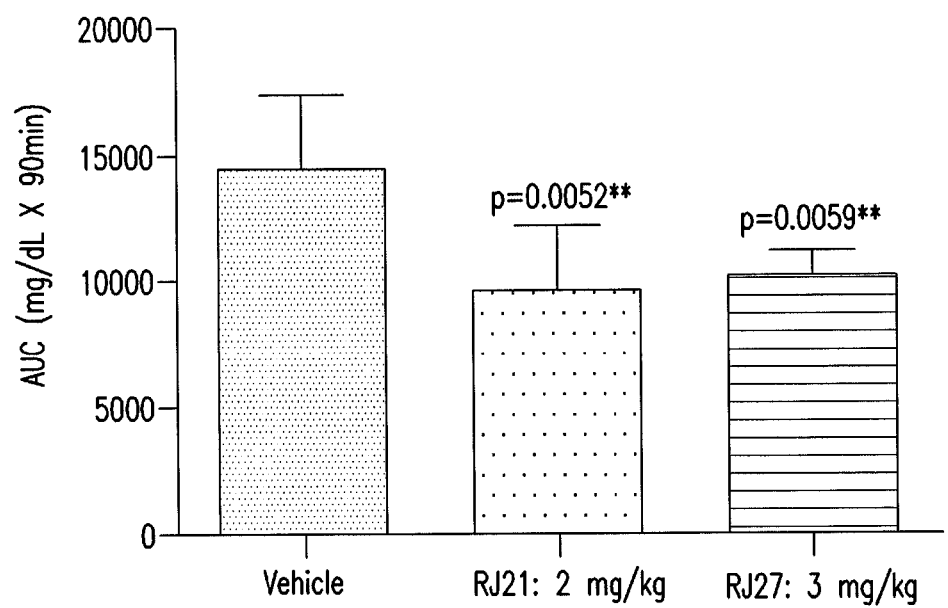
FIG. 2B shows the area under the curve (AUC) of each curve in FIG. 2A.

The effect of the compounds to the homeostasis of blood glucose using oral glucose tolerance test (OGTT) was examined in this example. Fasted DIO mice were gavaged with RJ21, RJ27, or vehicle alone, and received an oral glucose challenge (2 g/kg body weight) 30 minutes later. The level of blood glucose was measured right before (0 minute) and every 30 minutes after the glucose gavage. The kinetics of blood glucose level is depicted in FIG. 2A, and area under the curve (AUC) of each curve in FIG. 2A was calculated and displayed as bar graph in FIG. 2B. The glucose level in RJ21-treated mice (N=6) and in RJ27-treated mice (N=6) was significantly lower than that in vehicle-treated mice (N=12). This result indicates the acute hypoglycemic effect of RJ21 and RJ27 on DIO mice, and the potential of these compounds to improve glucose homeostasis in obese subject.

Other Embodiments

All of the features disclosed in this specification may be combined in any combination. Each feature disclosed in this specification may be replaced by an alternative feature serving the same, equivalent, or similar purpose. Thus, unless expressly stated otherwise, each feature disclosed is only an example of a generic series of equivalent or similar features.

From the above description, one skilled in the art can easily ascertain the essential characteristics of the present invention, and without departing from the spirit and scope thereof, can make various changes and modifications of the invention to adapt it to various usages and conditions. Thus, other embodiments are also within the claims.

What is claimed is:

1. A process of preparing a compound of Formula (VI) comprising converting a compound of Formula (V) to the compound of Formula (VI):

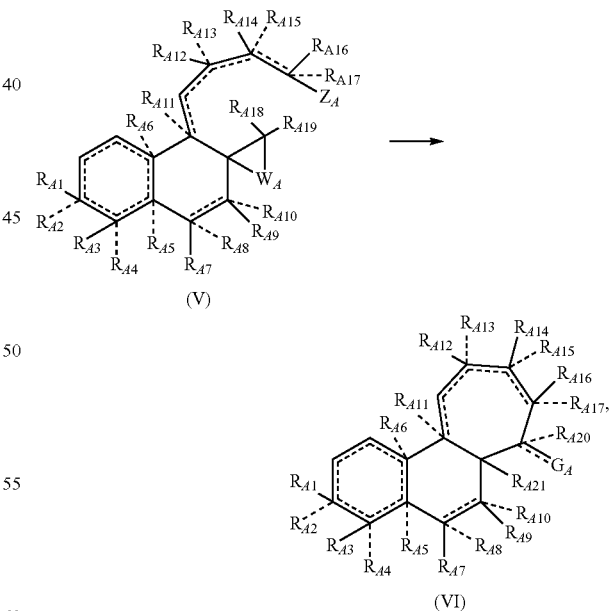

wherein:

$G_A$ is hydrogen, halogen, =O, =S, —N(R")$_2$, —SR", —OR", alkenyl, alkynyl, an amide group, an ester group, a phosphate group, an aldehyde group, a nitrile group, an imino group, a ketone group, a thione group, an isonitrile group, an isothiocyanide group, a carbamate group, a thiocarbamate group, or a cyclic or acyclic, substituted or unsubstituted, branched or unbranched, (hetero)aliphatic group having 1 to 6 carbon atoms, wherein R" is hydrogen, a cyclic or acyclic, saturated or unsaturated, substituted or unsubstituted, branched or unbranched, (hetero)aliphatic group having 1 to 16 carbon atoms, an ester group, a ketone group, or a thione group;

$W_A$ is —O—, —S—, or —NR"—;

$Z_A$ is alkenyl, alkynyl, an amide group, an ester group, an aldehyde group, a nitrile group, an imino group, a ketone group, a thione group, an isonitrile group, an isothiocyanide group, a thioate group, a thioamide, a dithioate, a carbamate group, a thiocarbamate group, an isocyanato group, or an isothiocyanato group;

$R_{A1}$, $R_{A2}$, $R_{A3}$, $R_{A4}$, $R_{A5}$, $R_{A6}$, $R_{A7}$, $R_{A8}$, $R_{A9}$, and $R_{A10}$ are each independently hydrogen, halogen, or a cyclic or acyclic, substituted or unsubstituted, branched or unbranched, (hetero)aliphatic group having 1 to 6 carbons;

$R_{A11}$, $R_{A13}$, $R_{A15}$, and $R_{A17}$ are each independently hydrogen, halogen, or a cyclic or acyclic, substituted or unsubstituted, branched or unbranched, (hetero)aliphatic group having 1 to 6 carbon atoms;

$R_{A12}$, $R_{A14}$, and $R_{A16}$ are each independently halogen, —N(R")$_2$, —SR", —OR", alkyl, alkenyl, alkynyl, an amide group, a carboxyl group, an ester group, an aldehyde group, a nitrile group, an imino group, a ketone group, a thione group, an isonitrile group, an isothiocyanide group, a urea group, a carbamate group, or a thiocarbamate group, or $R_{A14}$ and $R_{A15}$ are joined to form =O or =S;

$R_{A18}$ and $R_{A19}$ are each independently hydrogen, halogen, or a cyclic or acyclic, substituted or unsubstituted, branched or unbranched, (hetero)aliphatic group having 1 to 6 carbon atoms;

$R_{A20}$ is hydrogen, halogen, or a cyclic or acyclic, substituted or unsubstituted, branched or unbranched, (hetero)aliphatic group having 1 to 6 carbon atoms; and $R_{A21}$ is hydrogen, halogen, —N(R")$_2$, —SR", —OR", alkenyl, alkynyl, an amide group, a carboxyl group, an ester group, an aldehyde group, a nitrile group, an imino group, a ketone group, a thione group, an isonitrile group, an isothiocyanide group, a carbamate group, a thiocarbamate group, or a cyclic or acyclic, substituted or unsubstituted, branched or unbranched, (hetero)aliphatic group having 1 to 6 carbon atoms.

2. The process of claim 1, further comprising converting a compound of Formula (IV) to the compound of Formula (V):

(IV)

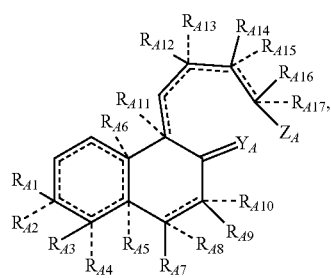

wherein $Y_A$ is =O, =S, =NR", or a cyclic or acyclic, substituted or unsubstituted, branched or unbranched, (hetero)aliphatic group having 1 to 6 carbon atoms.

3. The process of claim 2 further comprising converting a compound of Formula (III) to the compound of Formula (IV):

(III)

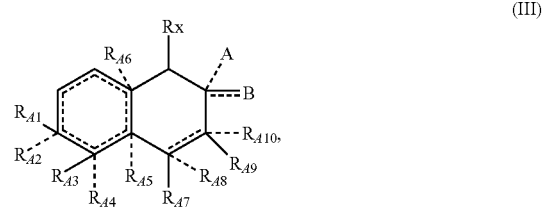

wherein:

$R_x$ is halogen, =O, =S, —NR"H, —SR", —OR", alkyl, alkenyl, alkynyl, an amide group, an ester group, an aldehyde group, a nitrile group, an imino group, a ketone group, a thione group, an isonitrile group, an isothiocyanide group, a carbamate group, or a thiocarbamate group, wherein R" is hydrogen, a cyclic or acyclic, saturated or unsaturated, substituted or unsubstituted, branched or unbranched, (hetero)aliphatic group having 1 to 16 carbon atoms, an ester group, a ketone group, or a thione group;

group A is hydrogen, halogen, or a cyclic or acyclic, substituted or unsubstituted, branched or unbranched, (hetero)aliphatic group having 1 to 6 carbon atoms; and group B is halogen, =O, =S, —NR"H, —SR", —OR", alkenyl, alkynyl, an amide group, an ester group, an aldehyde group, a nitrile group, an imino group, a ketone group, a thione group, an isonitrile group, an isothiocyanide group, a carbamate group, or a thiocarbamate group;

or $R_x$ and group A join to form a ring.

4. The process of claim 1, wherein the compound of Formula (VI) is a compound of Formula (VI-A):

(VI-A)

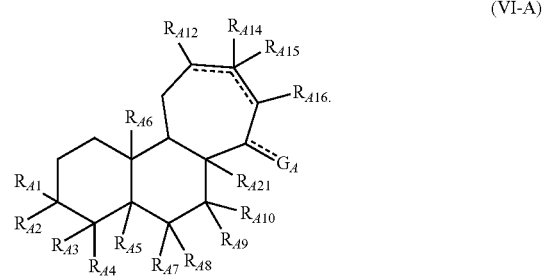

5. The process of claim 1, wherein the compound of Formula (VI) is a compound of the formula:

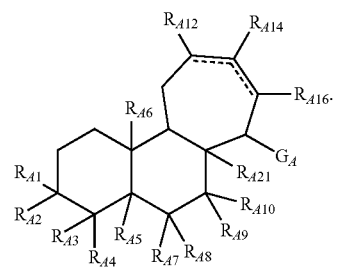

6. The process of claim 1, wherein the compound of Formula (VI) is a compound of Formula (VI-B):

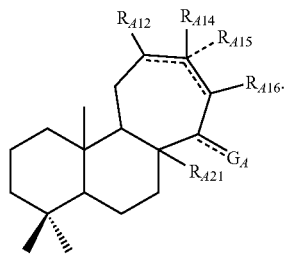

(VI-B)

7. The process of claim 1, wherein the compound of Formula (VI) is a compound of Formula (VI-C):

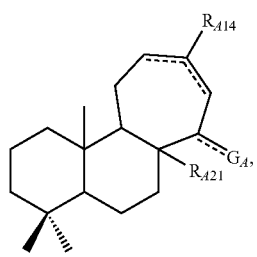

(VI-C)

wherein $G_A$ is =O or —OR", and $R_{A21}$ is —CH$_2$OR" or an aldehyde group, and wherein the two instances of R" are the same or different.

8. The process of claim 7, wherein the compound of Formula (VI) is a compound of Formula (VI-D):

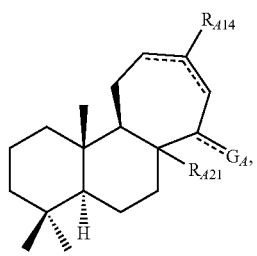

(VI-D)

9. The process of claim 1, wherein $G_A$ is =O or —OR"; $R_{A21}$ is —CH$_2$OR" or an aldehyde group; $W_A$ is —O—; $Z_A$ is an amide group, an ester group, an aldehyde group, a nitrile group, an imino group, or a ketone group; $Y_A$ is =CH$_2$; or $R_{A14}$ is alkyl, a carboxyl group, an ester group, or an aldehyde group.

10. The process of claim 9, wherein $Z_A$ is cyano.

* * * * *